(12) United States Patent
Kadel et al.

(10) Patent No.: US 11,254,987 B2
(45) Date of Patent: Feb. 22, 2022

(54) PD-L1 PROMOTER METHYLATION IN CANCER

(71) Applicant: Genentech, Inc., South San Francisco, CA (US)

(72) Inventors: Edward Kadel, South San Francisco, CA (US); Marcin Kowanetz, South San Francisco, CA (US); Kimberly Walter, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 411 days.

(21) Appl. No.: 15/821,407

(22) Filed: Nov. 22, 2017

(65) Prior Publication Data

US 2018/0216196 A1    Aug. 2, 2018

Related U.S. Application Data

(63) Continuation of application No. PCT/US2016/034856, filed on May 27, 2016.

(60) Provisional application No. 62/168,668, filed on May 29, 2015.

(51) Int. Cl.
| C07K 16/28 | (2006.01) |
| C12Q 1/6886 | (2018.01) |
| A61P 35/00 | (2006.01) |

(52) U.S. Cl.
CPC ............ *C12Q 1/6886* (2013.01); *A61P 35/00* (2018.01); *C07K 16/2827* (2013.01); *C07K 2317/56* (2013.01); *C07K 2317/76* (2013.01); *C12Q 2600/106* (2013.01); *C12Q 2600/154* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| RE30,985 E | 6/1982 | Cartaya |
| 4,419,446 A | 12/1983 | Howley et al. |
| 4,485,045 A | 11/1984 | Regen |
| 4,544,545 A | 10/1985 | Ryan et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 4,975,278 A | 12/1990 | Senter |
| 5,013,556 A | 5/1991 | Woodie et al. |
| 5,122,469 A | 6/1992 | Mather et al. |
| 5,208,020 A | 5/1993 | Chari et al. |
| 5,229,275 A | 7/1993 | Goroff |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,591,828 A | 1/1997 | Bosslet et al. |
| 5,641,870 A | 6/1997 | Rinderknecht et al. |
| 5,648,237 A | 7/1997 | Carter |
| 5,693,780 A | 12/1997 | Newman et al. |
| 5,731,168 A | 3/1998 | Carter et al. |
| 5,739,277 A | 4/1998 | Presta et al. |
| 5,750,373 A | 5/1998 | Garrard et al. |
| 5,789,199 A | 8/1998 | Joly et al. |
| 5,807,706 A | 9/1998 | Carter et al. |
| 5,821,333 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,075,181 A | 6/2000 | Kucherlapati et al. |
| 6,150,584 A | 11/2000 | Kucherlapati et al. |
| 6,194,551 B1 | 2/2001 | Idusogie et al. |
| 6,242,195 B1 | 2/2001 | Idusogie et al. |
| 6,267,958 B1 | 7/2001 | Andya et al. |
| 6,417,429 B1 | 7/2002 | Hein et al. |
| 6,420,548 B1 | 7/2002 | Vézina et al. |
| 6,528,624 B1 | 3/2003 | Idusogie et al. |
| 6,538,124 B1 | 3/2003 | Idusogie et al. |
| 6,602,684 B1 | 8/2003 | Umaña et al. |
| 6,737,056 B1 | 5/2004 | Presta |
| 7,125,978 B1 | 10/2006 | Vézina et al. |
| 7,642,228 B2 | 1/2010 | Carter et al. |
| 7,695,936 B2 | 4/2010 | Carter et al. |

(Continued)

FOREIGN PATENT DOCUMENTS

| CN | 101248089 A | 8/2008 |
| CN | 101355965 A | 1/2009 |

(Continued)

OTHER PUBLICATIONS

Zemach etal (SE, 10.1126, pp. 1-10, 2010).*
[Fundamental Immunology p. 242 (William E. Paul, M.D. ed., 3d ed; 1993)].*
Ahmadzadeh, M. et al. (Aug. 20, 2009). "Turner Antigen-Specific CD8T Cells Infiltrating the Tumor Express High Levels of PD-1 and are Functionally Impaired," *Blood* 114(8):1537-1544.
Barnes, D. et al. (1980). "Methods for Growth of Cultured Cells in Serum-Free Medium," *Anal. Biochem.* 102:255-270.

(Continued)

*Primary Examiner* — Brad Duffy

(74) *Attorney, Agent, or Firm* — Morrison & Foerster LLP

(57) ABSTRACT

This invention provides methods for the treatment of cancer in subjects having medium or low methylation level in the PD-L1 promoter region. Also provided are related kits and articles of manufacture.

20 Claims, 22 Drawing Sheets

Specification includes a Sequence Listing.

(56) References Cited

U.S. PATENT DOCUMENTS

| | | | |
|---|---|---|---|
| 8,216,805 | B2 | 7/2012 | Carter et al. |
| 8,217,149 | B2 | 7/2012 | Irving et al. |
| 2002/0004587 | A1 | 1/2002 | Miller et al. |
| 2002/0136719 | A1 | 9/2002 | Shenoy et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0079574 | A1 | 4/2005 | Bond |
| 2005/0119455 | A1 | 6/2005 | Fuh et al. |
| 2005/0266000 | A1 | 12/2005 | Bond et al. |
| 2007/0117126 | A1 | 5/2007 | Sidhu et al. |
| 2007/0160598 | A1 | 7/2007 | Dennis et al. |
| 2007/0237764 | A1 | 10/2007 | Birtalan et al. |
| 2007/0292936 | A1 | 12/2007 | Barthelemy et al. |
| 2009/0002360 | A1 | 1/2009 | Chen et al. |
| 2013/0034559 | A1 | 2/2013 | Queva et al. |
| 2013/0089553 | A1 | 4/2013 | Carter et al. |

FOREIGN PATENT DOCUMENTS

| | | | | |
|---|---|---|---|---|
| DE | 266710 | A3 | 4/1989 | |
| EP | 0 183 070 | A2 | 6/1986 | |
| EP | 0 183 070 | A3 | 6/1986 | |
| EP | 0 183 070 | B1 | 6/1986 | |
| EP | 0 244 234 | A2 | 11/1987 | |
| EP | 0 244 234 | A3 | 11/1987 | |
| EP | 0 244 234 | B1 | 11/1987 | |
| EP | 0 244 234 | B2 | 11/1987 | |
| EP | 0 308 936 | A2 | 3/1989 | |
| EP | 0 308 936 | B1 | 3/1989 | |
| EP | 0 402 226 | A1 | 12/1990 | |
| EP | 0 404 097 | A2 | 12/1990 | |
| EP | 0 404 097 | A3 | 12/1990 | |
| EP | 0 404 097 | B1 | 12/1990 | |
| EP | 1 691 833 | B1 | 3/2010 | |
| WO | WO-1981/01145 | A1 | 4/1981 | |
| WO | WO-1987/00195 | A1 | 1/1987 | |
| WO | WO-1988/07378 | A1 | 10/1988 | |
| WO | WO-1990/03430 | A1 | 4/1990 | |
| WO | WO-1990/13646 | A1 | 11/1990 | |
| WO | WO-1991/00360 | A1 | 1/1991 | |
| WO | WO-1992/20373 | A1 | 11/1992 | |
| WO | WO-1993/08829 | A1 | 5/1993 | |
| WO | WO-1993/11161 | A1 | 6/1993 | |
| WO | WO-1993/16185 | A2 | 8/1993 | |
| WO | WO-1993/16185 | A3 | 8/1993 | |
| WO | WO-1993/21232 | A1 | 10/1993 | |
| WO | WO-1994/04690 | A1 | 3/1994 | |
| WO | WO-1994/11026 | A2 | 5/1994 | |
| WO | WO-1994/11026 | A3 | 5/1994 | |
| WO | WO-1996/27011 | A1 | 9/1996 | |
| WO | WO-1997/30087 | A1 | 8/1997 | |
| WO | WO-1997/38731 | A1 | 10/1997 | |
| WO | WO-1998/58964 | A1 | 12/1998 | |
| WO | WO-1999/22764 | A1 | 5/1999 | |
| WO | WO-1999/51642 | A1 | 10/1999 | |
| WO | WO-2000/42072 | A2 | 7/2000 | |
| WO | WO-2000/42072 | A3 | 7/2000 | |
| WO | WO-2000/61739 | A1 | 10/2000 | |
| WO | WO-2001/29246 | A1 | 4/2001 | |
| WO | WO-2003/011878 | A2 | 2/2003 | |
| WO | WO-2003/011878 | A3 | 2/2003 | |
| WO | WO-2003/084570 | A1 | 10/2003 | |
| WO | WO-2003/085119 | A1 | 10/2003 | |
| WO | WO-2004/032828 | A2 | 4/2004 | |
| WO | WO-2004/032828 | A3 | 4/2004 | |
| WO | WO-2004/056312 | A2 | 7/2004 | |
| WO | WO-2004/056312 | A3 | 7/2004 | |
| WO | WO-2004/106381 | A1 | 12/2004 | |
| WO | WO-2005/035586 | A1 | 4/2005 | |
| WO | WO-2005/035778 | A1 | 4/2005 | |
| WO | WO-2005/061547 | A2 | 7/2005 | |
| WO | WO-2005/061547 | A3 | 7/2005 | |
| WO | 2006133396 | A2 | 12/2006 | |
| WO | WO-2007/005874 | A2 | 1/2007 | |
| WO | WO-2007/005874 | A3 | 1/2007 | |
| WO | WO-2007/042261 | A2 | 4/2007 | |
| WO | WO-2007/042261 | A3 | 4/2007 | |
| WO | 2006133396 | A3 | 8/2007 | |
| WO | WO-2008/119567 | A2 | 10/2008 | |
| WO | WO-2008/119567 | A3 | 10/2008 | |
| WO | WO-2008/119567 | A8 | 10/2008 | |
| WO | WO-2010/077634 | A1 | 7/2010 | |
| WO | WO-2011/066389 | A1 | 6/2011 | |
| WO | WO-2013019906 | A1 * | 2/2013 | ......... C07K 16/3046 |
| WO | WO-2014/151006 | A2 | 9/2014 | |
| WO | WO-2014/151006 | A3 | 9/2014 | |
| WO | WO-2015/035112 | A1 | 3/2015 | |

OTHER PUBLICATIONS

Boerner, P. et al. (Jul. 1, 1991). "Production of Antigen-Specific Human Monoclonal Antibodies From in Vitro-Primed Human Splenocytes," *J. Immunol.* 147(1):86-95.

Brennan, M. et al. (Jul. 5, 1985). "Preparation of Bispecific Antibodies by Chemical Recombination of Monoclonal immunoglobulin $G_1$ Fragments," *Science* 229:81-83.

Brodeur, B.R. et al. (1987). "Mouse-Human Myeloma Partners for the Production of Heterohybridomas," Chapter 4 in *Monoclonal Antibody Production Techniques and Applications*, Marcel-Dekker, Inc. New York, New York, pp. 51-63.

Brüggemann, M. et al. (1993). "Designer Mice: The Production of Human Antibody repertoires in Transgenic Animals," *Year in Immuno.* 7:33-40.

Caron, P.C. et al. (Oct. 1, 1992). "Engineering Humanized Dimeric Forms of IgG Are More Effective Antibodies," *J. Exp. Med.* 176:1191-1195.

Carter, P. et al. (Feb. 1992). "High Level *Escherichia coli* Expression and Production of a Bivalent Humanized Antibody Fragment," *Bio/Technology* 10:163-167.

Carter, P. et al. (May 1992). "Humanization of Anti-p185$^{HER2}$ Antibody for Human Cancer Therapy," *Proc. Natl. Acad. Sci. USA* 89:4285-4289.

Champe, M. et al. (Jan. 20, 1995). "Monoclonal Antibodies That Block the Activity of Leukocyte Function-associated Antigen 1 Recognize Three Discrete Epitopes in the Inserted Domain of CDlla," *J. Biol. Chem.* 270(3):1388-1394.

Chari, R.V. et al. (Jan. 1, 1992). "Immunoconjugates Containing Novel Maytansinoids: Promising Anticancer Drugs," *Cancer Research* 52:127-131.

Charlton, K.A. (2003). "Expression and Isolation of Recombinant Antibody Fragments in *E. coli*," Chapter 14 in *Methods in Molecular Biology*, B.K.C. Lo, ed., Humana Press, Totowa, NJ, vol. 248, pp. 245-254.

Chothia, C. (1976). "The Nature of the Accessible and Buries Surfaces in Proteins," *J. Mol. Biol.* 105:1-14.

Chothia, C. et al. (1987). "Canonical Structures for the Hypervariable Regions of Immunoglobulins," *J. Mol. Biol.* 196:901-917.

Clackson, T. et al. (Aug. 15, 1991). "Making Antibody Fragments Using Phage Display Libraries," *Nature*, 352:624-628.

clinicaltrials.gov (Apr. 29, 2009). "Her2 and TGFBeta Cytotoxic T Cells in Treatment of Her2 Positive Malignancy (HERCREEM)," located at <https://clinicaltrials.gov/ct2/show/NCT00889954>, last visited on Sep. 21, 2018, 9 pages.

Cole, S.P.C. et al. (1985). "The EBV-Hypbridoma Techinque and Its Application to Human Lung Cancer," *Monoclonal Antibodies and Cancer Therapy*, Alan R. Liss, p. 77-96.

Cunningham, B.C. et al. (Jun. 2, 1989). "High-Resolution Epitope Mapping of hGH-Receptor Interactions by Alanine-Scanning Mutagenesis," *Science* 244:1081-1085.

De Ruijter, T.C. et al. (Jul. 2015). Formalin-Fixed, Paraffin-Embedded FFPE) Tissue Epigenomics Using Infinium HumanMethylation450 BeadChip *Assays Laboratory Investigation* 95:833-842.

(56) References Cited

OTHER PUBLICATIONS

Epstein, D.A. et al. (Jun. 1985). "Biological Activity of Liposome-Encapsulated Murine Interferon γ is Mediated by a Cell Membrane Receptor," *Proc. Natl. Acad. Sci. USA* 82:3688-3692.

Farlik, M. et al. (2005). "Single-Cell DNA Methylome Sequencing and Bioinformatic Inference of Epigenomic Cell-State Dynamics," *Cell Reports* 10:1386-1397.

Fellouse, F.A. et al. (Aug. 24, 2004). "Synthetic Antibodies From a Four-Amino-Acid Code: A Dominant Role for Tyrosine in Antigen Recognition," *Proc. Natl. Acad. Sci. USA* 101 (34):12467-12472.

Fernández, A.F. et al. (Jan. 2015). "H3K4me1 Marks DNA Regions Hypomethylated During Aging in Human Stem and Differentiated Cells," *Genome Research* 25(1):27-40.

Fleer, R. et al. (Oct. 1991). "Stable Multicopy Vectors For High-Level Secretion of Recombinant Human Serum Albumin by *Kluyveromyces* Yeasts," *Bio/Technology* 9:968-975.

Frommer, M. et al. (Mar. 1992). "A Genomic Sequencing Protocol That Yields a Positive Display of 5-Methylcytosine Residues in Individual DNA Strands," *Proc. Natl. Acad. Sci.* 89:1827-1831.

Gabizon, A. et al. (Oct. 4, 1989). "Pharmacokinetics and Tissue Distribution of Doxorubicin Encapsulated in Stable Liposomes With Long Circulation Times," *J. National Cancer Inst.* 81(19)1484-1488.

Gajewski, T.F et al. (Apr. 2011). "Molecular Profiling to Identify Relevant Immune Resistance Mechanisms in the Tumor Microenvironment," *Curr. Opin. Immunol.* 23(2):286-292, 10 pages.

Gerngross, T.U. (Nov. 2004). "Advances in the Production of Human Therapeutic Proteins in Yeasts and Filamentous Fungi," *Nat. Biotech.* 22(11): 1409-1414.

Goding, J.W. (1983). "Production of Monoclonal Antibodies," Chapter 3 in *Monoclonal Antibodies: Principles and Practice*, Academic Press., pp. 56-103, Table of Contents p. vii-ix.

Graham, F.L et al. (1977). "Characteristics of a Human Cell Line Transformed by DNA From Human Adenovirus Type 5," *J. Gen. Virol.* 36:59-72.

Griffiths, A.D. et al. (1993). "Human Anti-Self Antibodies with High Specificity From Phage Display Libraries," *EMBO J.* 12(2)725-734.

Gruber, M. et al. (1994). "Efficient Tumor Cell Lysis Mediated by a Bispecific Single Chain Antibody Expressed in *Escherichia coli,*" *J. Immunol.* 152:5368-5374.

Guss, B. et al. (1986). "Structure of the IgG-Binding Regions of Streptococcal Protein G," *EMBO J.* 5(7):1567-1575.

Ham, R.G et al. (1979). "Media and Growth Requirement," Chapter 5 In *Methods in Enzymology*, Academic Press, Inc. 58:44-93.

Herbst, R.S et al. (Nov. 27, 2014). "Predictive Correlated of Response to the Anti-PD-L1 Antibody MPDL23280A in Cancer Patients," *Nature* 515(7528):563-567.

Hinman, L.M. et al. (Jul. 15, 1993). "Preparation and Characterization of Monoclonal Antibody Conjugates of Calicheamicins: A Novel and Potent Family of Antitumor Antibodies," *Cancer Research* 53:3336-3342.

Holliger, P. et al. (Jul. 1993)."Diabodies" Small bivalent and bispecific antibody fragments, *Proc. Natl. Acad. Sci. USA* 90:6444-6448.

Hoogenboom, H.R et al. (1992). "By-Passing Immunisation Human Antibodies From Synthetic Repertoires of Germline $V_H$ Gene Segments Rearranged in Vitro," J. Mol. Biol. 227:381-388.

Hoogenboom, H.R. (2001). *Methods in Molecular Biology*, O'Brien, P.M. et al., eds.,. Humana Press: Totowa, N.J. 178:1-37.

Hwang, K.J. et al. (Jul. 1980). "Hepatic Uptake and Degradation of Unliamellar Sphingomyelin/Cholesterol Liposomes: A Kinetic Study," *Proc. Natl. Acad. Sci. USA* 77:4030-3034.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555.

Jakobovits, A. et al. (Mar. 18, 1993). "Germ-line Transmission and Expression of a Human-Derived Yeast Artificial Chromosome," *Nature* 362:255-258.

Johnson, K.S. et al. (2003). "The Kabat Database and a Bioinformatics Example," Chapter 2 in *Methods in Molecular Biology™ Antibody Engineering Methods and Protocols*, Lo, B.K.C. ed., Human Press, Totowa, NJ, 284:11-25.

Jones, E.W. (Jan. 1977). "Proteinase Mutants of *Saccharomyces cerevisiae,*" *Genetics* 85:23-33.

Jones, P.T et al. (May 29, 1986). "Replacing the Complementarity-Determining Regions in a Human Antibody with Those From a Mouse," *Nature* 321:522-525.

Keir, M.E. et al. (2008, e-pub. Jan. 2, 2008). "PD-1 and Its Ligands in Tolerance and Immunity," *Annu. Rev. Immunol.* 26:677-704.

Köhler, G. et al. (Aug. 7, 1975). "Continuous Cultures of Fused Cells Secreting Antibody of Predefined Specificity," *Nature*, 256:495-497.

Kostelny, S.A et al. (Mar. 1, 1992). "Formation of a Bispecific Antibody by the Use of Leucine Zippers," *J. Immunol.* 148(5): 1547-1553.

Kozbor, D. (Dec. 1984). "A Human Hybrid Myeloma For Production of Human Monoclonal Antibodies," *J. Immunol.* 133(6):3001-3005.

Lee, C.V. et al. (2004). "High-Affinity Human Antibodies From Phage-displayed Synthetic Fab Libraries with a Single Framework Scaffold," *J. Mol. Biol.* 340(5):1073-1093.

Lee, C.V. et al. (2004). "Bivalent Antibody Phage Display Mimics Natural Immunoglobulin," *J. Immunol. Methods* 284(1-2):119-132.

Lehne, B. et al. (Feb. 2015). "A Coherent Approach for Analysis of the Illumina Humanmethylation450 Beadchip Improves Data Quality and Performance in Epigenome-Wide Association Studies," *Genome Biology* 16(37):1-12.

Lehninger, A.L. (1975). "The Amino Acid Building Blocks of Proteins," in *Biochemistry 2nd ed.*, Worth Publishers, New York, pp. 73-75.

Li, H. et al. (Feb. 2006, e-pub. Jan. 22, 2006). "Optimization of Humanized IgGs in Glycoengineered *Pichia pastoris,*" *Nat. Biotech.* 24(2):210-215.

Li, J. et al. (Mar. 7, 2006). "Human Antibodies for Immunotherapy Development Generated Via a Human B Cell Hybridoma Technology," *Proc. Natl. Acad. Sci. USA* 103(10):3557-3562.

Lim, E.T. et al. (Jul. 31, 2014). "Distribution and Medical Impact of Loss-of-Function Variants in the Finnish Founder Population," *PLOS Genetics* 10(7)(e1004494)1-12.

Lindmark, R. et al. (1983). "Binding of Immunoglobulins to Protein A and Immunoglobulin Levels in Mammalian Sera," *J. Immunol. Meth.* 62:1-13.

Lipson, E.J. et al. (Jul. 2013). "PD-L1 Expression in the Merkel Cell Carcinoma Microenvironment: Association With Inflammation, Merkel Cell Polyomavirus, and Overall Survival," *Cancer Immunol. Res.* 1 (1):54-63, 20 pages.

Lode, H.N. et al. (Jul. 15, 1998). "Targeted Therapy with a Novel Enediyene Antibiotic Calicheamicin $\theta^1_1$ Effectively Suppresses Growth and Dissemination of Liver Metastases in a Syngeneic Model of Murine Neuroblastoma," *Cancer Research* 58:2925-2928.

Marks, J.D et al. (1991). "By-Passing Immunization Human Antibodies from V-Gene Libraries Displayed on Phage," *J. Mol. Biol.*, 222:581-597.

Marks, J.D. et al. (Jul. 1992). "By-Passing Immunization: Building High Affinity Human Antibodies by Chain Shuffling," *Bio/Technology* 10:779-783.

Marks, J.D. et al. (2004). "Selection of Human Antibodies from Phage Display Libraries," Chapter 8 in *Methods in Molecular Biology™ Antibody Engineering Methods and Protocols*, LO, B.K.C. ed., Humana Press Inc., Totowa, NJ, 248:161-176, twenty nine pages.

Martin, F.J. et al. (Jan. 10, 1982). "Irreversible Coupled of Immunoglobulin Fragments to Preformed Vesicles. An Improved Method for Liposome Targeting," *J. Biol. Chem.* 257(1):286-288.

Massey, R.J. (Jul. 30, 1987). "Catalytic Antibodies Catching On," *Nature* 328:457-458.

Mather, J.P. (1980). "Establishment and Characterization of Two Distinct Mouse Testicular Epithelial Cell Lines," *Biol. Reprod.* 23:243-251.

(56) References Cited

OTHER PUBLICATIONS

Mather, J.P. et al. (1982). "Culture of Testicular Cells in Hormone-Supplemented Serum-Free Medium," *Annals N. Y Acad. Sci.* 383:44-68.

McCafferty, J. et al. (December6, 1990). "PhageAntibodies: Filamentous Phage Displaying Antibody Variable Domains," *Nature* 348:552-554.

Milstein, C. et al. (Oct. 6, 1983). "Hybrid Hybridomas and Their Use in Immunohistochemistry," *Nature* 305:537-539.

Morimoto, K. et al. (1992). "Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.

Morris, T.J. et al. (Jan. 15, 2015, e-pub. Sep. 16, 2014). "Analysis pipelines and packages for Infinium HumanMethylation450 BeadChip (450k) data," *Methods* 72:3-8.

Morrison, S.L. et al. (Nov. 1984). "Chimeric Human Antibody Molecules: Mouse Antigen-Binding Domains With Human Constant Region Domains," *Proc. Natl. Acad. Sci. USA* 81:6851-6855.

Munson, P.J. et al. (1980). "Ligand: A Versatile Computerized Approach for Characterization of Ligand-Binding Systems," *Anal. Biochem.* 107:220-239.

Murakami, M.S et al. (1995). "Cell Cycle Regulation, Oncogenes, and Antineoplastic drugs," Chapter 1 in *The Molecular Basis of Cancer*, Mendelsohn, J. et al. eds., W.B. Saunders, Philadelphia, pp. 3-17.

Neuberger, M.S. et al. (Dec. 13, 1984). "Recombinant Antibodies Possessing Novel Effector Functions," *Nature* 312: 604-608.

Nicolaou, K.C. et al. (1994). "Calicheamicin $\theta^\gamma 1$: A Rationally Designed Molecule with Extremely Potent and Selective DNA Cleaving Properties and Apoptosis Inducing Activity," *Angewandte Chemie International* 33(2):183-186.

Okazaki, A. et al. (2004). "Fucose Depletion from Human IgG1 Oligosaccharide Enhances Binding Enthalpy and Association Rate Between lgG1 and Fc,γRlIia," *J. Mol. Biol.* 336:1239-1249.

Okazaki, T. et al. (2007, e-pub. Jul. 2, 2007). "PD-1 and PD-1 Ligands: From Discovery to Clinical Application," *Intern. Immun.* 19(7):813-824.

Philips, G.K et al. (Jan. 2015, e-pub. Oct. 16, 2014). "Therapeutic Uses of Anti-PD-1 and Anti-PD-L1 Antibodies," *Int. Immunol.* 27(1):39-46.

Plückthun, A. (1992). "Mono- and Bivalent Antibody Fragments Produced in *Escherichia coli*: Engineering, Folding and Antigen Biding," *Immunol. Revs.* 130:151-188.

Plückthun, A. (1994). "Antibodies From *Escherichia coli*," Chapter 11 in *The Pharmacology of Monoclonal Antibodies*, vol. 113, Rosenburg, M. et al. eds., Springer-Verlag, New York, pp. 269-315.

Presta, L.G. (1992). "Antibody Engineering," *Curr. Op. Struct. Biol.* 2:593-596.

Presta, L.G. et al. (Sep. 1, 1993). "Humanization of an Antibody Directed Against IgE," *J. Immunol.* 151(5):2623-2632.

Riechmann, L. et al. (Mar. 24, 1988). "Reshaping Human Antibodies for Therapy," *Nature* 332:323-329.

Reyes, G.R. et al. (Jun. 17, 1982). "Expression of Human β-Interferon cDNA Under the Control of a Thymidine Kinase Promoter From Herpes Simplex Virus," *Nature* 297:598-601.

Ripka, J. et al. (Sep. 1986). "Two Chinese Hamster Ovary Glycosylation Mutants Affected in the Conversion of GDP-Mannose to GDP-Fucose," *Arch. Biochem. Biophys.* 249(2):533-545.

Sandoval, J. et al. (Jun. 2011). "Validation of a DNA Methylation Microarray for 450,000 CpG Sites in the Human Genome," *Epigenetics* 6(6):692-702.

Shalaby, M.R. et al. (Jan. 1, 1992). "Development of Humanized Bispecific Antibodies Reactive with Cytotoxic Lymphocytes and Tumor Cells Overexpressing the HER2 Protooncogene," *J. Exp. Med.*, 175: 217-225.

Sharpe, A.H. et al. (Feb. 2002). "The B7-CD28 Superfamily," *Nat. Rev.* 2:116-126.

Shopes, B. (May 1, 1992). "A Genetically Engineered Human IgG Mutant With Enhanced Cytolytic Activity," *J. Immunol.* 148(9):2918-2922.

Sidhu, S.S. et al. (2004). "Phage-Displayed Antibody Libraries of Synthetic Heavy Chain Complementarity Determining Regions," *J. Mol. Bio.* 338(2):299-310.

Sims, M.J. et al. (Aug. 15, 1993). "A Humanized CD18 Antibody Can Block Function Without Cell Destruction," *J. Immunol.* 151:2296-2308.

Skerra, A. (1993). "Bacterial Expression of Immunogobulin Fragments," *Curr. Opinion in Immunol.* 5:256-262.

Spiess, C. et al. (Aug. 2013, e-pub. Jul. 7, 2013). "Bispecific Antibodies With Natural Architecture Produced by Co-Culture of Bacteria Expressing Two Distinct Half-Antibodies," *Nature Biotechnology* 31 (8) 753-758.

Stevenson, G.T. et al. (1989). "A Chimeric Antibody With Dual Fc Regions (bisFabFc) Prepared by Manipulation at the IgG Hinge," *Anti-Cancer Drug Design* 3:219-230.

Stinchcomb, D.T. et al. (Nov. 1, 1979). "Isolation and Characterization of a Yeast Chromosomal Replicator," *Nature* 282:39-43.

Suresh, M.R. et al. (1986). Bispecific Monoclonal Antibodies From Hybrid Hybridomas, *Methods in Enzymology* 121:210-228.

Sznol, M. et al. (Mar. 1, 2013). "Antagonist Antibodies to PD-1 and B7-H1 (PD-L1) in the Treatment of Advanced Human Cancer," *Clin. Cancer Res.* 19(5): 1021-1034.

Taube, J.M. et al. (Mar. 28, 2012). "Colocalization of Inflammatory Response With B7-H1 Expression In Human Melanocytic Lesions Supports an Adaptive Resistance Mechanism of Immune Escape," *Sci. Transl. Med.* 4(127)(217ra37):1-10.

Thompson, R.H. et al. (Apr. 1, 2006). "Tumor B7-H1 Is Associated with Poor Prognosis in Renal Cell Carcinoma Patients with Long-term Follow-up," *Cancer Res.* 66(7):3381-3385.

Tiedemann, R.L. et al. (Nov. 20, 2014). "Acute Depletion Redefines the Division of Labor Among DNA Methyltransferases in Methylating the Human Genome," *Cell Reports* 9:1554-1566.

Traunecker, A.et al. (1991). "Bispecific Single Chain Molecules (Janusins) Target Cytotoxic Lymphocytes on HIV Infected Cells," *EMBO J.* 10(12):3655-3659.

Tutt, A. et al. (Jul. 1, 1991). "Trispecific F(ab')$_3$ Derivatives That Use Cooperative Signaling Via The TCR/CD3 Complex and CD2 to Activate and Redirect Resting Cytotoxic T Cells," *J. Immunol.* 147(1):60-69.

Urlaub, G. et al. (Jul. 1980). "Isolation of Chinese Hamster Cell Mutants Deficient in Dihydrofolate Reductase Activity," *Proc. Natl. Acad. Sci. USA* 77(7):4216-4220.

Van Den Berg, J.A. et al. (Feb. 1990). "*Kluyveromyces* as a Host for Heterologous Gene Expression: Expression and Secretion of Prochymosin," *Bio/Technology* 8:135-139.

Van Dijk, M.A. et al. (2001). "Human Antibodies as Next Generation Therapeutics," *Curr. Opin. Pharmacol.* 5:368-374.

Vitetta, E.S. et al. (Nov. 20, 1987). "Redesigning Nature's Poisons to Create Anti-Tumor Reagents," *Science* 238:1098-1104.

Waterhouse, P. et al. (1993). "Combinatorial Infection and in vivo Recombination: A Strategy for Making Large Phage Antibody Repertoires," *Nuc. Acids. Res.* 21(9):2265-2266.

Winter, G. et al. (1994). "Making Antibodies by Phage Display Technology," *Ann. Rev. Immunol.* 12:433-455.

Wolff, E.A. et al. (Jun. 1, 1993). "Monoclonal Antibody Homodimers: Enhanced Antitumor Activity in Nude Mice," *Cancer Research* 53:2560-2565.

Wrangle, J. et al. (Nov. 12, 2013, e-pub. Oct. 25, 2013). "Alterations of Immune Response of Non-Small Cell Lung Cancer with Azacytidine," *Oncotarget* 4(11):2067-2079.

Yamada, A. et al. (Jan. 2013, e-pub. Dec. 4, 2012). "Next-Generation Peptide Vaccines for Advanced Cancer," *Cancer Sci.* 104(1):15-21.

Yamane-Ohnuki, N. et al. (Sep. 5, 2004, e-pub. Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," *Biotech. Bioeng.* 87(5):614-622.

Yaniv, M. (May 6, 1982). "Enhancing Elements for Activation of Eukaryotic Promoters," *Nature* 297:17-18.

(56) References Cited

OTHER PUBLICATIONS

Yazaki, P.J. et al. (2003). "Expression of Recombinant Antibodies in Mammalian Cell Lines," Chapter 15 in *Methods in Molecular Biology*, vol. 248, Lo, B.K.C. ed., Humana Press, Totowa, N.J., pp. 255-268.

Zamyatnin, A.A. (1972). "Protein Volume in Solution," *Prog. Biophys. Mol. Biol.* 24:107-123.

International Preliminary Report dated Dec. 5, 2017, for PCT Application No. PCT/US2016/034856, filed on May 27, 2016, 7 pages.

International Search Report dated Aug. 26, 2016, for PCT Application No. PCT/US2016/034856, filed on May 27, 2016, 6 pages.

Written Opinion dated Aug. 26, 2016, for PCT Application No. PCT/US2016/034856, filed on May 27, 2016, 6 pages.

Morris, T.J. et al. (2014). "ChAMP: 450k Chip Analysis Methylation Pipeline," Bioinformatics 30(3):428-430.

Extended European Search Report, dated Dec. 15, 2020, for European Application No. 20170755.1, filed on May 27, 2016, 10 pages.

\* cited by examiner

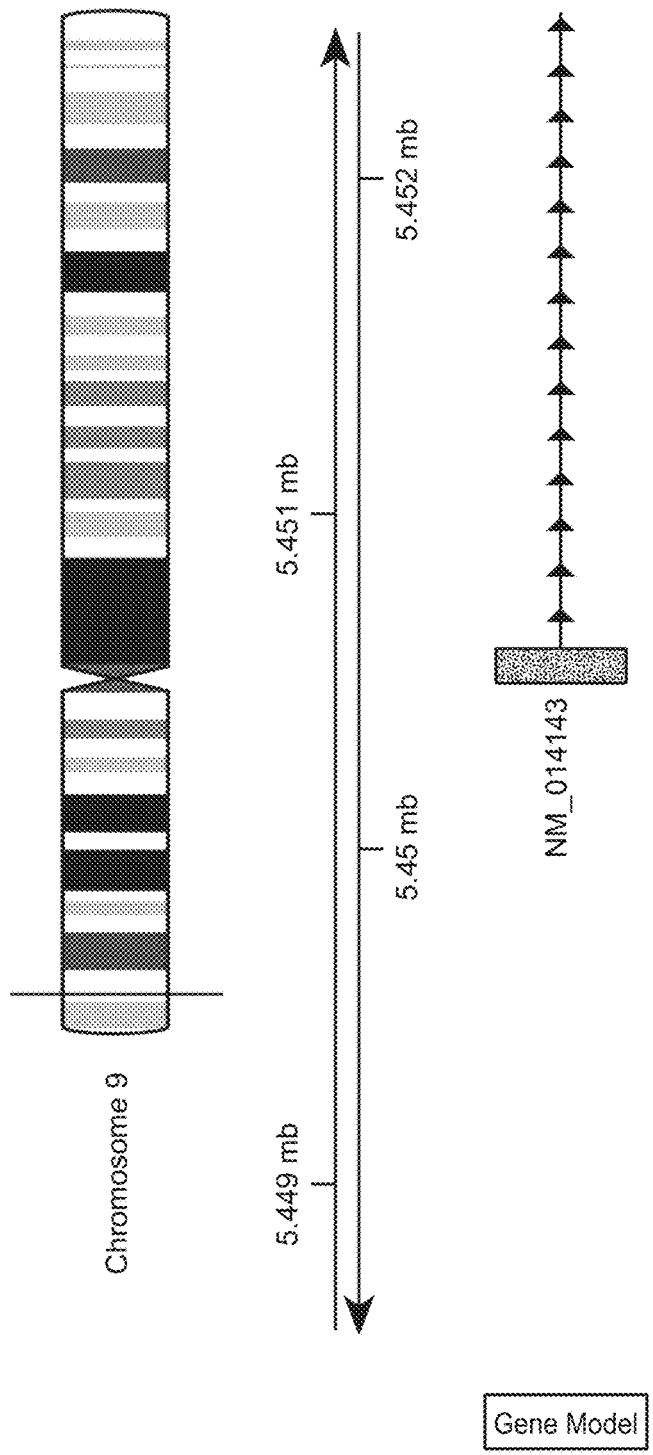

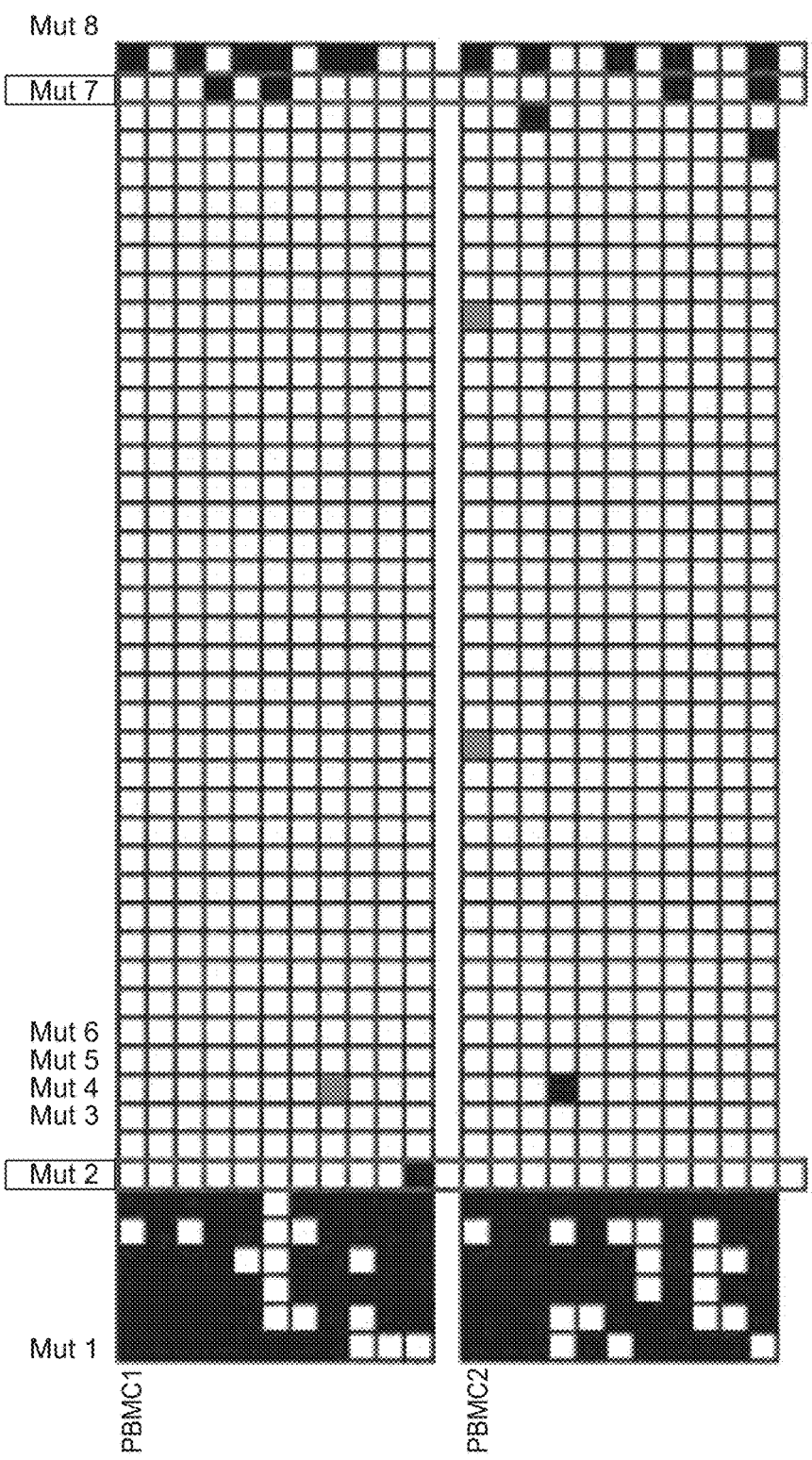

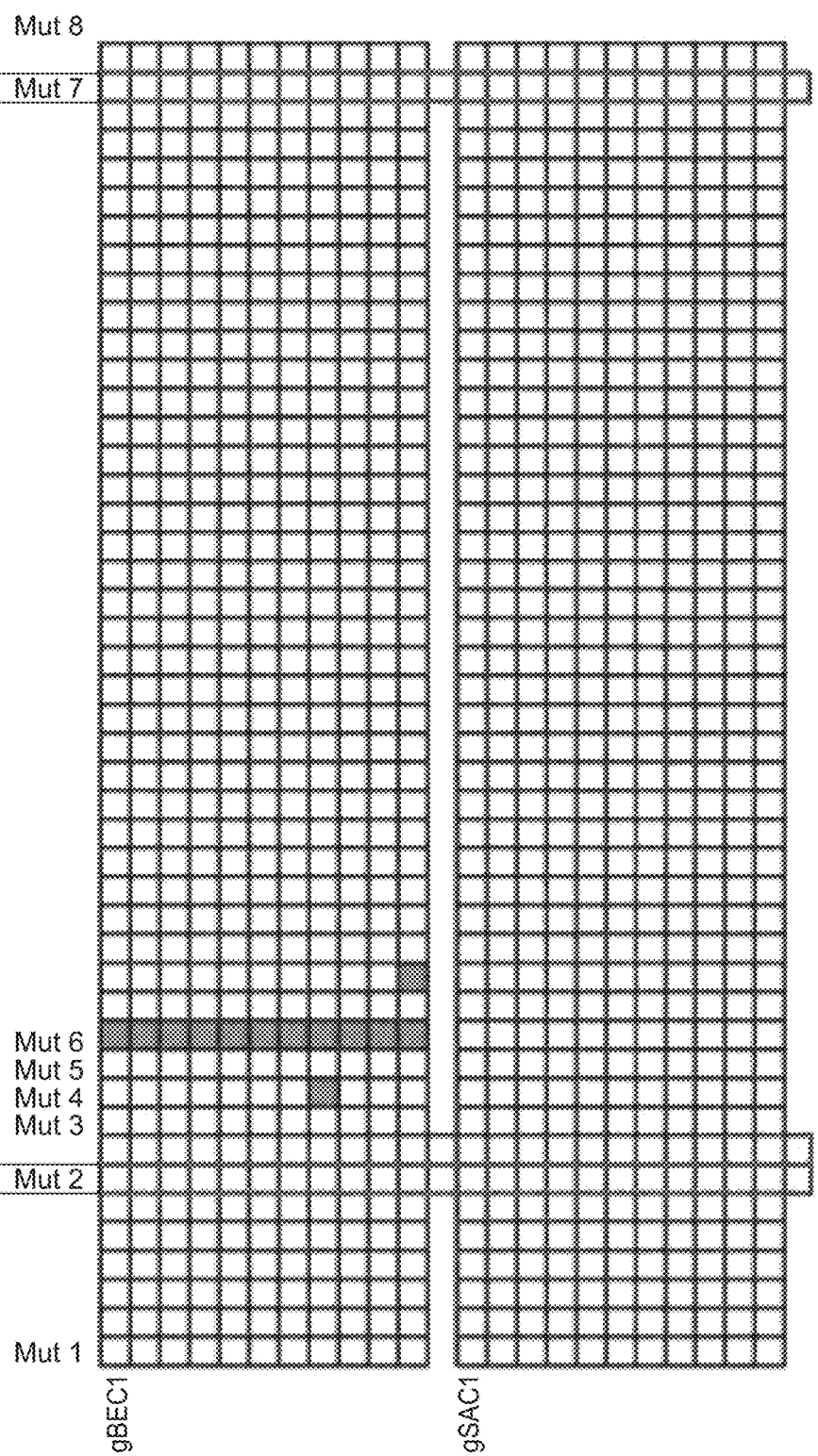

SEQUENCE LISTING

```
<160> NUMBER OF SEQ ID NOS: 30

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asp or Gly

<400> SEQUENCE: 1

Gly Phe Thr Phe Ser Xaa Ser Trp Ile His
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Leu
<220> FEATURE:
<221> NAME/KEY: VARIANT
<222> LOCATION: 10
<223> OTHER INFORMATION: Xaa = Thr or Ser

<400> SEQUENCE: 2

Ala Trp Ile Xaa Pro Tyr Gly Gly Ser Xaa Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Arg His Trp Pro Gly Gly Phe Asp Tyr
1               5
```

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Trp Val Arg Gln Ala Pro Gly Lys Gly Leu Glu Trp Val
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Synthetic Construct

<400> SEQUENCE: 6

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Trp Gly Gln Gly Thr Leu Val Thr Val Ser Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Asp or Val
<220> FEATURE:
<221> NAME/KEY: VARIANT
<222> LOCATION: 6
<223> OTHER INFORMATION: Xaa = Val or Ile
<220> FEATURE:
<221> NAME/KEY: VARIANT
<222> LOCATION: 7
<223> OTHER INFORMATION: Xaa = Ser or Asn
<220> FEATURE:
<221> NAME/KEY: VARIANT

```
<222> LOCATION: 9
<223> OTHER INFORMATION: Xaa = Ala or Phe
<220> FEATURE:
<221> NAME/KEY: VARIANT
<222> LOCATION: 10
<223> OTHER INFORMATION: Xaa = Val or Leu

<400> SEQUENCE: 8

Arg Ala Ser Gln Xaa Xaa Xaa Thr Xaa Xaa Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Phe or Thr
<220> FEATURE:
<221> NAME/KEY: VARIANT
<222> LOCATION: 6
<223> OTHER INFORMATION: Xaa = Tyr or Ala

<400> SEQUENCE: 9

Ser Ala Ser Xaa Leu Xaa Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Tyr, Gly, Phe, or Ser
<220> FEATURE:
<221> NAME/KEY: VARIANT
<222> LOCATION: 4
<223> OTHER INFORMATION: Xaa = Leu, Tyr, Phe or Trp
<220> FEATURE:
<221> NAME/KEY: VARIANT
<222> LOCATION: 5
<223> OTHER INFORMATION: Xaa = Tyr, Asn, Ala, Thr, Gly, Phe or Ile
<220> FEATURE:
<221> NAME/KEY: VARIANT
<222> LOCATION: 6
<223> OTHER INFORMATION: Xaa = His, Val, Pro, Tyr or Ile
<220> FEATURE:
<221> NAME/KEY: VARIANT
<222> LOCATION: 8
<223> OTHER INFORMATION: Xaa = Ala, Trp, Arg, Pro or Thr

<400> SEQUENCE: 10

Gln Gln Xaa Xaa Xaa Xaa Pro Xaa Thr
1               5

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Asp Ile Gln Met Thr Gln Ser Pro Ser Ser Leu Ser Ala Ser Val Gly
1               5                   10                  15
```

Asp Arg Val Thr Ile Thr Cys
            20

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic Construct

<400> SEQUENCE: 14

Phe Gly Gln Gly Thr Lys Val Glu Ile Lys Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gly Phe Thr Phe Ser Asp Ser Trp Ile His
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Synthetic Construct

<400> SEQUENCE: 16

Ala Trp Ile Ser Pro Tyr Gly Gly Ser Thr Tyr Tyr Ala Asp Ser Val
1               5                   10                  15

Lys Gly

<210> SEQ ID NO 17
<211> LENGTH: 11
<212> TYPE: PRT
<213> ORGANISM: Artificial Sequence
<220> FEATURE:

```
<223> OTHER INFORMATION: Synthetic Construct

<400> SEQUENCE: 17

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
                20                  25                  30

Trp Ile His Trp Val Arg Gln Ala Pro Gly Lys Gly Leu Glu Trp Val
            35                  40                  45

Ala Trp Ile Ser Pro Tyr Gly Gly Ser Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105
```

```
<210> SEQ ID NO 22
<211> LENGTH: 5
<212> TYPE: DNA
<213> ORGANISM: Homo sapiens

<400> SEQUENCE: 22 gctcg                                                                    5

<210> SEQ ID NO 23
<211> LENGTH: 139
<212> TYPE: DNA
<213> ORGANISM: Homo sapiens

<400> SEQUENCE: 23
cacgggtcca agtccaccgc cagctgcttg ctagtaacat gacttgtgta agttatccca       60
gctgcagcat ctaagtaagt ctcttcctgc gctaagcagg tccaggatcc ctgaacggaa      120
tttatttgct ctgtccatt                                                   139

<210> SEQ ID NO 24
<211> LENGTH: 118
<212> TYPE: PRT
<213> ORGANISM: Artificial Sequence
<220> FEATURE:
<223> OTHER INFORMATION: Synthetic Construct

<400> SEQUENCE: 24
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```

```
<210> SEQ ID NO 25
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 25

Trp Gly Gln Gly Thr Leu Val Thr Val Ser Ser
1               5                   10

<210> SEQ ID NO 26
<211> LENGTH: 447
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
```

```
305                 310                 315                 320
Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
                435                 440                 445

<210> SEQ ID NO 27
<211> LENGTH: 214
<212> TYPE: PRT
<213> ORGANISM: Artificial Sequence
<220> FEATURE:
<223> OTHER INFORMATION: Synthetic Construct

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
                35                  40                  45

Tyr Ser Ala Ser Phe Leu Tyr Ser Gly Val Pro Ser Arg Phe Ser Gly
                50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210
```

-continued

<210> SEQ ID NO 28
<211> LENGTH: 122
<212> TYPE: PRT
<213> ORGANISM: Artificial Sequence
<220> FEATURE:
<223> OTHER INFORMATION: Synthetic Construct

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys
        115                 120
```

<210> SEQ ID NO 29
<211> LENGTH: 108
<212> TYPE: PRT
<213> ORGANISM: Artificial Sequence
<220> FEATURE:
<223> OTHER INFORMATION: Synthetic Construct

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105
```

<210> SEQ ID NO 30
<211> LENGTH: 1186
<212> TYPE: DNA
<213> ORGANISM: Homo sapiens

<400> SEQUENCE: 30

```
gctcgggatg ggaagttctt ttaatgacaa agcaaatgaa gtttcattat gtcgaggaac    60
tttgaggaag tcacagaatc cacgatttaa aaatatattt cctattatac acccatacac   120
acacacacac acctactttc tagaataaaa accaaagcca tatgggtctg ctgctgactt   180
tttatatgtt gtagagttat atcaagttat gtcaagatgt tcagtcacct tgaagaggct   240
```

```
tttatcagaa aggggacgc ctttctgata aaggttaagg ggtaacctta agctcttacc    300
cctctgaagg taaaatcaag gtgcgttcag atgttggctt gttgtaaatt tcttttttta    360
ttaataacat actaaatgtg gatttgcttt aatcttcgaa actcttcccg gtgaaaatct    420
catttacaag aaaactggac tgacatgttt cactttctgt ttcatttcta tacacagctt    480
tattcctagg acaccaacac tagataccta aactgaaagc ttccgccgat ttcaccgaag    540
gtcaggaaag tccaacgccc ggcaaactgg atttgctgcc ttgggcagag gtgggcggga    600
ccccgcctcc gggcctggcg caacgctgag cagctggcgc gtcccgcgcg gccccagttc    660
tgcgcagctt cccgaggctc cgcaccagcc gcgcttctgt ccgcctgcag gtagggagcg    720
ttgttcctcc gcgggtgccc acggcccagt atctctggct agctcgctgg gcactttagg    780
acggagggtc tctacaccct ttctttggga tggagagagg agaagggaaa gggaacgcga    840
tggtctaggg ggcagtagag ccaattacct gttggggtta ataagaacag gcaatgcatc    900
tggccttcct ccaggcgcga ttcagttttg ctctaaaaat aatttatacc tctaaaaata    960
aataagatag gtagtatagg ataggtagtc attcttatgc gactgtgtgt tcagaatata   1020
gctctgatgc taggctggag gtctggacac gggtccaagt ccaccgccag ctgcttgcta   1080
gtaacatgac ttgtgtaagt tatcccagct gcagcatcta agtaagtctc ttcctgcgct   1140
aagcaggtcc aggatccctg aacggaattt atttgctctg tccatt               1186
```

PD-L1 PROMOTER METHYLATION IN CANCER

CROSS-REFERENCE TO RELATED APPLICATIONS

This application is a continuation of PCT/US2016/034856, filed May 27, 2016, which claims the priority benefit of U.S. Provisional Application Ser. No. 62/168,668, filed May 29, 2015, the disclosures of each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 146392027001SEQLIST.txt, date recorded: Nov. 16, 2017, size: 19 KB).

FIELD OF INVENTION

The invention relates to methods of stratifying cancer patients for treatment with an anti-PD-L1 antibody by determining the methylation level at a region upstream of the PD-L1 promoter region and/or at one or more CpG sites in intron 1 of the PD-L1 in samples containing cancer cells from the patients.

BACKGROUND OF THE INVENTION

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

Anti-PD-L1 antibodies and their uses in treating malignancies have been described (see, e.g., Philips et al. (2015) Int Immunol 27, 39-461; Herbst et al. (2014) Nature 515, 563-567). Certain patients have primary resistance to immune-checkpoint inhibitors (see, e.g., Taube et al. (2012) Sci Transl Med. 4, 127; Sznol et al. (2014) Clin Cancer Res. 19, 1021-34; and Gajewski et al. (2011) Curr Opin Immunol. 23:286-92). Thus, there remains a need predicting cancer patients' responsiveness to anti-PD-L1 antibody therapy.

All references, publications, and patent applications disclosed herein are hereby incorporated by reference in their entirety

BRIEF SUMMARY OF THE INVENTION

In certain embodiments, the invention provides a method of treating or delaying progression of cancer in a subject comprising administering to the subject an effective amount of an anti-PD-L1 antibody, wherein treatment (or delaying progression) is based upon the subject having medium or low level of methylation at CpG1 in the PD-L1 promoter region and/or at one or more CpG sites in intron 1 of the PD-L1 gene in a sample containing cancer cells from the subject.

In certain embodiments, the invention provides a method of treating or delaying progression of cancer in a subject provided that the subject has been found to have medium or low level of methylation at CpG1 in the PD-L1 promoter region and/or at one or more CpG sites in intron 1 of the PD-L1 gene in a sample containing cancer cells from the subject, the method comprising administering an effective amount of an anti-PD-L1 antibody to the subject.

In certain embodiments, the invention provides a method of treating or delaying progression of cancer, comprising: (a) selecting a subject having cancer, wherein said subject has medium or low level of methylation at CpG1 in the PD-L1 promoter region and/or at one or more CpG sites in intron 1 of the PD-L1 gene in a sample containing cancer cells from the subject; and (b) administering to the subject thus selected an effective amount of an anti-PD-L1 antibody.

In certain embodiments, the invention provides a method of predicting whether a subject with cancer is likely respond to treatment with an anti-PD-L1 antibody comprising measuring methylation level at CpG1 in the PD-L1 promoter region and/or at one or more CpG sites in intron 1 of the PD-L1 gene in a sample containing cancer cells from the subject, wherein medium or low level of methylation at CpG1 in the PD-L1 promoter region or at one or more CpG sites in intron 1 of the PD-L1 gene in the sample indicates the subjects likely to respond to the treatment.

In certain embodiments, provided is a method of treating cancer in a subject comprising: (a) measuring methylation level at CpG1 in the PD-L1 promoter region and/or at one or more CpG sites in intron 1 of the PD-L1 gene in a sample containing cancer cells from the subject; and (b) administering an effective amount of an anti-PD-L1 antibody to the subject who has been determined to have a medium or low level of methylation at CpG1 in the PD-L1 promoter region or at one or more CpG sites in intron 1 of the PD-L1 gene.

In certain embodiments, the invention provides a method of identifying a subject with cancer likely to respond to anti-PD-L1 antibody treatment comprising: (a) assessing methylation at CpG1 in the PD-L1 promoter region and/or at one or more CpG sites in intron 1 of the PD-L1 gene in a sample containing cancer cells from the subject; and (b) identifying the subject having medium or low level of methylation at CpG1 in the PD-L1 promoter region and/or at one or more CpG sites in intron 1 of the PD-L1 gene in the sample.

In some embodiments according to (or as applied to) any of the embodiments above, the methods further comprise administering an effective amount of an anti-PD-L1 antibody to the subject. In some embodiments according to (or as applied to) any of the embodiments above, the subject has medium or low level of methylation at CpG1 in the PD-L1 promoter region and at one or more CpG sites in intron 1 of the PD-L1 gene. In some embodiments according to (or as applied to) any of the embodiments above, the methylation level is determined by bisulfite sequencing. In some embodiments according to (or as applied to) any of the embodiments above, the methylation level is determined by bisulfite next-generation sequencing. In some embodiments according to (or as applied to) any of the embodiments above, the methylation level is determined using a methylation chip array. In some embodiments according to (or as applied to) any of the embodiments above, the sample from the subject shows evidence of immune cell infiltration. In some embodiments according to (or as applied to) any of the embodiments above, evidence of immune cell infiltration is indicated by CD8+ lymphocytes detected via western blot, ELISA, flow cytometry, qPCR, qRT-PCR, transcriptome profiling, microarray analysis, or next generation sequencing.

In some embodiments according to (or as applied to) any of the embodiments above, a medium level of methylation as determined by bisulfite sequencing between about 20% and about 40% methylation. In some embodiments according to (or as applied to) any of the embodiments above, a low level of methylation as determined by bisulfite sequencing is less than about 20% methylation.

In some embodiments according to (or as applied to) any of the embodiments above, a medium level of methylation as determined by bisulfite next generation sequencing between about 5% and about 60% methylation. In some embodiments according to (or as applied to) any of the embodiments above, a low level of methylation as determined by bisulfite next generation sequencing is less than about 5% methylation.

In some embodiments according to (or as applied to) any of the embodiments above, a medium level of methylation as determined by methylation chip array is a beta value between about 0.2 and about 0.3. In some embodiments according to (or as applied to) any of the embodiments above, a low level of methylation as determined by as determined by methylation chip array is a beta value of less than about 0.2

In some embodiments according to (or as applied to) any of the embodiments above, the cancer is lung cancer, breast cancer, bladder cancer or melanoma. In some embodiments according to (or as applied to) any of the embodiments above, the cancer is lung cancer, and wherein the lung cancer is non-small cell lung cancer, lung squamous cell carcinoma, or lung adenocarcinoma.

In some embodiments according to (or as applied to) any of the embodiments above, the anti-PD-L1 antibody inhibits the binding of PD-L1 to PD-1. In some embodiments according to (or as applied to) any of the embodiments above, the anti-PD-L1 antibody inhibits the binding of PD-L1 to B7-1. In some embodiments according to (or as applied to) any of the embodiments above, the anti-PD-L1 antibody inhibits the binding of PD-L1 to both PD-1 and B7-1. In some embodiments according to (or as applied to) any of the embodiments above, the anti-PD-L1 antibody is a monoclonal antibody. In some embodiments according to (or as applied to) any of the embodiments above, the anti-PD-L1 antibody is an antibody fragment selected from the group consisting of Fab, Fab'-SH, Fv, scFv, and (Fab')$_2$ fragments. In some embodiments according to (or as applied to) any of the embodiments above, the anti-PD-L1 antibody is a humanized antibody or a human antibody. In some embodiments according to (or as applied to) any of the embodiments above, the anti-PD-L1 antibody is selected from the group consisting of: YW243.55.S70, MPDL3280A, MDX-1105, and MEDI4736. In some embodiments according to (or as applied to) any of the embodiments above, the anti-PD-L1 antibody comprises a heavy chain comprising HVR-H1 sequence of SEQ ID NO:15, HVR-H2 sequence of SEQ ID NO:16, and HVR-H3 sequence of SEQ ID NO:3; and a light chain comprising HVR-L1 sequence of SEQ ID NO:17, HVR-L2 sequence of SEQ ID NO:18, and HVR-L3 sequence of SEQ ID NO:19. In some embodiments according to (or as applied to) any of the embodiments above, the anti-PD-L1 antibody comprises a heavy chain variable region comprising the amino acid sequence of SEQ ID NO:24 and a light chain variable region comprising the amino acid sequence of SEQ ID NO:21.

In some embodiments, the invention provides an article of manufacture comprising, packaged together, a pharmaceutical composition comprising an anti-PD-L1 antibody and a pharmaceutically acceptable carrier and a label denoting that the anti-PD-L1 antibody or pharmaceutical composition is indicated for treating subjects with cancer having medium or low level of methylation at CpG1 in the PD-L1 promoter region and/or at one or more CpG sites in intron 1 of the PD-L1 gene in a sample containing cancer cells from the subject.

In some embodiments, the invention provides a kit comprising reagents for measuring methylation level at CpG1 in the PD-L1 promoter region and/or at one or more CpG sites in intron 1 of the PD-L1 gene in a sample containing cancer cells from the subject and instructions for classifying the subject as having medium or low methylation level at CpG1 in the PD-L1 promoter region and/or at one or more CpG sites in intron 1 of the PD-L1 gene. In some embodiments according to (or as applied to) any of the embodiments above, the kits or articles of manufacture further comprise an anti-PD-L1 antibody, and instructions for administering the anti-PD-L1 antibody to the subject if the subject has medium or low methylation level at CpG1 in the PD-L1 promoter region and/or at one or more CpG sites in intron 1 of the PD-L1 gene.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A-1D shows PD-L1 expression levels and PD-L1 promoter methylation heat maps for 91 non-small cell lung cancer (NSCLC) cell lines.

FIG. 5A1-5A3 shows a superimposition of bisulfite sequencing data onto maps of possible CpG methylation sites for peripheral blood mononuclear cell subsets.

FIG. 5B1-5B3 shows a superimposition of bisulfite sequencing data onto maps of possible CpG methylation sites for immortalized normal lung cell lines, and NSCLC lung cancer cell lines having high, medium, or low methylation levels in the PD-L1 promoter region.

DETAILED DESCRIPTION OF THE INVENTION

I. General Techniques

Figure 1B:
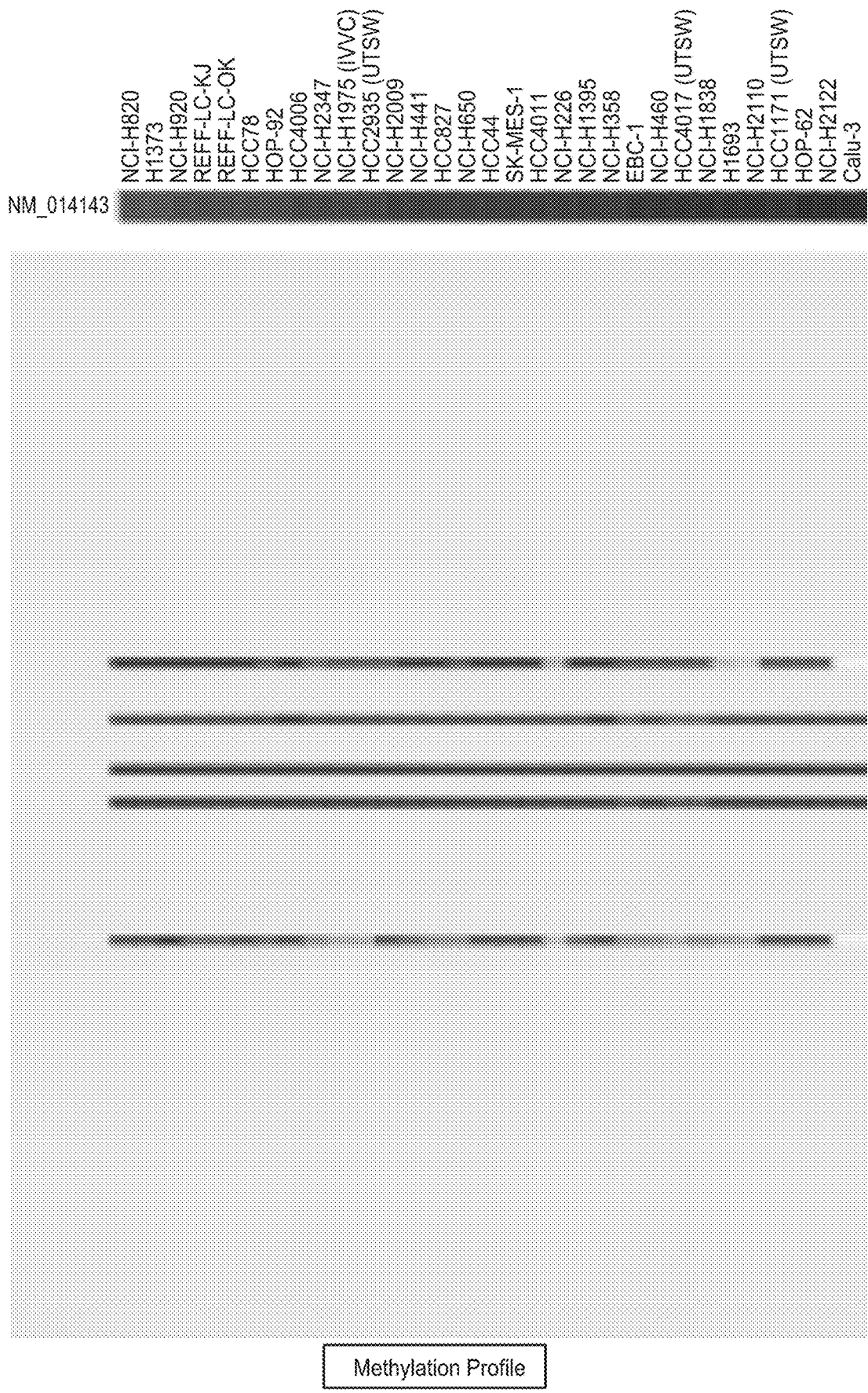
Figure 1C:
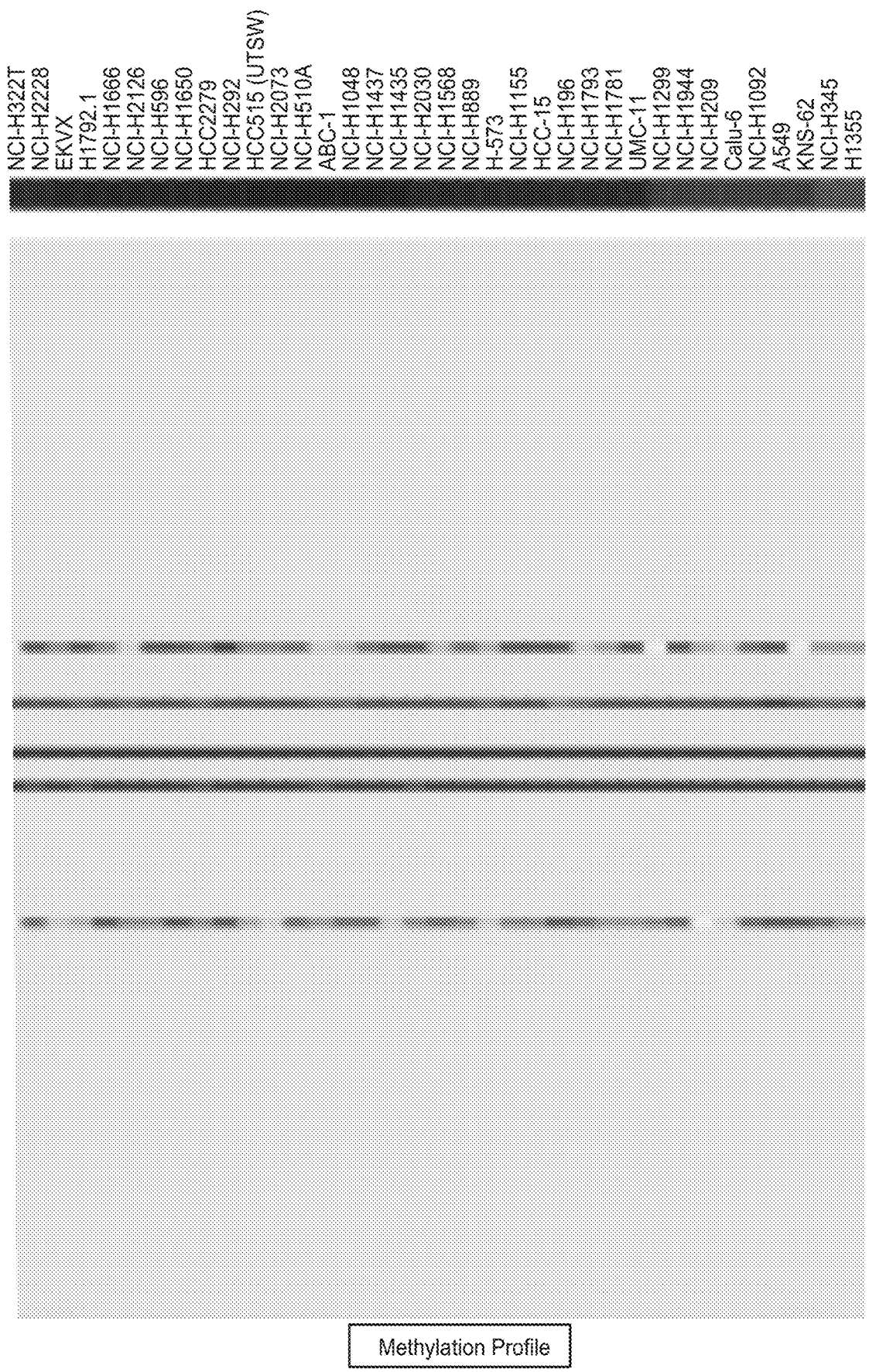
Figure 1D:
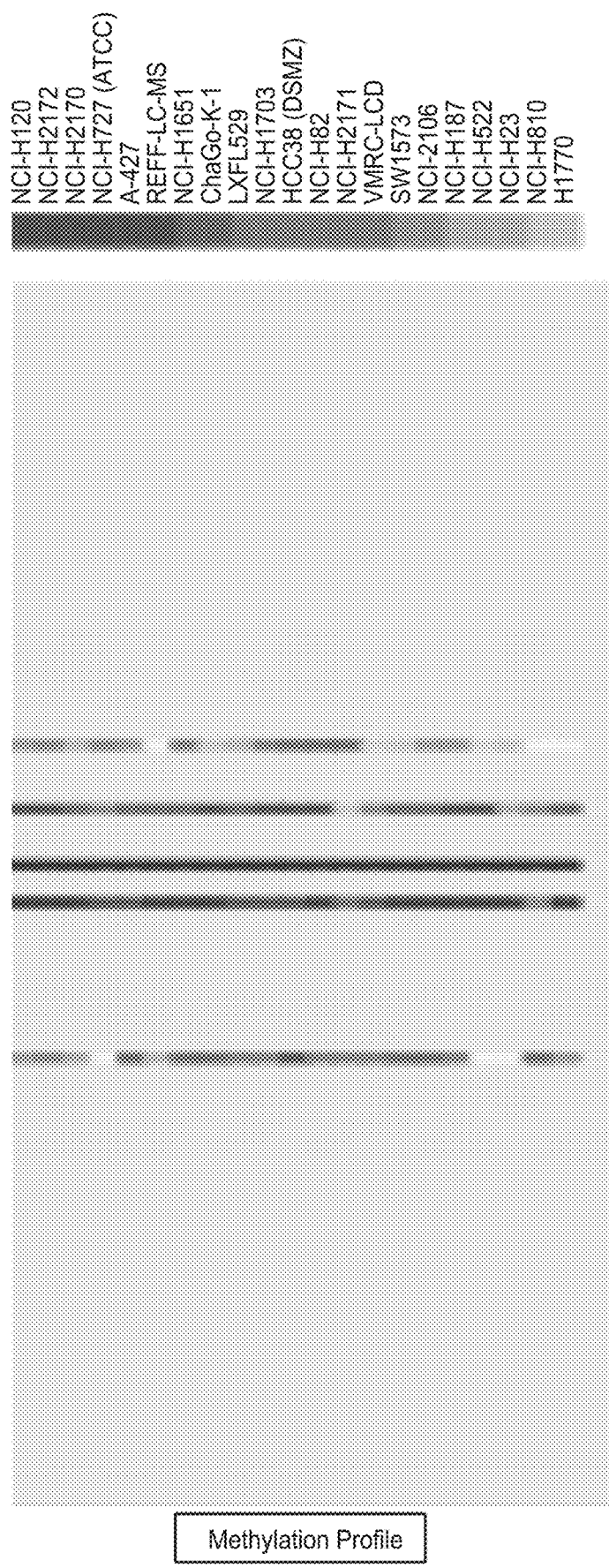
Figure 1E:
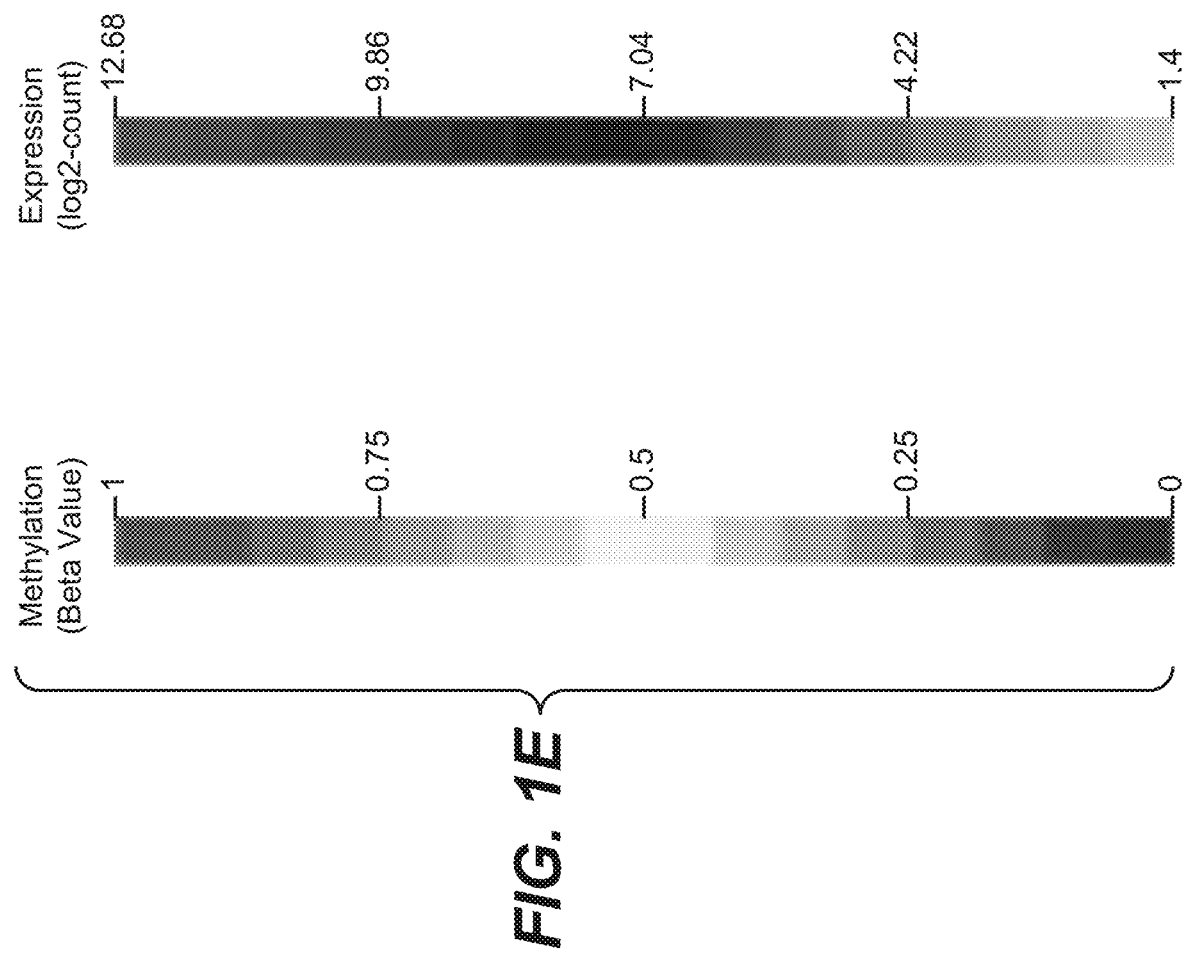

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, and/or prolonging survival of individuals.

As used herein, "based upon" includes (1) assessing, determining, or measuring the patient characteristics as described herein (and preferably selecting a patient suitable for receiving treatment; and (2) administering the treatment(s) as described herein.

A "subject," "patient," or an "individual" for purposes of treatment refers to any animal classified as a mammal, including humans, domestic and farm animals, and zoo, sports, or pet animals, such as dogs, horses, cats, cows, etc. Preferably, the mammal is human.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum amount required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The terms "cell proliferative disorder" and "proliferative disorder" refer to disorders that are associated with some degree of abnormal cell proliferation. In one embodiment, the cell proliferative disorder is cancer. In one embodiment, the cell proliferative disorder is a tumor.

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include but are not limited to, carcinoma, lymphoma, blastoma, sarcoma, leukemia or a lymphoid malignancy, squamous cell cancer (e.g., epithelial squamous cell cancer), cancer of the peritoneum, hepatocellular cancer, gastric or stomach cancer (such as gastrointestinal cancer and gastrointestinal stromal cancer), pancreatic cancer, glioblastoma, cervical cancer, ovarian cancer, liver cancer, bladder cancer, cancer of the urinary tract, hepatoma, colon cancer, rectal cancer, colorectal cancer (CRC), endometrial or uterine carcinoma, salivary gland carcinoma, kidney or renal cancer, prostate cancer, vulval cancer, thyroid cancer, hepatic carcinoma, anal carcinoma, penile carcinoma, multiple myeloma and B-cell lymphoma (such as low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia), chronic lymphocytic leukemia (CLL), acute lymphoblastic leukemia (ALL), hairy cell leukemia, chronic myeloblastic leukemia, and post-transplant lymphoproliferative disorder (PTLD), as well as abnormal vascular proliferation associated with phakomatoses, edema (such as that associated with brain tumors), Meigs' syndrome, brain, as well as head and neck cancer, soft-tissue sarcoma, Kaposi's sarcoma, carcinoid carcinoma, and mesothelioma, glioblastoma, neuroblastomas, and associated metastases. Other examples of cancer include, but are not limited to, breast cancer (such as breast carcinoma), lung cancer (such as small cell lung cancer, non-small cell lung cancer, adenocarcinoma of the lung, and squamous cell carcinoma of the lung), and skin cancer (such as melanoma, superficial spreading melanoma, lentigo maligna melanoma, acral lentiginous melanomas, nodular melanomas, and skin carcinoma), including metastatic forms of those cancers.

"Sample" as used herein refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. A sample can be a biological sample (such as an ex vivo biological sample) of biological tissue or fluid that contains cancer cells and/or tumor cells from the subject from which nucleic acids (such as polynucleotides, e.g., genomic DNA and/or transcripts) and/or polypeptides can be isolated. Such samples are typically from a human subject, but include tissues isolated from other subjects (such any animal classified as a mammal, as described elsewhere herein). Samples may also include sections of tissues such as biopsy and autopsy samples, frozen sections taken for histologic purposes. Samples may include fresh samples from the subject or preserved tissue samples, such as a formalin-fixed paraffin-embedded (FFPE) samples. Samples also include explants and primary and/or transformed cell cultures derived from patient tissues.

By "tissue or cell sample" is meant a collection of similar cells obtained from a tissue of a subject or patient. The source of the tissue or cell sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from antimicrotubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signalling inhibitors, HDAC inhibitors, proteasome inhibitors, and inhibitors of cancer metabolism. In one embodiment the cytotoxic agent is a taxane. In one embodiment the taxane is paclitaxel or docetaxel. In one embodiment the cytotoxic agent is a platinum agent. In one embodiment the cytotoxic agent is an antagonist of EGFR. In one embodiment the antagonist of EGFR is N-(3-ethynylphenyl)-6,7-bis(2-methoxyethoxy)quinazolin-4-amine (e.g., erlotinib). In one embodiment the cytotoxic agent is a RAF inhibitor. In one embodiment, the RAF inhibitor is a BRAF and/or CRAF inhibitor. In one embodiment the RAF inhibitor is vemurafenib. In one embodiment the cytotoxic agent is a PI3K inhibitor.

"Chemotherapeutic agent" refers to a compound useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; platinum-based agents, etoposide (VP-16); ifosfamide; capecitabine; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in this definition are (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG$_1$ λ antibody genetically modified to recognize interleukin-12 p40 protein.

A "growth inhibitory agent" when used herein refers to a compound or composition which inhibits growth of a cell either in vitro or in vivo. In one embodiment, growth inhibitory agent is growth inhibitory antibody that prevents or reduces proliferation of a cell expressing an antigen to which the antibody binds. In another embodiment, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in Mendelsohn and Israel, eds., The Molecular Basis of Cancer, Chapter 1, entitled "Cell cycle regulation, oncogenes, and antineoplastic drugs" by Murakami et al. (W.B. Saunders, Philadelphia, 1995), e.g., p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The term "anti-PD-L1 antibody" as used herein refers to an antagonist antibody that decreases, blocks, inhibits, abrogates or interferes with signal transduction resulting from the interaction of PD-L1 with either one or more of its binding partners, such as PD-1, B7-1. In some embodiments, anti-PD-L1 antibody is an antibody that inhibits the binding of PD-L1 to its binding partners. In a specific aspect, the anti-PD-L1 antibody inhibits binding of PD-L1 to PD-1 and/or B7-1. In some embodiments, the anti-PD-L1 antibody includes antigen binding fragments thereof that decrease, block, inhibit, abrogate or interfere with signal transduction resulting from the interaction of PD-L1 with one or more of its binding partners, such as PD-1, B7-1. In one embodiment, an anti-PD-L1 antibody reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In one embodiment, an anti-PD-L1 antibody is YW243.55.570 described herein. In another embodiment, an anti-PD-L1 antibody is MDX-1105 described herein. In another embodiment, an anti-PD-L1 antibody is MPDL3280A described herein. In another embodiment, an anti-PD-L1 antibody is MEDI4736 described herein.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. The anti-PD-L1 antibodies of the invention block the signaling through PD-1.

As use herein, the terms "binds", "specifically binds to" or "is specific for" refer to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

"Antibody fragments" comprise a portion of an intact antibody, preferably comprising the antigen binding region thereof. Examples of antibody fragments include Fab, Fab', F(ab')$_2$, and Fv fragments; diabodies; linear antibodies;

single-chain antibody molecules; and multispecific antibodies formed from antibody fragments.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. $F(ab')_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, antibodies can be assigned to different classes or isotypes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called α, δ, ε, γ, and μ respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact | |
|------|-------|-----|---------|---------|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat Numbering) |
| H1 | H31-H35 | H26-H35 | H26-H32 | H30-H35 | (Chothia Numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

A "naked antibody" is an antibody (as herein defined) that is not conjugated to a heterologous molecule, such as a cytotoxic moiety or radiolabel.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

III. Methods

In some embodiments, provided is a method of treating or delaying progression of cancer in a subject comprising administering to the subject an effective amount of an anti-PD-L1 antibody, wherein treatment is based upon the subject having medium or low level of methylation at CpG1 in the PD-L1 promoter region or at one or more CpG sites in intron 1 of the PD-L1 gene of the in a sample containing cancer cells from the subject.

In some embodiments, provided is a method of treating or delaying progression of cancer in a subject provided that the subject has been found to have medium or low level of methylation at CpG1 in the PD-L1 promoter region and/or at one or more CpG sites in intron 1 of the PD-L1 gene in a sample containing cancer cells from the subject, the method comprising administering an effective amount of an anti-PD-L1 antibody to the subject.

In some embodiments, provided is a method of treating or delaying progression of cancer, comprising: (a) selecting a subject having cancer, wherein said subject has medium or low level of methylation at CpG1 in the PD-L1 promoter region and/or at one or more CpG sites in intron 1 of the PD-L1 gene in a sample containing cancer cells from the subject; and (b) administering to the subject thus selected (e.g., selected in step (a)) an effective amount of an anti-PD-L1 antibody.

In some embodiments, provided is a method of predicting whether a subject with cancer is likely to respond to treatment with an anti-PD-L1 antibody, comprising measuring methylation level at CpG1 in the PD-L1 promoter region and/or at one or more CpG sites in intron 1 of the PD-L1 gene in a sample containing cancer cells from the subject, wherein medium or low level of methylation at CpG1 in the PD-L1 promoter region or at one or more CpG sites in intron 1 of the PD-L1 gene in the sample indicates the subject is likely to be responsive to the treatment.

In some embodiments, provided is a method of treating cancer in a subject comprising: (a) measuring methylation level at CpG1 in the PD-L1 promoter region and/or at one or more CpG sites in intron 1 of the PD-L1 gene in a sample containing cancer cells from the subject; and (b) administering an effective amount of an anti-PD-L1 antibody to the subject who has been determined to have a medium or low level of methylation at CpG1 in the PD-L1 promoter region or at one or more CpG sites in intron 1 of the PD-L1 gene.

In some embodiments, provided is a method of treating cancer in a subject comprising: (a) measuring methylation level at CpG1 in the PD-L1 promoter region and/or at one or more CpG sites in intron 1 of the PD-L1 gene in a sample containing cancer cells from the subject; and (b) administering an effective amount of an anti-PD-L1 antibody to the subject who has a medium or low level of methylation at CpG1 in the PD-L1 promoter region or at one or more CpG sites in intron 1 of the PD-L1 gene, as measured in step (a).

In some embodiments, provided is a method of treating cancer in a subject comprising measuring methylation level at CpG1 in the PD-L1 promoter region and/or at one or more CpG sites in intron 1 of the PD-L1 gene in a sample containing cancer cells from the subject; and if the subject has a medium or low level of methylation at CpG1 in the PD-L1 promoter region or at one or more CpG sites in intron 1 of the PD-L1 gene, administering an effective amount of an anti-PD-L1 antibody to the subject.

In some embodiments, provided is a method of identifying a subject with cancer likely to respond to anti-PD-L1 antibody treatment comprising: (a) assessing or measuring methylation level at CpG1 in the PD-L1 promoter region and/or at one or more CpG sites in intron 1 of the PD-L1 gene in a sample containing cancer cells from the subject; and (b) identifying the subject having medium or low level of methylation at CpG1 in the PD-L1 promoter region or at one or more CpG sites in intron 1 of the PD-L1 gene in a sample containing cancer cells from the subject. In some embodiments, the method further comprises administering an effective amount of an anti-PD-L1 antibody to the subject.

In certain embodiments, the methods provided herein comprise assessing methylation level at CpG1 in the PD-L1 promoter region and at one or more CpG sites in intron 1 of the PD-L1 gene.

The genomic coordinates of CpG1 (also referred to herein as Mut 2) in the PD-L1 promoter region are hg19 chr9: 5449887-5449891. The genomic coordinates for the one or more CpG sites in intron 1 of the PD-L1 gene (also referred to herein as CpG5 or Mut 7) are hg19 chr9:5450934-5451072. The sequences of these coordinates can be obtained at public online genomic databases, such as the UCSC Genome Browser (genome.ucsc.edu/).

```
                                              (SEQ ID NO: 22)
The nucleic acid sequence of CpG1 is GCTCG (SEQ ID NO: 23)
The nucleic acid sequence of CpG5 is CACGGGTCCAAGT

CCACCGCCAGCTGCTTGCTAGTAACATGACTTGTGTAAGTTATCCCAGCT

GCAGCATCTAAGTAAGTCTCTTCCTGCGCTAAGCAGGTCCAGGATCCCTG

AACGGAATTTATTTGCTCTGTCCATT

The sequence of hg19 chr9: 5449887-5451072 is provided below (CpG1 and CpG5 are underlined):
                                              (SEQ ID NO: 30)
GCTCGGGATGGGAAGTTCTTTTAATGACAAAGCAAATGAAGTTTCATTAT

GTCGAGGAACTTTGAGGAAGTCACAGAATCCACGATTTAAAAATATATTT
```

```
-continued
CCTATTATACACCCATACACACACACACACCTACTTTCTAGAATAAAA

ACCAAAGCCATATGGGTCTGCTGCTGACTTTTTATATGTTGTAGAGTTAT

ATCAAGTTATGTCAAGATGTTCAGTCACCTTGAAGAGGCTTTTATCAGAA

AGGGGGACGCCTTTCTGATAAAGGTTAAGGGGTAACCTTAAGCTCTTACC

CCTCTGAAGGTAAAATCAAGGTGCGTTCAGATGTTGGCTTGTTGTAAATT

TCTTTTTTTATTAATAACATACTAAATGTGGATTTGCTTTAATCTTCGAA

ACTCTTCCCGGTGAAAATCTCATTTACAAGAAAACTGGACTGACATGTTT

CACTTTCTGTTTCATTTCTATACACAGCTTTATTCCTAGGACACCAACAC

TAGATACCTAAACTGAAAGCTTCCGCCGATTTCACCGAAGGTCAGGAAAG

TCCAACGCCCGGCAAACTGGATTTGCTGCCTTGGGCAGAGGTGGGCGGGA

CCCCGCCTCCGGGCCTGGCGCAACGCTGAGCAGCTGGCGCGTCCCGCGCG

GCCCCAGTTCTGCGCAGCTTCCCGAGGCTCCGCACCAGCCGCGCTTCTGT

CCGCCTGCAGGTAGGGAGCGTTGTTCCTCCGCGGGTGCCCACGGCCCAGT

ATCTCTGGCTAGCTCGCTGGGCACTTTAGGACGGAGGGTCTCTACACCCT

TTCTTTGGGATGGAGAGAGGAGAAGGGAAAGGGAACGCGATGGTCTAGGG

GGCAGTAGAGCCAATTACCTGTTGGGGTTAATAAGAACAGGCAATGCATC

TGGCCTTCCTCCAGGCGCGATTCAGTTTTGCTCTAAAAATAATTTATACC

TCTAAAAATAAATAAGATAGGTAGTATAGGATAGGTAGTCATTCTTATGC

GACTGTGTGTTCAGAATATAGCTCTGATGCTAGGCTGGAGGTCTGGACAC

GGGTCCAAGTCCACCGCCAGCTGCTTGCTAGTAACATGACTTGTGTAAGT

TATCCCAGCTGCAGCATCTAAGTAAGTCTCTTCCTGCGCTAAGCAGGTCC

AGGATCCCTGAACGGAATTTATTTGCTCTGTCCATT
```

Methods of Determining Methylation Level

The degree of methylation at CpG1 in the PD-L1 promoter region and/or at one or more CpG sites in intron 1 of the PD-L1 can be measured using a variety of methods. In certain embodiments, the degree of methylation at CpG1 in the PD-L1 promoter region or at one or more CpG sites in intron 1 of the PD-L1 is determined by bisulfite DNA sequencing. Treatment of DNA with bisulfite converts cytosine ("C") residues to uracil ("U"), but leaves 5-methylcytosine residues unaffected. Thus, bisulfite treatment introduces specific changes in the DNA sequence that depend on the methylation status of individual cytosine residues, yielding single-nucleotide resolution information about the methylation status of a segment of DNA. Various analyses can be performed on the altered sequence to retrieve this information. In come embodiments, a bisulfite-modified sequence of interest (such as CpG1 in the PD-L1 promoter region and/or at one or more CpG sites in intron 1 of the PD-L1) is then amplified by PCR with two sets of strand-specific primers to yield a pair of fragments, one from each strand, in which all uracil and thymine residues are amplified as thymine and only 5-methylcytosine residues are amplified as cytosine. The PCR products can be sequenced directly or can be cloned and sequenced to provide methylation maps of single DNA molecules (see, e.g., Frommer, et al., *Proc. Natl. Acad. Sci.* 89: 1827-1831, 1992).

In some embodiments a low level of methylation as determined by bisulfite sequencing is less than about 20% methylation at CpG1 (such as about any one of 19%, 18%, 17%, 16%, 15%, 14%, 13%, 12%, 11%, 10%, 9%, 8%, 7%, 6%, 5%, 4%, 3%, 2%, 1%, or less than about 1% methylation, including any range in between these values). In some embodiments, a low level of methylation as determined by bisulfite sequencing is less than about 20% methylation at one or more CpG sites in intron 1 of the PD-L1 gene (such as about any one of 19%, 18%, 17%, 16%, 15%, 14%, 13%, 12%, 11%, 10%, 9%, 8%, 7%, 6%, 5%, 4%, 3%, 2%, 1%, or less than about 1% methylation, including any range in between these values). In some embodiments a low level of methylation as determined by bisulfite sequencing is less than about 20% methylation at CpG1 (such as about any one of 19%, 18%, 17%, 16%, 15%, 14%, 13%, 12%, 11%, 10%, 9%, 8%, 7%, 6%, 5%, 4%, 3%, 2%, 1%, or less than about 1% methylation, including any range in between these values) and less than about 20% methylation at one or more CpG sites in intron 1 of the PD-L1 gene (such as about any one of 19%, 18%, 17%, 16%, 15%, 14%, 13%, 12%, 11%, 10%, 9%, 8%, 7%, 6%, 5%, 4%, 3%, 2%, 1%, or less than about 1% methylation, including any range in between these values).

In some embodiments, a medium level of methylation as determined by bisulfite sequencing is between about 20% and about 40% methylation at CpG1 (such as about any one of 20%, 21%, 22%, 23%, 24%, 25%, 26%, 27%, 28%, 29%, 30%, 31%, 32%, 33%, 34%, 35%, 36%, 37%, 38%, 39%, or 40%, including any range in between these values). In some embodiments a medium level of methylation as determined by bisulfite sequencing, is between about 20% and about 40% methylation at one or more CpG sites in intron 1 of the PD-L1 gene (such as about any one of 20%, 21%, 22%, 23%, 24%, 25%, 26%, 27%, 28%, 29%, 30%, 31%, 32%, 33%, 34%, 35%, 36%, 37%, 38%, 39%, or 40%, including any range in between these values). In some embodiments, a medium level of methylation as determined by bisulfite sequencing is between about 20% and about 40% methylation at CpG1 (such as about any one of 20%, 21%, 22%, 23%, 24%, 25%, 26%, 27%, 28%, 29%, 30%, 31%, 32%, 33%, 34%, 35%, 36%, 37%, 38%, 39%, or 40%, including any range in between these values), and between about 20% and about 40% methylation at one or more CpG sites in intron 1 of the PD-L1 gene (such as about any one of 20%, 21%, 22%, 23%, 24%, 25%, 26%, 27%, 28%, 29%, 30%, 31%, 32%, 33%, 34%, 35%, 36%, 37%, 38%, 39%, or 40%, including any range in between these values).

In some embodiments, a high level of methylation as determined by bisulfite sequencing is between greater than about 40% and about 100% methylation at CpG1 (such about any one of 40%, 45%, 50%, 55%, 60%, 65%, 70%, 75%, 80%, 85%, 90%, 95%, 99%, or 100% methylation, including any range in between these values). In some embodiments, a high level of methylation as determined by bisulfite sequencing is between greater than about 40% and about 100% methylation at one or more CpG sites in intron 1 of the PD-L1 gene (such about any one of 40%, 45%, 50%, 55%, 60%, 65%, 70%, 75%, 80%, 85%, 90%, 95%, 99%, or 100% methylation, including any range in between these values) In some embodiments, a high level of methylation as determined by bisulfite sequencing is between greater than about 40% and about 100% methylation at CpG1 (such about any one of 40%, 45%, 50%, 55%, 60%, 65%, 70%, 75%, 80%, 85%, 90%, 95%, 99%, or 100% methylation, including any range in between these values), and between greater than about 40% and about 100% methylation at one or more CpG sites in intron 1 of the PD-L1 gene (such about any one of 40%, 45%, 50%, 55%, 60%, 65%, 70%, 75%, 80%, 85%, 90%, 95%, 99%, or 100% methylation, including any range in between these values).

In certain embodiments, the degree of methylation at CpG1 in the PD-L1 promoter region and/or at one or more CpG sites in intron 1 of the PD-L1 is determined by bisulfite next generation sequencing (BS-NGS), in which bisulfite-treated DNA is analyzed using a high-throughput next-generation sequencing system, such as the ILLUMINA® HI SEQ™ sequencing system. For additional details regarding bisulfite next generation sequencing see, e.g., Farlik et al. (2015) *Cell Reports* doi:10.1016/j.celrep.2015.02.001; Tiedemann et al. (2014) *Cell Reports*. doi:10.1016/j.celrep.2014.10.013; Fernandez et al. (2015) *Genome Research*. doi:10.1101/gr.169011.113; Lim et al. (2014) *PLOS Genetics*. doi:10.1371/journal.pgen.1004792.

In some embodiments, a low level of methylation as determined by bisulfite next generation sequencing is less than about 5% methylation at CpG1 (such as about 4%, about 3%, about 2%, about 1%, or less than about 1% methylation, including any range in between these values). In some embodiments, a low level of methylation as determined by bisulfite next generation sequencing is less than about 5% methylation at one or more CpG sites in intron 1 of the PD-L1 gene (such as about 4%, about 3%, about 2%, about 1%, or less than about 1% methylation, including any range in between these values). In some embodiments, a low level of methylation as determined by bisulfite next generation sequencing is less than about 5% methylation at CpG1 (such as about 4%, about 3%, about 2%, about 1%, or less than about 1% methylation, including any range in between these values) and less than about 5% methylation at one or more CpG sites in intron 1 of the PD-L1 gene (such as about 4%, about 3%, about 2%, about 1%, or less than about 1% methylation, including any range in between these values).

In some embodiments, a medium level of methylation as determined by bisulfite next generation sequencing is between about 5% and about 60% methylation at CpG1 (such as about any one of 5%, 10%, 15%, 20%, 25%, 30%, 35%, 40%, 45%, 50%, 55%, or less than about 60% methylation, including any range in between these values). In some embodiments, a medium level of methylation as determined by bisulfite next generation sequencing is between about 5% and about 60% methylation at one or more CpG sites in intron 1 of the PD-L1 gene (such as about any one of 5%, 10%, 15%, 20%, 25%, 30%, 35%, 40%, 45%, 50%, 55%, or less than about 60% methylation, including any range in between these values). In some embodiments, a medium level of methylation as determined by bisulfite next generation sequencing is between about 5% and about 60% methylation at CpG1 (such as about 5%, about 10%, about 15%, about 20%, about 25%, about 30%, about 35%, about 40%, about 45%, about 50%, about 55%, or less than about 60% methylation, including any range in between these values), and between about 5% and about 60% methylation at one or more CpG sites in intron 1 of the PD-L1 gene (such as about any one of 5%, 10%, 15%, 20%, 25%, 30%, 35%, 40%, 45%, 50%, 55%, or less than about 60% methylation, including any range in between these values).

In some embodiments, a high level of methylation as determined by bisulfite next generation sequencing is between about 60% and about 100% methylation at CpG1 (such about any one of 60%, 65%, 70%, 75%, 80%, 85%, 90%, 95%, 99%, more than about 99%, or about 100% methylation, including any range in between these values). In some embodiments, a high level of methylation as determined by bisulfite next generation sequencing is between about 60% and about 100% methylation at one or more CpG sites in intron 1 of the PD-L1 gene (such about any one of 60%, 65%, 70%, 75%, 80%, 85%, 90%, 95%, 99%, more than about 99%, or about 100% methylation, including any range in between these values). In some embodiments, a high level of methylation as determined by bisulfite next generation sequencing is between about 60% and about 100% methylation at CpG1 (such about 60%, more than about 60%, about 65%, about 70%, about 75%, about 80%, about 85%, about 90%, about 95%, about 99%, more than about 99%, or about 100% methylation, including any range in between these values), and between about 60% and about 100% methylation at one or more CpG sites in intron 1 of the PD-L1 gene (such about any one of 60%, 65%, 70%, 75%, 80%, 85%, 90%, 95%, 99%, more than about 99%, or about 100% methylation, including any range in between these values).

In certain embodiments, the degree of methylation at CpG1 in the PD-L1 promoter region and/or at one or more CpG sites in intron 1 of the PD-L1 is determined using a methylation chip array, such as the INFINIUM® HumanMethylation450 BeadChip array from ILLUMINA®. Briefly, following treatment with bisulfite, genomic DNA is whole-genome amplified (WGA), enzymatically fragmented, purified and added to the HumanMethylation450 BeadChips, which containing 485,512 probes covering 99% of RefSeq genes. The probes interrogate 19,755 unique CpG islands with additional coverage in shore regions and miRNA promoters as well as 3091 probes at non-CpG sites. During hybridization, the bisulfite-treated WGA-DNA molecules anneal to locus-specific FNA oligomers linked to individual bead types. The two bead types correspond to each CpG locus, i.e., one to the methylated ("C") and the other to the unmethylated ("T") stated. Allele-specific primers annealing is followed by single-base extension using DNP- and biotin-labeled ddNTPs. Both bead types for the same CpG locus will incorporate the same type of labeled nucleotide, determined by the base preceding the interrogated "C" in the CpG locus, and will therefore be detected in the same color channel. After extension, the array is fluorescently stained, scanned, and the intensities of the signals produced by the unmethylated and methylated bead types are measured. Software is used to record DNA methylation values, described as "beta values," for each locus in each sample. DNA methylation beta values are continuous variables between 0 and 1, representing the ratio of the intensity of the methylated bead type to the combined locus intensity. Further details describing the INFINIUM® HumanMethylation450 BeadChip array and assay platform are described in, e.g., Morris et al. (2015) *Methods* 72, 3-8; Sandoval et al. (2011) Epigenetics 6, 692-702; de Ruijter et al. (2015) *Laboratory Investigation* doi:10.1038/labinvest.2015.53; Lehne et al. (2015) *Genome Biology* 16, 37-49; and elsewhere.

In some embodiments, a low level of methylation as determined using a methylation chip array (such as the INFINIUM® HumanMethylation450 BeadChip array) is a beta value between about 0 and less than about 0.2 for CpG1 (such as about any one of 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, and 0.19 including any range in between these values). In some embodiments, a low level of methylation as determined using a methylation chip array (such as the INFINIUM® HumanMethylation450 BeadChip array) is a beta value between about 0 and less than about 0.2 for one or more CpG sites in intron 1 of the PD-L1 gene (such as about any one of 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, and 0.19 including any range in between these values). In some embodiments, a low level of methylation as determined using a methylation chip array (such as the INFINIUM® HumanMethylation450 BeadChip array) is a beta value between about 0 and about less than about 0.2 for CpG1 (such as about any one of 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, and 0.19 including any range in between these values) and a beta value between about 0 and less than about 0.2 for one or more CpG sites in intron 1 of the PD-L1 gene (such as about any one of 0, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, and 0.19 including any range in between these values).

In some embodiments, a medium level of methylation as determined using a methylation chip array (such as the INFINIUM® HumanMethylation450 BeadChip array) is a beta value between about 0.2 and about 0.3 for CpG1 (such as about any one of 0.2, 0.21, 0.22, 0.23, 0.24, 0.25, 0.26, 0.27, 0.28, or 0.29, including any range in between these values). In some embodiments, a medium level of methylation as determined using a methylation chip array (such as the INFINIUM® HumanMethylation450 BeadChip array) is a beta value between about 0.2 and about 0.3 for one or more CpG sites in intron 1 of the PD-L1 gene (such as about any one of 0.2, 0.21, 0.22, 0.23, 0.24, 0.25, 0.26, 0.27, 0.28, or 0.29, including any range in between these values). In some embodiments, a medium level of methylation as determined using a methylation chip array (such as the INFINIUM® HumanMethylation450 BeadChip array) is a beta value between about 0.2 and about 0.3 for CpG1 (such as about any one of 0.2, 0.21, 0.22, 0.23, 0.24, 0.25, 0.26, 0.27, 0.28, or 0.29, including any range in between these values) and a beta value between about 0.2 and about 0.3 for one or more CpG sites in intron 1 of the PD-L1 gene (such as about any one of 0.2, 0.21, 0.22, 0.23, 0.24, 0.25, 0.26, 0.27, 0.28, or 0.29, including any range in between these values).

In some embodiments, a high level of methylation as determined u using a methylation chip array (such as the INFINIUM® HumanMethylation450 BeadChip array) is a beta value between greater than about 0.3 and about 1.0 for CpG1 (such as about any one of greater than 0.3, 0.35, 0.4, 0.45, 0.5, 0.55, 0.6, 0.65, 0.7, 0.75, 0.8, 0.85, 0.9, 0.95, or 1.0, including any range in between these values). In some embodiments a high level of methylation as determined using a methylation chip array (such as the INFINIUM® HumanMethylation450 BeadChip array) is a beta value between greater than about 0.3 and about 1.0 for one or more CpG sites in intron 1 of the PD-L1 gene (such as about any one of greater than 0.3, 0.35, 0.4, 0.45, 0.5, 0.55, 0.6, 0.65, 0.7, 0.75, 0.8, 0.85, 0.9, 0.95, or 1.0, including any range in between these values). In some embodiments, a high level of methylation as determined using a methylation chip array (such as the INFINIUM® HumanMethylation450 BeadChip array) is beta value between greater than about 0.3 and about 1.0 for CpG1 (such as about any one of greater than 0.3, 0.35, 0.4, 0.45, 0.5, 0.55, 0.6, 0.65, 0.7, 0.75, 0.8, 0.85, 0.9, 0.95, or 1.0, including any range in between these values) and a beta value between greater than about 0.3 and about 1.0 for one or more CpG sites in intron 1 of the PD-L1 gene (such as about any one of greater than 0.3, 0.35, 0.4, 0.45, 0.5, 0.55, 0.6, 0.65, 0.7, 0.75, 0.8, 0.85, 0.9, 0.95, or 1.0, including any range in between these values).

In some embodiments, the sample from the subject is a biological sample (such as an ex vivo biological sample) of biological tissue or fluid that contains cancer cells and/or tumor cells from the subject from which nucleic acids (such as polynucleotides, e.g., genomic DNA and/or transcripts) and/or polypeptides can be isolated. In some embodiments, the sample comprises frozen sections of tissue, such as those taken for histological purposes. In some embodiments, the sample is a taken from a biopsy. In some embodiments, the sample is taken from an autopsy. In some embodiments, the sample is a frozen tissue sample. In some embodiments, the sample is a fresh sample taken from the subject. In some embodiments, the sample is a preserved tissue sample. In some embodiments, the sample is a formalin-fixed paraffin-embedded (FFPE) samples. In some embodiments, the sample is an explant or a primary and/or transformed cell culture derived from tissue from the subject.

In some embodiments of any of the methods described herein, the sample containing cancer cells from the subject further shows evidence of immune cell infiltration. In certain embodiments, the presence of any one or more of $CD16^+$, $CD4^+$, $CD3^+$, $CD56^+$, $CD45^+$, $CD68^+$, $CD20^+$, $CD163^+$, or $CD8^+$ lymphocytes in a sample containing cancer cells from the subject indicates of immune cell infiltration In certain embodiments, the presence of $CD8^+$ lymphocytes in a sample containing cancer cells from the subject indicates of immune cell infiltration. In certain embodiments the presence of one or more of $CD16^+$, $CD4^+$, $CD3^+$, $CD56^+$, $CD45^+$, $CD68^+$, $CD20^+$, $CD163^+$, or $CD8^+$ lymphocytes in a sample containing cancer cells from the subject is detected using immunohistochemical (IHC) assays well known and widely used by those of ordinary skill in the art. Such methods include, but are not limited to, e.g., western blot, ELISA, and flow cytometry. In certain embodiments the presence of one or more of $CD16^+$, $CD4^+$, $CD3^+$, $CD56^+$, $CD45^+$, $CD68^+$, $CD20^+$, $CD163^+$, or $CD8^+$ lymphocytes in a sample containing cancer cells from the subject is detected using gene expression analysis techniques, including, but not limited to quantitative PCR (qPCR), qRT-PCR, transcriptome profiling (such as RNAseq), microarray analyses, next generation sequencing, etc. Such services are provided by, e.g., FLUIDIGM®, NANOSTRING TECHNOLOGIES®, etc.

In certain embodiments, the subject is not treated with an anti-PD-L1 antibody if the sample containing cancer cells from the subject has medium level of methylation at CpG1 in the PD-L1 promoter region and/or one or more CpG sites in intron 1 of the PD-L1 gene and no evidence of immune cell infiltration. In certain embodiments, the subject is treated with an anti-PD-L1 antibody if the sample containing cancer cells from the subject has medium level of methylation at CpG1 in the PD-L1 promoter region and/or one or more CpG sites in intron 1 of the PD-L1 gene and evidence of immune cell infiltration.

Cancer

In some embodiments of any of the methods described herein, the cancer is carcinoma, lymphoma, blastoma, sarcoma, leukemia or a lymphoid malignancy. In some embodiments of any of the methods described herein, the cancer is carcinoma, lymphoma, blastoma, sarcoma, leukemia or a lymphoid malignancy. In some embodiments, the cancer is squamous cell cancer (e.g., epithelial squamous cell cancer), cancer of the peritoneum, hepatocellular cancer, gastric or stomach cancer (such as gastrointestinal cancer and gastrointestinal stromal cancer), pancreatic cancer, glioblastoma, cervical cancer, ovarian cancer, liver cancer, bladder cancer, cancer of the urinary tract, hepatoma, colon cancer, rectal cancer, colorectal cancer (CRC), endometrial or uterine carcinoma, salivary gland carcinoma, kidney or renal cancer, prostate cancer, vulval cancer, thyroid cancer, hepatic carcinoma, anal carcinoma, penile carcinoma, multiple myeloma and B-cell lymphoma (such as low grade/follicular non-Hodgkin's lymphoma (NHL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, mantle cell lymphoma, AIDS-related lymphoma, and Waldenstrom's Macroglobulinemia), chronic lymphocytic leukemia (CLL), acute lymphoblastic leukemia (ALL), hairy cell leukemia, chronic myeloblastic leukemia, and post-transplant lymphoproliferative disorder (PTLD), as well as abnormal vascular proliferation associated with phakomatoses, edema (such as that associated with brain tumors), Meigs' syndrome, brain, as well as head and neck cancer, soft-tissue sarcoma, Kaposi's sarcoma, carcinoid carcinoma, and mesothelioma, glioblastoma, neuroblastomas, and associated metastases.

In certain embodiments, cancers that are amenable to treatment by the methods of the invention include breast cancer, lung cancer, and skin cancer, including metastatic forms of those cancers. In certain embodiments, the breast cancer is breast carcinoma. In some embodiments, lung cancer is small cell lung cancer, non-small cell lung cancer, adenocarcinoma of the lung, or squamous cell carcinoma of the lung. In certain embodiments, the skin cancer is melanoma, superficial spreading melanoma, lentigo maligna melanoma, acral lentiginous melanomas, nodular melanomas, skin carcinoma, or bladder cancer.

Anti-PD-L1 Antibodies

PD-L1 (also known as "programmed death-ligand 1," PDCD1L1, PDCD1LG1, B7-H1, B7-H, and CD274) is a 40 kDa type 1 transmembrane protein that binds PD-1, a receptor found on activated T cells, B cells, and myeloid cells. Engagement of PD-L1 with PD-1 delivers a signal that inhibits TCR-mediated activation of IL-2 production and T cell proliferation. The PD-L1/PD-1 pathway is implicated as a major mechanism by which tumors evade elimination by the immune system (Lipson E J, et al. Cancer Immunol Res 2013; 1(1):54-63). Without being bound by theory, the inhibition of PD-L1 by an anti-PD-L1 antibody may permit the activation of T cells, thus restoring their ability to effectively detect and attack cancer cells and tumor cells.

In certain embodiments of any one of the methods provided herein, the anti-PD-L1 antibody (or antigen binding fragment thereof) inhibits the binding of PD-L1 to its binding partners. In a specific aspect, PD-L1 binding partners are PD-1 and/or B7-1. In certain embodiments, the anti-PD-L1 antibody (or antigen binding fragment thereof) is selected from the group consisting of YW243.55.S70, MPDL3280A, MDX-1105, MEDI4736, and MSB0010718C. MDX-1105, also known as BMS-936559, is an anti-PD-L1 antibody described in WO2007/005874. Antibody YW243.55.S70 (heavy and light chain variable region sequences shown in SEQ ID Nos. 20 and 21, respectively) is an anti-PD-L1 antibody described in WO 2010/077634 A1. MEDI4736 is an anti-PD-L1 antibody described in WO2011/066389 and US2013/034559.

Examples of anti-PD-L1 antibodies (or antigen binding fragments thereof) useful for the methods provided herein, and methods for making thereof are described in PCT patent application WO 2010/077634 A1 and U.S. Pat. No. 8,217,149, which are incorporated herein by reference.

In some embodiments, the anti-PD-L1 antibody (or antigen binding fragment thereof) is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments.

In some embodiments, the anti-PD-L1 antibody is a humanized antibody. In some embodiments, the anti-PD-L1 antibody is a human antibody.

In some embodiments, the anti-PD-L1 antibody comprises a heavy chain variable region comprising the amino acid sequence of SEQ ID NO:20 and a light chain variable region comprising the amino acid sequence of SEQ ID NO:21.

In one embodiment, the anti-PD-L1 antibody contains a heavy chain variable region polypeptide comprising an HVR-H1, HVR-H2 and HVR-H3 sequence, wherein:

(a) the HVR-H1 sequence is GFTFSX$_1$SWIH; (SEQ ID NO: 1)

(b) the HVR-H2 sequence is AWIX$_2$PYGGSX$_3$YYADSVKG; (SEQ ID NO: 2)

(c) the HVR-H3 sequence is RHWPGGFDY; (SEQ ID NO: 3)

further wherein: $X_1$ is D or G; $X_2$ is S or L; $X_3$ is T or S.

In one specific aspect, $X_1$ is D; $X_2$ is S and $X_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

HC-FR1 is EVQLVESGGGLVQPGGSLRLSCAAS (SEQ ID NO: 4)

HC-FR2 is WVRQAPGKGLEWV (SEQ ID NO: 5)

HC-FR3 is RFTISADTSKNTAYLQMNSLRAEDTAVYYCAR (SEQ ID NO: 6)

HC-FR4 is WGQGTLVTVSA. (SEQ ID NO: 7)

In a still further aspect, the heavy chain polypeptide is further combined with a variable region light chain comprising an HVR-L1, HVR-L2 and HVR-L3, wherein:

(a) the HVR-L1 sequence is RASQX$_4$X$_5$X$_6$TX$_7$X$_8$A; (SEQ ID NO: 8)

(b) the HVR-L2 sequence is SASX$_9$LX$_{10}$S,; (SEQ ID NO: 9)

(c) the HVR-L3 sequence is QQX$_{11}$X$_{12}$X$_{13}$X$_{14}$PX$_{15}$T; (SEQ ID NO: 10)

further wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
                                            (SEQ ID NO: 11)
    LC-FR1 is DIQMTQSPSSLSASVGDRVTITC (SEQ ID NO: 12)
    LC-FR2 is WYQQKPGKAPKLLIY (SEQ ID NO: 13)
    LC-FR3 is GVPSRFSGSGSGTDFTLTISSLQPEDFATYYC (SEQ ID NO: 14)
    LC-FR4 is FGQGTKVEIKR.
```

In another embodiment, provided is an isolated anti-PD-L1 antibody or antigen binding fragment comprising a heavy chain and a light chain variable region sequence, wherein:

the heavy chain comprises and HVR-H1, HVR-H2 and HVR-H3, wherein further:

```
                                            (SEQ ID NO: 1)
    (i) the HVR-H1 sequence is GFTFSX₁SWIH;

(SEQ ID NO: 2)
    (ii) the HVR-H2 sequence is AWIX₂PYGGSX₃YYADSVKG (SEQ ID NO: 3)
    (iii) the HVR-H3 sequence is RHWPGGFDY,
    and
``` the light chain comprises and HVR-L1, HVR-L2 and HVR-L3, wherein further:

```
                                            (SEQ ID NO: 8)
    (i) the HVR-L1 sequence is RASQX₄X₅X₆TX₇X₈A (SEQ ID NO: 9)
    (ii) the HVR-L2 sequence is SASX₉LX₁₀S;
    and (SEQ ID NO: 10)
    (iii) the HVR-L3 sequence is QQX₁₁X₁₂X₁₃X₁₄PX₁₅T;
```

Further wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                            (SEQ ID NO: 4)
    HC-FR1      EVQLVESGGGLVQPGGSLRLSCAAS (SEQ ID NO: 5)
    HC-FR2      WVRQAPGKGLEWV (SEQ ID NO: 6)
    HC-FR3      RFTISADTSKNTAYLQMNSLRAEDTAVYYCAR (SEQ ID NO: 7)
    HC-FR4      WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
                                            (SEQ ID NO: 11)
    LC-FR1      DIQMTQSPSSLSASVGDRVTITC (SEQ ID NO: 12)
    LC-FR2      WYQQKPGKAPKLLIY (SEQ ID NO: 13)
    LC-FR3      GVPSRFSGSGSGTDFTLTISSLQPEDFATYYC (SEQ ID NO: 14)
    LC-FR4      FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:

the heavy chain further comprises and HVR-H1, HVR-H2 and an HVR-H3 sequence having at least 85% sequence identity to GFTFSDSWIH (SEQ ID NO:15), AWISPYGG-STYYADSVKG (SEQ ID NO:16) and RHWPGGFDY (SEQ ID NO:3), respectively, or the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
                                            (SEQ ID NO: 4)
HC-FR1     EVQLVESGGGLVQPGGSLRLSCAAS (SEQ ID NO: 5)
HC-FR2     WVRQAPGKGLEWV (SEQ ID NO: 6)
HC-FR3     RFTISADTSKNTAYLQMNSLRAEDTAVYYCAR (SEQ ID NO: 7)
HC-FR4     WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
DIQMTQSPSSLSASVGDRVTITC                 (SEQ ID NO: 11)

LC-FR2
WYQQKPGKAPKLLIY                         (SEQ ID NO: 12)

LC-FR3
GVPSRFSGSGSGTDFTLTISSLQPEDFATYYC        (SEQ ID NO: 13)

LC-FR4
FGQGTKVEIKR.                            (SEQ ID NO: 14)
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:
(a) the heavy chain sequence has at least 85% sequence identity to the heavy chain sequence:

```
                                            (SEQ ID NO: 20)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA,
``` or
(b) the light chain sequences has at least 85% sequence identity to the light chain sequence:

```
                                            (SEQ ID NO: 21)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
EVQLVESGGGLVQPGGSLRLSCAAS               (SEQ ID NO: 4)

HC-FR2
WVRQAPGKGLEWV                           (SEQ ID NO: 5)

HC-FR3
RFTISADTSKNTAYLQMNSLRAEDTAVYYCAR        (SEQ ID NO: 6)

HC-FR4
WGQGTLVTVSA.                            (SEQ ID NO: 7)
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
DIQMTQSPSSLSASVGDRVTITC                 (SEQ ID NO: 11)

LC-FR2
WYQQKPGKAPKLLIY                         (SEQ ID NO: 12)

LC-FR3
GVPSRFSGSGSGTDFTLTISSLQPEDFATYYC        (SEQ ID NO: 13)

LC-FR4
FGQGTKVEIKR.                            (SEQ ID NO: 14)
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In another further embodiment, provided is an isolated anti-PD-L1 antibody comprising a heavy chain and a light chain variable region sequence, wherein:
(a) the heavy chain sequence has at least 85% sequence identity to the heavy chain sequence:

```
                                           (SEQ ID NO: 24)
EVQLVESGGGLVQPGGSLRLSCAASGFTFSDSWIHWVRQAPGKGLEWVA

WISPYGGSTYYADSVKGRFTISADTSKNTAYLQMNSLRAEDTAVYYCARR

HWPGGFDYWGQGTLVTVSS,
```
or
(b) the light chain sequences has at least 85% sequence identity to the light chain sequence:

```
                                           (SEQ ID NO: 21)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a still further embodiment, provided is an isolated anti-PDL1 antibody comprising a heavy chain and a light chain variable region sequence, wherein:
(a) the heavy chain sequence has at least 85% sequence identity to the heavy chain sequence:

```
                                           (SEQ ID NO: 28)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK,
```
or
(b) the light chain sequences has at least 85% sequence identity to the light chain sequence:

```
                                           (SEQ ID NO: 29)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework.

In a still further aspect, one or more of the heavy chain framework sequences is the following:

```
HC-FR1
EVQLVESGGGLVQPGGSLRLSCAAS              (SEQ ID NO: 4)

HC-FR2
WVRQAPGKGLEWV                          (SEQ ID NO: 5)

HC-FR3
RFTISADTSKNTAYLQMNSLRAEDTAVYYCAR       (SEQ ID NO: 6)

HC-FR4
WGQGTLVTVSS.                           (SEQ ID NO: 25)
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
DIQMTQSPSSLSASVGDRVTITC                (SEQ ID NO: 11)

LC-FR2
WYQQKPGKAPKLLIY                        (SEQ ID NO: 12)

LC-FR3
GVPSRFSGSGSGTDFTLTISSLQPEDFATYYC       (SEQ ID NO: 13)

LC-FR4
FGQGTKVEIKR.                           (SEQ ID NO: 14)
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, the anti-PD-1 antibody is MPDL3280A (CAS Registry Number: 1422185-06-5). In a still further embodiment, provided is an isolated anti-PD-1 antibody comprising a heavy chain variable region comprising the heavy chain variable region amino acid sequence from SEQ ID NO:24 and/or a light chain variable region comprising the light chain variable region amino acid sequence from SEQ ID NO:25. In a still further embodiment, provided is an isolated anti-PDL-1 antibody comprising a heavy chain and/or a light chain sequence, wherein:
(a) the heavy chain sequence has at least 85%, at least 90%, at least 91%, at least 92%, at least 93%, at least 94%, at least 95%, at least 96%, at least 97%, at least 98%, at least 99% or 100% sequence identity to the heavy chain sequence:

```
                                           (SEQ ID NO: 26)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH
```

```
WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG,
```
or
(b) the light chain sequences has at least 85%, at least 90%, at least 91%, at least 92%, at least 93%, at least 94%, at least 95%, at least 96%, at least 97%, at least 98%, at least 99% or 100% sequence identity to the light chain sequence:

```
                                          (SEQ ID NO: 27)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC.
```

In some embodiments, provided is an isolated nucleic acid encoding a light chain or a heavy chain variable region sequence of an anti-PD-L1 antibody, wherein:
(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and
(b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
EVQLVESGGGLVQPGGSLRLSCAAS            (SEQ ID NO: 4)

HC-FR2
WVRQAPGKGLEWV                        (SEQ ID NO: 5)

HC-FR3
RFTISADTSKNTAYLQMNSLRAEDTAVYYCAR     (SEQ ID NO: 6)

HC-FR4
WGQGTLVTVSA.                         (SEQ ID NO: 7)
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
DIQMTQSPSSLSASVGDRVTITC              (SEQ ID NO: 11)

LC-FR2
WYQQKPGKAPKLLIY                      (SEQ ID NO: 12)

LC-FR3
GVPSRFSGSGSGTDFTLTISSLQPEDFATYYC     (SEQ ID NO: 13)

LC-FR4
FGQGTKVEIKR.                         (SEQ ID NO: 14)
```

In a still further specific aspect, the anti-PD-L1 antibody described herein further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, provided herein are nucleic acids encoding any of the antibodies described herein. In some embodiments, the nucleic acid further comprises a vector suitable for expression of the nucleic acid encoding any of the anti-PD-L1 antibodies described herein. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

IV. Antibody Preparation

The methods, kits, and articles of manufacture provided herein use, or incorporate, an antibody that binds to PD-L1. Exemplary techniques for generating and producing such antibodies are described below.

Antigen Preparation

The soluble form of PD-L1 (such as the extracellular domain), or fragments thereof, optionally conjugated to other molecules, can be used as an immunogen for generating anti-PD-L1 antibodies and/or for screening anti-PD-L1 antibodies. Alternatively, cells expressing PD-L1 can be used as the immunogen or for screening. Such cells can be derived from a natural source (e.g. cancer cell lines) or may be cells which have been transformed by recombinant techniques to express the transmembrane molecule. Other forms of PD-L1 useful for preparing and/or screening anti-PD-L1 antibodies will be apparent to those in the art.

Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. In some embodiments, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., *Nature*, 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

Library-Derived Antibodies

Antibodies or antibody fragments can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Antibodies of the invention may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature,* 321:522-525 (1986); Riechmann et al., *Nature,* 332:323-327 (1988); Verhoeyen et al., *Science,* 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

The CDR sequences above are generally present within human variable light and variable heavy framework sequences, such as substantially the human consensus FR residues of human light chain kappa subgroup I ($V_L6$ I), and substantially the human consensus FR residues of human heavy chain subgroup III ($V_H$III). See also WO 2004/056312 (Lowman et al.).

In some embodiments, the variable heavy region may be joined to a human IgG chain constant region, wherein the region may be, for example, IgG1 or IgG3, including native sequence and variant constant regions.

In some embodiments, the antibody herein may further comprise at least one amino acid substitution in the Fc region that improves ADCC activity, such as one wherein the amino acid substitutions are at positions 298, 333, and 334, preferably S298A, E333A, and K334A, using EU numbering of heavy chain residues. See also U.S. Pat. No. 6,737,056B1, Presta. Any of these antibodies may comprise at least one substitution in the Fc region that improves FcRn binding or serum half-life, for example a substitution at heavy chain position 434, such as N434W. See also U.S. Pat. No. 6,737,056B1, Presta. Any of these antibodies may further comprise at least one amino acid substitution in the Fc region that increases CDC activity, for example, comprising at least a substitution at position 326, preferably K326A or K326W. See also U.S. Pat. No. 6,528,624B1 (Idusogie et al.).

Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); and U.S. Pat. Nos. 5,591,669, 5,589,369 and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229,275).

Antibody Fragments

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. The antibody fragment may also be a "linear antibody", e.g., as described in U.S. Pat. No. 5,641,870 for example. Such linear antibody fragments may be monospecific or bispecific.

Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J*, 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1

PROPERTIES OF AMINO ACID RESIDUES

| Amino acid | One-letter abbreviation | Mass[a] (daltons) | Volume[b] ($Å^3$) | Accessible surface area[c] ($Å^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43rd ed. Cleveland, Chemical Rubber Publishing Co., 1961.
[b]Values from A. A. Zamyatnin, Prog. Biophys. Mol. Biol. 24: 107-123, 1972.
[c]Values from C. Chothia, J. Mol. Biol. 105: 1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 2

EXEMPLARY SETS OF CORRESPONDING KNOB- AND HOLE-FORMING MUTATIONS

| CH3 of first immunoglobulin | CH3 of second immunoglobulin |
|---|---|
| T366Y | Y407T |
| T366W | Y407A |
| F405A | T394W |
| Y407T | T366Y |
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code). Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2.

Following mutation of the DNA as discussed above, polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as *E. coli*, or eukaryotic host cells, such as CHO cells. Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, and they may be assembled together in vitro. Assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Spiess et al., *Nat Biotechnol* 31:753-8, 2013. In some embodiments, modified immunoglobulin polypeptides may be expressed separately in CHO cells and assembled in vitro using the methods described above.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain ($V_H$) and a variable light chain ($V_L$) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

The "diabody" technology described by Hollinger et al., *Proc. Natl. Acad. Sci. USA*, 90:6444-6448 (1993) has provided an alternative mechanism for making bispecific antibody fragments. The fragments comprise a heavy chain variable domain ($V_H$) connected to a light chain variable domain ($V_L$) by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Conjugated or Otherwise Modified Antibodies

The antibody used in the methods or included in the articles of manufacture herein is optionally conjugated to a cytotoxic agent. For instance, the antibody may be conjugated to a drug as described in WO2004/032828.

Chemotherapeutic agents useful in the generation of such antibody-cytotoxic agent conjugates have been described above.

Conjugates of an antibody and one or more small molecule toxins, such as a calicheamicin, a maytansine (U.S. Pat. No. 5,208,020), a trichothene, and CC1065 are also contemplated herein. In one embodiment of the invention, the antibody is conjugated to one or more maytansine molecules (e.g. about 1 to about 10 maytansine molecules per antibody molecule). Maytansine may, for example, be converted to May-SS-Me, which may be reduced to May-SH3 and reacted with modified antibody (Chari et al. *Cancer Research* 52: 127-131 (1992)) to generate a maytansinoid-antibody conjugate.

Alternatively, the antibody is conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^I$, $\alpha_2^I$, $\alpha_3^I$, N-acetyl-$\gamma_1^I$, PSAG and $\theta_1^I$ (Hinman et al. *Cancer Research* 53: 3336-3342 (1993) and Lode et al. *Cancer Research* 58: 2925-2928 (1998)).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993.

The present invention further contemplates antibody conjugated with a compound with nucleolytic activity (e.g. a ribonuclease or a DNA endonuclease such as a deoxyribonuclease; DNase).

A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

In yet another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) that is conjugated to a cytotoxic agent (e.g. a radionucleotide).

The antibodies of the present invention may also be conjugated with a prodrug-activating enzyme that converts a prodrug (e.g. a peptidyl chemotherapeutic agent, see WO81/01145) to an active anti-cancer drug. See, for example, WO 88/07378 and U.S. Pat. No. 4,975,278.

The enzyme component of such conjugates includes any enzyme capable of acting on a prodrug in such a way so as to convert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328: 457-458 (1987)). Antibody-abzyme conjugates can be prepared as described herein for delivery of the abzyme to a tumor cell population.

The enzymes of this invention can be covalently bound to the antibody by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312: 604-608 (1984)).

Other modifications of the antibody are contemplated herein. For example, the antibody may be linked to one of a variety of nonproteinaceous polymers, e.g., polyethylene glycol (PEG), polypropylene glycol, polyoxyalkylenes, or copolymers of polyethylene glycol and polypropylene glycol. In some embodiments, the antibody fragments, such as Fab', are linked to one or more PEG molecules.

The antibodies disclosed herein may also be formulated as liposomes. Liposomes containing the antibody are prepared by methods known in the art, such as described in Epstein et al., *Proc. Natl. Acad. Sci. USA,* 82:3688 (1985); Hwang et al., *Proc. Natl. Acad. Sci. USA,* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of an antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

Antibody Variants

Amino acid sequence modification(s) of the antibody are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science,* 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of an enzyme, or a polypeptide that increases the serum half-life of the antibody.

Another type of variant is an amino acid substitution variant. These variants have at least one amino acid residue in the antibody molecule replaced by different residue. The sites of greatest interest for substitutional mutagenesis of antibody antibodies include the hypervariable regions, but FR alterations are also contemplated. Conservative substitutions are shown in Table 3 under the heading of "preferred substitutions". If such substitutions result in a change in biological activity, then more substantial changes, denominated "exemplary substitutions" in Table 3, may be introduced and the products screened.

TABLE 3

CONSERVATIVE AMINO ACID SUBSTITUTIONS

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His(H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody. Generally, the resulting variant (s) selected for further development will have improved biological properties relative to the parent antibody from which they are generated. A convenient way for generating such substitutional variants is affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or in additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is screened as described herein and antibodies with superior properties in one or more relevant assays may be selected for further development.

Another type of amino acid variant of the antibody alters the original glycosylation pattern of the antibody. Such altering includes deleting one or more carbohydrate moieties found in the antibody, and/or adding one or more glycosylation sites that are not present in the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1 (Presta, L.); see also US 2004/0093621 A1 (Kyowa Hakko Kogyo Co., Ltd) concerning a CD20 antibody composition. Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue attached to the oligosaccharide attached to an Fc region of the antibody are reported in WO97/30087 (Patel et al.); see also WO98/58964 (Raju, S.) and WO99/22764 (Raju, S.) concerning antibodies with altered carbohydrate attached to the Fc region thereof.

In some embodiments, the glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US Pat. Appl. No. US 2003/0157108 A1, Presta, L; WO 00/61739A1; WO01/29246A1; US2003/0115614A1; US2002/0164328A1; US2004/0093621A1; US2004/0132140A1; US2004/0110704A1; US2004/0110282A1; US2004/0109865A1; WO03/085119A1; WO03/084570A1; WO2005/035778; WO2005/035586 (describing RNA inhibition (RNAi) of fucosylation); Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered that has dual Fc regions and may thereby have enhanced complement lysis and ADCC capabilities. See Stevenson et al. *Anti-Cancer Drug Design* 3:219-230 (1989).

WO 00/42072 (Presta, L.) describes antibodies with improved ADCC function in the presence of human effector cells, where the antibodies comprise amino acid substitutions in the Fc region thereof. In some embodiments, the antibody with improved ADCC comprises substitutions at positions 298, 333, and/or 334 of the Fc region. In some embodiments, the altered Fc region is a human IgG1 Fc region comprising or consisting of substitutions at one, two or three of these positions.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Antibodies with substitutions in an Fc region thereof and increased serum half-lives are also described in WO00/42072 (Presta, L.).

Engineered antibodies with three or more (preferably four) functional antigen binding sites are also contemplated (US Appln No. US2002/0004587 A1, Miller et al.).

The antibodies of the invention can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Vectors, Host Cells, and Recombinant Methods

Antibodies may also be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

Signal Sequence Component

An antibody of the invention may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, 1pp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

Origin of Replication

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ, plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter.

Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, etc.

For example, cells transformed with the DHFR gene are identified by culturing the transformants in a culture medium containing methotrexate (Mtx), a competitive antagonist of DHFR. Under these conditions, the DHFR gene is amplified along with any other co-transformed nucleic acid. A Chinese hamster ovary (CHO) cell line deficient in endogenous DHFR activity (e.g., ATCC CRL-9096) may be used.

Alternatively, cells transformed with the GS gene are identified by culturing the transformants in a culture medium containing L-methionine sulfoximine (Msx), an inhibitor of GS. Under these conditions, the GS gene is amplified along with any other co-transformed nucleic acid. The GS selection/amplification system may be used in combination with the DHFR selection/amplification system described above.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 (1979)). The trp1 gene provides a selection marker for a mutant strain of yeast lacking the ability to grow in tryptophan, for example, ATCC No. 44076 or PEP4-1. Jones, *Genetics*, 85:12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, *Bio/Technology*, 8:135 (1990). Stable multi-copy expression vectors for secretion of mature recombinant human serum albumin by industrial strains of *Kluyveromyces* have also been disclosed. Fleer et al., *Bio/Technology*, 9:968-975 (1991).

Promoter Component

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoter sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Antibody transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), or from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

Enhancer Element Component

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody-encoding sequence, but is preferably located at a site 5' from the promoter.

Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding antibody. One useful transcription termination component is the bovine growth hormone polyadenylation region. See WO94/11026 and the expression vector disclosed therein.

Selection and Transformation of Host Cells

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Full length antibody, antibody fusion proteins, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in *E. coli* is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, *Methods in Molecular Biology, Vol.* 248 (B. K. C. Lo, ed., Humana Press, Totowa, N.J., 2003), pp. 245-254, describing expression of antibody fragments in *E. coli*. After expression, the antibody may be isolated from the *E. coli* cell paste in a soluble fraction and can be purified through, e.g., a protein A or G column depending on the isotype. Final purification can be carried out similar to the process for purifying antibody expressed e.g., in CHO cells.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*. For a review discussing the use of yeasts and filamentous fungi for the production of therapeutic proteins, see, e.g., Gerngross, *Nat. Biotech.* 22:1409-1414 (2004).

Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006) (describing humanization of the glycosylation pathway in *Pichia pastoris*); and Gerngross et al., supra.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the invention, particularly for transfection of *Spodoptera frugiperda* cells.

Plant cell cultures of cotton, corn, potato, soybean, *petunia*, tomato, duckweed (Leninaceae), alfalfa (*M. truncatula*), and tobacco can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

Host cells are transformed with the above-described expression or cloning vectors for antibody production and cultured in conventional nutrient media modified as appropriate for inducing promoters, selecting transformants, or amplifying the genes encoding the desired sequences.

Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Purification of Antibody

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

In general, various methodologies for preparing antibodies for use in research, testing, and clinical are well-established in the art, consistent with the above-described methodologies and/or as deemed appropriate by one skilled in the art for a particular antibody of interest.

Selecting Biologically Active Antibodies

Antibodies produced as described above may be subjected to one or more "biological activity" assays to select an antibody with beneficial properties from a therapeutic perspective or selecting formulations and conditions that retain biological activity of the antibody. The antibody may be tested for its ability to bind the antigen against which it was raised. For example, methods known in the art (such as ELISA, Western Blot, etc.) may be used.

For example, for an anti-PDL1 antibody, the antigen binding properties of the antibody can be evaluated in an assay that detects the ability to bind to PDL1. In some embodiments, the binding of the antibody may be determined by saturation binding; ELISA; and/or competition assays (e.g. RIA's), for example. Also, the antibody may be subjected to other biological activity assays, e.g., in order to evaluate its effectiveness as a therapeutic. Such assays are known in the art and depend on the target antigen and intended use for the antibody. For example, the biological effects of PD-L1 blockade by the antibody can be assessed in CD8+ T cells, a lymphocytic choriomeningitis virus (LCMV) mouse model and/or a syngeneic tumor model e.g., as described in U.S. Pat. No. 8,217,149.

To screen for antibodies which bind to a particular epitope on the antigen of interest (e.g., those which block binding of the anti-PDL1 antibody of the example to PD-L1), a routine cross-blocking assay such as that described in *Antibodies, A Laboratory Manual*, Cold Spring Harbor Laboratory, Ed Harlow and David Lane (1988), can be performed. Alternatively, epitope mapping, e.g. as described in Champe et al., *J. Biol. Chem.* 270:1388-1394 (1995), can be performed to determine whether the antibody binds an epitope of interest.

V. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as TWEEN™, PLURONICS™ or polyethylene glycol (PEG).

Lyophilized formulations adapted for subcutaneous administration are described in U.S. Pat. No. 6,267,958 (Andya et al.). Such lyophilized formulations may be reconstituted with a suitable diluent to a high protein concentration and the reconstituted formulation may be administered subcutaneously to the mammal to be treated herein.

Crystalized forms of the antibody or antibody are also contemplated. See, for example, US 2002/0136719A1 (Shenoy et al.).

The formulation herein may also contain more than one active compound as necessary for the particular indication being treated, in some embodiments, those with complementary activities that do not adversely affect each other. For example, it may be desirable to further provide a cytotoxic agent; chemotherapeutic agent; immunosuppressive agent; cytokine; cytokine antagonist or antibody; growth factor; hormone; integrin; integrin antagonist or antibody (e.g. an LFA-1 antibody such as efalizumab/RAPTIVA commercially available from Genentech, or an alpha 4 integrin antibody such as natalizumab/TYSABRI®) available from Biogen Idec/Elan Pharmaceuticals, Inc.); interferon class drug such as IFN-beta-1a (REBIF® and AVONEX®) or IFN-beta-1b (BETASERON®); an oligopeptide such a glatiramer acetate (COPAXONE®); a cytotoxic agent such as mitoxantrone (NOVANTRONE®), methotrexate, cyclophosphamide, chlorambucil, or azathioprine; intravenous immunoglobulin (gamma globulin); lymphocyte-depleting drug (e.g., mitoxantrone, cyclophosphamide, Campath, anti-CD4, or cladribine); non-lymphocyte-depleting immunosuppressive drug (e.g., mycophenolate mofetil (MMF) or cyclosporine); cholesterol-lowering drug of the "statin" class; estradiol; testosterone; hormone replacement therapy; drug that treats symptoms secondary or related to MS (e.g., spasticity, incontinence, pain, fatigue); a TNF inhibitor; disease-modifying anti-rheumatic drug (DMARD); non-steroidal anti-inflammatory drug (NSAID); corticosteroid (e.g. methylprednisolone, prednisone, dexamethasone, or glucorticoid); levothyroxine; cyclosporin A; somatastatin analogue; cytokine antagonist; anti-metabolite; immunosuppressive agent; integrin antagonist or antibody (e.g. an LFA-1 antibody, such as efalizumab or an alpha 4 integrin antibody such as natalizumab); or another B-cell surface antagonist/antibody; etc in the formulation. The type and effective amounts of such other agents depend, for example, on the amount of antibody present in the formulation, the type of multiple sclerosis being treated, and clinical parameters of the patients. These are generally used in the same dosages and with administration routes as used hereinbefore or about from 1 to 99% of the heretofore employed dosages.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

VI. Administration

In some embodiments the anti-PD-L1 antibody is administered intravenously, intramuscularly, subcutaneously, topically, orally, transdermally, intraperitoneally, intraorbitally, by implantation, by inhalation, intrathecally, intraventricularly, or intranasally. An effective amount of the anti-PD-L1 antibody may be administered for prevention or treatment of disease. The appropriate dosage of the anti-PD-L1 antibody may be determined based on the type of disease to be treated, the type of anti-PD-L1 antibody, the severity and course of the disease, the clinical condition of the individual, the individual's clinical history and response to the treatment, and the discretion of the attending physician.

As a general proposition, the therapeutically effective amount of the antibody administered to human may be in the range of about 0.01 to about 50 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antibody is administered at 15 mg/kg. However, other dosage regimens may be useful. In one embodiment, an anti-PDL1 antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The dose of the antibody administered in a combination treatment may be reduced as compared to a single treatment. The progress of this therapy is easily monitored by conventional techniques.

In some embodiments, the methods may further comprise an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PI3K/AKT/mTOR pathway, HSP90 inhibitor, tubulin inhibitor, apoptosis inhibitor, and/or chemopreventative agent. The additional therapy may be one or more of the chemotherapeutic agents described herein.

Combination Therapies

In certain embodiments, the anti-PD-L1 antibody is administered in conjunction with another anti-cancer agent or cancer therapy. "In conjunction with" refers to administration of one treatment modality in addition to another treatment modality. As such, "in conjunction with" refers to administration of one treatment modality before, during (such as concurrently or simultaneously), or after administration of the other treatment modality to the individual.

In some embodiments, the anti-PD-L1 antibody may be administered in conjunction with a chemotherapy or chemotherapeutic agent. In some embodiments, the anti-PD-L1 antibody may be administered in conjunction with a radiation therapy or radiotherapeutic agent. In some embodiments, the anti-PD-L1 antibody may be administered in conjunction with a targeted therapy or targeted therapeutic agent. In some embodiments, the anti-PD-L1 antibody may be administered in conjunction with an immunotherapy or immunotherapeutic agent, for example a monoclonal antibody.

Without wishing to be bound to theory, it is thought that enhancing T cell stimulation, by promoting an activating co-stimulatory molecule or by inhibiting a negative co-stimulatory molecule, may promote tumor cell death thereby treating or delaying progression of cancer. In some embodiments, the anti-PD-L1 antibody may be administered in conjunction with an agonist directed against an activating co-stimulatory molecule. In some embodiments, an activating co-stimulatory molecule may include CD40, CD226, CD28, OX40, GITR, CD137, CD27, HVEM, or CD127. In some embodiments, the agonist directed against an activating co-stimulatory molecule is an agonist antibody that binds to CD40, CD226, CD28, OX40, GITR, CD137, CD27, HVEM, or CD127. In some embodiments, the anti-PD-L1 antibody may be administered in conjunction with an antagonist directed against an inhibitory co-stimulatory molecule. In some embodiments, an inhibitory co-stimulatory molecule may include CTLA-4 (also known as CD152), PD-1, TIM-3, BTLA, VISTA, LAG-3, B7-H3, B7-H4, IDO, TIGIT, MICA/B, or arginase. In some embodiments, the antagonist directed against an inhibitory co-stimulatory molecule is an antagonist antibody that binds to CTLA-4, PD-1, TIM-3, BTLA, VISTA, LAG-3, B7-H3, B7-H4, IDO, TIGIT, MICA/B, or arginase.

In some embodiments, the anti-PD-L1 antibody may be administered in conjunction with an antagonist directed against CTLA-4 (also known as CD152), e.g., a blocking antibody. In some embodiments, the anti-PD-L1 antibody may be administered in conjunction with ipilimumab (also known as MDX-010, MDX-101, or Yervoy®). In some embodiments, the anti-PD-L1 antibody may be administered in conjunction with tremelimumab (also known as ticilimumab or CP-675,206). In some embodiments, the anti-PD-L1 antibody may be administered in conjunction with an antagonist directed against B7-H3 (also known as CD276), e.g., a blocking antibody. In some embodiments, the anti-PD-L1 antibody may be administered in conjunction with MGA271. In some embodiments, the anti-PD-L1 antibody may be administered in conjunction with an antagonist directed against a TGF beta, e.g., metelimumab (also known as CAT-192), fresolimumab (also known as GC1008), or LY2157299.

In some embodiments, the anti-PD-L1 antibody may be administered in conjunction with a treatment comprising adoptive transfer of a T cell (e.g., a cytotoxic T cell or CTL) expressing a chimeric antigen receptor (CAR). In some embodiments, the anti-PD-L1 antibody may be administered in conjunction with a treatment comprising adoptive transfer of a T cell comprising a dominant-negative TGF beta receptor, e.g, a dominant-negative TGF beta type II receptor. In some embodiments, the anti-PD-L1 antibody may be administered in conjunction with a treatment comprising a HERCREEM protocol (see, e.g., ClinicalTrials.gov Identifier NCT00889954).

In some embodiments, the anti-PD-L1 antibody may be administered in conjunction with an agonist directed against CD137 (also known as TNFRSF9, 4-1BB, or ILA), e.g., an activating antibody. In some embodiments, the anti-PD-L1 antibody may be administered in conjunction with urelumab (also known as BMS-663513). In some embodiments, the anti-PD-L1 antibody may be administered in conjunction with an agonist directed against CD40, e.g., an activating antibody. In some embodiments, the anti-PD-L1 antibody may be administered in conjunction with CP-870893. In some embodiments, the anti-PD-L1 antibody may be administered in conjunction with an agonist directed against OX40 (also known as CD134), e.g., an activating antibody. In some embodiments, the anti-PD-L1 antibody may be administered in conjunction with an anti-OX40 antibody (e.g., AgonOX). In some embodiments, the anti-PD-L1 antibody may be administered in conjunction with an agonist directed against CD27, e.g., an activating antibody. In some embodiments, the anti-PD-L1 antibody may be administered in conjunction with CDX-1127. In some embodiments, the anti-PD-L1 antibody may be administered in conjunction with an antagonist directed against indoleamine-2,3-dioxygenase (IDO). In some embodiments, with the IDO antagonist is 1-methyl-D-tryptophan (also known as 1-D-MT).

In some embodiments, the anti-PD-L1 antibody may be administered in conjunction with an antibody-drug conjugate. In some embodiments, the antibody-drug conjugate comprises mertansine or monomethyl auristatin E (MMAE). In some embodiments, the anti-PD-L1 antibody may be administered in conjunction with and anti-NaPi2b antibody-MMAE conjugate (also known as DNIB0600A or RG7599). In some embodiments, the anti-PD-L1 antibody may be administered in conjunction with trastuzumab emtansine (also known as T-DM1, ado-trastuzumab emtansine, or KADCYLA®, Genentech). In some embodiments, the anti-PD-L1 antibody may be administered in conjunction with DMUC5754A. In some embodiments, the anti-PD-L1 antibody may be administered in conjunction with an antibody-drug conjugate targeting the endothelin B receptor (EDNBR), e.g., an antibody directed against EDNBR conjugated with MMAE.

In some embodiments, the anti-PD-L1 antibody may be administered in conjunction with an angiogenesis inhibitor. In some embodiments, the anti-PD-L1 antibody may be administered in conjunction with an antibody directed against a VEGF, e.g., VEGF-A. In some embodiments, the anti-PD-L1 antibody may be administered in conjunction with bevacizumab (also known as AVASTIN™, Genentech). In some embodiments, the anti-PD-L1 antibody may be administered in conjunction with an antibody directed against angiopoietin 2 (also known as Ang2). In some embodiments, the anti-PD-L1 antibody may be administered in conjunction with MEDI3617.

In some embodiments, the anti-PD-L1 antibody may be administered in conjunction with an antineoplastic agent. In some embodiments, the anti-PD-L1 antibody may be administered in conjunction with an agent targeting CSF-1R (also known as M-CSFR or CD115). In some embodiments, the anti-PD-L1 antibody may be administered in conjunction with anti-CSF-1R (also known as IMC-CS4). In some embodiments, the anti-PD-L1 antibody may be administered in conjunction with an interferon, for example interferon alpha or interferon gamma. In some embodiments, the anti-PD-L1 antibody may be administered in conjunction with Roferon-A (also known as recombinant Interferon alpha-2a). In some embodiments, the anti-PD-L1 antibody may be administered in conjunction with GM-CSF (also known as recombinant human granulocyte macrophage colony stimulating factor, rhu GM-CSF, sargramostim, or Leukine®). In some embodiments, the anti-PD-L1 antibody may be administered in conjunction with IL-2 (also known as aldesleukin or Proleukin®). In some embodiments, the anti-PD-L1 antibody may be administered in conjunction with IL-12. In some embodiments, the anti-PD-L1 antibody may be administered in conjunction with an antibody targeting CD20. In some embodiments, the antibody targeting CD20 is obinutuzumab (also known as GA101 or Gazyva®) or rituximab. In some embodiments, the anti-PD-L1 antibody may be administered in conjunction with an antibody targeting GITR. In some embodiments, the antibody targeting GITR is TRX518.

In some embodiments, the anti-PD-L1 antibody may be administered in conjunction with a cancer vaccine. In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, the anti-PD-L1 antibody may be administered in conjunction with an adjuvant. In some embodiments, the anti-PD-L1 antibody may be administered in conjunction with a treatment comprising a TLR agonist, e.g., Poly-ICLC (also known as Hiltonol®), LPS, MPL, or CpG ODN. In some embodiments, the anti-PD-L1 antibody may be administered in conjunction with tumor necrosis factor (TNF) alpha. In some embodiments, the anti-PD-L1 antibody may be administered in conjunction with IL-1. In some embodiments, the anti-PD-L1 antibody may be administered in conjunction with HMGB1. In some embodiments, the anti-PD-L1 antibody may be administered in conjunction with an IL-10 antagonist. In some embodiments, the anti-PD-L1 antibody may be administered in conjunction with an IL-4 antagonist. In some embodiments, the anti-PD-L1 antibody may be administered in conjunction with an IL-13 antagonist. In some embodiments, the anti-PD-L1 antibody may be administered in conjunction with an HVEM antagonist. In some embodiments, the anti-PD-L1 antibody may be administered in conjunction with an ICOS agonist, e.g., by administration of ICOS-L, or an agonistic antibody directed against ICOS. In some embodiments, the anti-PD-L1 antibody may be administered in conjunction with a treatment targeting CX3CL1. In some embodiments, the anti-PD-L1 antibody may be administered in conjunction with a treatment targeting CXCL9. In some embodiments, the anti-PD-L1 antibody may be administered in conjunction with a treatment targeting CXCL10. In some embodiments, the anti-PD-L1 antibody may be administered in conjunction with a treatment targeting CCL5. In some embodiments, the anti-PD-L1 antibody may be administered in conjunction with an LFA-1 or ICAM1 agonist. In some embodiments, the anti-PD-L1 antibody may be administered in conjunction with a Selectin agonist.

In some embodiments, the anti-PD-L1 antibody may be administered in conjunction with a targeted therapy. In some embodiments, the anti-PD-L1 antibody may be administered in conjunction with an inhibitor of B-Raf. In some embodiments, the anti-PD-L1 antibody may be administered in conjunction with vemurafenib (also known as Zelboraf®). In some embodiments, the anti-PD-L1 antibody may be administered in conjunction with dabrafenib (also known as Tafinlar®). In some embodiments, the anti-PD-L1 antibody may be administered in conjunction with erlotinib (also known as Tarceva®). In some embodiments, the anti-PD-L1 antibody may be administered in conjunction with an inhibitor of a MEK, such as MEK1 (also known as MAP2K1) or MEK2 (also known as MAP2K2). In some embodiments, the anti-PD-L1 antibody may be administered in conjunction with cobimetinib (also known as GDC-0973 or XL-518). In some embodiments, the anti-PD-L1 antibody may be administered in conjunction with trametinib (also known as Mekinist®). In some embodiments, the anti-PD-L1 antibody may be administered in conjunction with an inhibitor of K-Ras. In some embodiments, the anti-PD-L1 antibody may be administered in conjunction with an inhibitor of c-Met. In some embodiments, the anti-PD-L1 antibody may be administered in conjunction with onartuzumab (also known as MetMAb). In some embodiments, the anti-PD-L1 antibody may be administered in conjunction with an inhibitor of Alk. In some embodiments, the anti-PD-L1 antibody may be administered in conjunction with AF802 (also known as CH5424802 or alectinib). In some embodiments, the anti-PD-L1 antibody may be administered in conjunction with an inhibitor of a phosphatidylinositol 3-kinase (PI3K). In some embodiments, the anti-PD-L1 antibody may be administered in conjunction with BKM120. In some embodiments, the anti-PD-L1 antibody may be administered in conjunction with idelalisib (also known as GS-1101 or CAL-101). In some embodiments, the anti-PD-L1 antibody may be administered in conjunction with perifosine (also known as KRX-0401). In some embodiments, the anti-PD-L1 antibody may be administered in conjunction with an inhibitor of an Akt. In some embodiments, the anti-PD-L1 antibody may be administered in conjunction with MK2206. In some embodiments, the anti-PD-L1 antibody may be administered in conjunction with GSK690693. In some embodiments, the anti-PD-L1 antibody may be administered in conjunction with GDC-0941. In some embodiments, the anti-PD-L1 antibody may be administered in conjunction with an inhibitor of mTOR. In some embodiments, the anti-PD-L1 antibody may be administered in conjunction with sirolimus (also known as rapamycin). In some embodiments, the anti-PD-L1 antibody may be administered in conjunction with temsirolimus (also known as CCI-779 or Torisel®). In some embodiments, the anti-PD-L1 antibody may be administered in conjunction with everolimus (also known as RAD001). In some embodiments, the anti-PD-L1 antibody may be administered in conjunction with ridaforolimus (also known as AP-23573, MK-8669, or deforolimus). In some embodiments, the anti-PD-L1 antibody may be administered in conjunction with OSI-027. In some embodiments, the anti-PD-L1 antibody may be administered in conjunction with AZD8055. In some embodiments, the anti-PD-L1 antibody may be administered in conjunction with INK128. In some embodiments, the anti-PD-L1 antibody may be administered in conjunction with a dual PI3K/mTOR inhibitor. In some embodiments, the anti-PD-L1 antibody may be administered in conjunction with XL765. In some embodiments, the anti-PD-L1 antibody may be administered in conjunction with GDC-0980. In some embodiments, the anti-PD-L1 antibody may be administered in conjunction with BEZ235 (also known as NVP-BEZ235). In some embodiments, the anti-PD-L1 antibody may be administered in conjunction with BGT226. In some embodiments, the anti-PD-L1 antibody may be administered in conjunction with GSK2126458. In some embodiments, the anti-PD-L1 antibody may be administered in conjunction with PF-04691502. In some embodiments, the anti-PD-L1 antibody may be administered in conjunction with PF-05212384 (also known as PKI-587).

VII. Kits and Articles of Manufacture

The invention further provides kits and articles of manufacture containing materials useful for the treatment of cancer according to the methods described herein.

In some embodiments, the invention provides an of manufacture comprising, packaged together, a pharmaceutical composition comprising an anti-PD-L1 antibody (or antigen binding fragment thereof) and a pharmaceutically acceptable carrier, and a label denoting that the anti-PD-L1 antibody (or antigen binding fragment thereof) or pharmaceutical composition is indicated for treating subjects with cancer having medium or low methylation level at CpG1 in the PD-L1 promoter region or at one or more CpG sites in intron 1 of the PD-L1 gene in a sample containing cancer cells from the subject. In some embodiments, the article of manufacture further comprises instructions for administering the anti-PD-L1 antibody (or antigen binding fragment thereof) or pharmaceutical composition to a subject with cancer having medium or low methylation level at CpG1 in the PD-L1 promoter region or at one or more CpG sites in intron 1 of the PD-L1 gene in a sample containing cancer cells from the subject.

In some embodiments, the invention provides an of manufacture comprising, packaged together, a pharmaceutical composition comprising an anti-PD-L1 antibody (or antigen binding fragment thereof) and a pharmaceutically acceptable carrier, and a label denoting that administration of the anti-PD-L1 antibody (or antigen binding fragment thereof) or pharmaceutical composition is based upon the patient having medium or low level of methylation at CpG1 in the PD-L1 promoter region or at one or more CpG sites in intron 1 of the PD-L1 gene in a sample containing cancer cells from the subject. In some embodiments, the article of manufacture further comprises instructions for administering the anti-PD-L1 antibody (or antigen binding fragment thereof) or pharmaceutical composition to a subject with cancer having medium or low methylation level at CpG1 in the PD-L1 promoter region or at one or more CpG sites in intron 1 of the PD-L1 gene in a sample containing cancer cells from the subject.

In some embodiments, the invention provides an of manufacture comprising, packaged together, a pharmaceutical composition comprising an anti-PD-L1 antibody (or antigen binding fragment thereof) and a pharmaceutically acceptable carrier, and a label denoting that anti-PD-L1 antibody (or antigen binding fragment thereof) or pharmaceutical composition is administered to a selected patient, wherein the subject has been found to have medium or low level of methylation at CpG1 in the PD-L1 promoter region or at one or more CpG sites in intron 1 of the PD-L1 gene in a sample containing cancer cells from the subject. In some embodiments, the article of manufacture further comprises instructions for administering the anti-PD-L1 antibody (or antigen binding fragment thereof) or pharmaceutical composition to a subject with cancer having medium or low methylation level at CpG1 in the PD-L1 promoter region or at one or more CpG sites in intron 1 of the PD-L1 gene in a sample containing cancer cells from the subject.

In some embodiments, the invention provides a kit comprising reagents for measuring methylation level at CpG1 in the PD-L1 promoter region and/or at one or more CpG sites in intron 1 of the PD-L1 gene in a sample containing cancer cells from the subject and instructions for classifying the subject as having medium or low methylation level at CpG1 in the PD-L1 promoter region and/or at one or more CpG sites in intron 1 of the PD-L1 gene. In certain embodiments, the kit further comprises an anti-PD-L1 antibody, and instructions for administering the anti-PD-L1 antibody to the subject if the subject has medium or low methylation level at CpG1 in the PD-L1 promoter region and/or at one or more CpG sites in intron 1 of the PD-L1 gene.

In some embodiments of any of the kits or articles of manufacture described herein, the subject has been found to have medium or low level of methylation at CpG1 in the PD-L1 promoter region and at one or more CpG sites in intron 1 of the PD-L1 gene in a sample containing cancer cells from the subject.

In some embodiments of any of the kits or articles of manufacture described herein, the label denotes that the degree of methylation at CpG1 in the PD-L1 promoter region or at one or more CpG sites in intron 1 of the PD-L1 is determined by bisulfite DNA sequencing, In some embodiments of any of the kits or articles of manufacture described herein, the label denotes that the degree of methylation at CpG1 in the PD-L1 promoter region or at one or more CpG sites in intron 1 of the PD-L1 is determined by bisulfite next generation sequencing. In some embodiments of any of the kits or articles of manufacture described herein, the label denotes that the degree of methylation at CpG1 in the PD-L1 promoter region or at one or more CpG sites in intron 1 of the PD-L1 is determined using a methylation chip array (such as the INFINIUM® HumanMethylation450 BeadChip array).

In some embodiments, the kits or articles of manufacture provided herein include reagents for detecting immune cell infiltration in a sample containing cancer cells from the subject.

In some embodiments the reagents include one or more of the following: an anti-CD16 antibody, an anti-CD4 antibody, an anti-CD3 antibody, an anti-CD56 antibody, an anti-CD45 antibody, an anti-CD68 antibody, an anti-CD20 antibody, an anti-CD163 antibody, or anti-CD8 antibody. In some embodiments, the reagent is an anti-CD8 antibody. In some embodiments, the kits or articles of manufacture provided herein further comprise instructions for performing an immunohistochemical assay (including, but not limited to, western blot, ELISA, or flow cytometry) in order to detect immune cell infiltration in a sample containing cancer cells from the subject. In some embodiments, the kits or articles of manufacture provided herein further comprise instructions for performing a gene expression analysis assay, including, but not limited to quantitative PCR (qPCR), qRT-PCR, transcriptome profiling (such as RNAseq), microarray analyses, next generation sequencing, etc.

In some embodiments of any of the kits or articles of manufacture provided herein, the cancer is breast cancer, lung cancer, or skin cancer, including metastatic forms of those cancers. In certain embodiments, the breast cancer is breast carcinoma. In some embodiments, lung cancer is small cell lung cancer, non-small cell lung cancer, adenocarcinoma of the lung, or squamous cell carcinoma of the lung. In certain embodiments, the skin cancer is melanoma, superficial spreading melanoma, lentigo maligna melanoma, acral lentiginous melanomas, nodular melanomas, or skin carcinoma.

In some embodiments of any of the kits or articles of manufacture, the anti-PD-L1 antibody (or antigen binding fragment thereof) included in the kit or article of manufacture is an anti-PD-L1 antibody described herein. In some embodiments of any of the kits or articles of manufacture, the anti-PD-L1 antibody (or antigen binding fragment thereof) is selected from the group consisting of YW243.55.S70, MPDL3280A, MDX-1105, and MEDI4736. Other exemplary anti-PD-L1 antibodies (or antigen binding fragments thereof) that can be included in the articles of manufacture provided herein, or included in the articles of manufacture or kits provided herein, are described in WO 2010/077634, WO 2007/005874, WO 2011/066389, and US 2013/034559, each of which is incorporated herein by reference in its entirety.

Typically, a kit or article of manufacture comprises a container and a label or package insert on or associated with the container. Suitable containers include, for example, bottles, vials, syringes, etc. The containers may be formed from a variety of materials such as glass or plastic. The container holds or contains the anti-PD-L1 antibody (or antigen binding fragment thereof) or the pharmaceutical composition effective for treating cancer and may have a sterile access port (for example the container may be an intravenous solution bag or a vial having a stopper pierceable by a hypodermic injection needle). At least one active agent in the composition is an anti-PD-L1 antibody The label or package insert indicates that the composition is used for treating cancer in a patient suffering therefrom with specific guidance regarding dosing amounts and intervals of antibody and any other drug being provided. The article of manufacture may further comprise a second container comprising a pharmaceutically acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

Optionally, the article of manufacture herein further comprises a container comprising an agent other than the antibody for treatment and further comprising instructions on treating the patient with such agent, such agent being, e.g., a chemotherapeutic agent (such as a chemotherpeutic agent described elsewhere herein), a cytotoxic agent (such as a cytotoxic agent described elsewhere herein), etc.

Further details of the invention are illustrated by the following non-limiting Examples. The disclosures of all citations in the specification are expressly incorporated herein by reference.

EXAMPLES

The examples, which are intended to be purely exemplary of the invention and should therefore not be considered to limit the invention in any way, also describe and detail aspects and embodiments of the invention discussed above. The foregoing examples and detailed description are offered by way of illustration and not by way of limitation.

Example 1: Materials and Methods

The following materials and methods were used in Example 2 below.

Cell Lines and Culture Conditions

NSCLC cell lines were procured from American Type Cell Culture (ATCC) or academic sources and cultured in RPMI 1640 medium supplemented with 10% fetal bovine serum (FBS) and 2 mM L-glutamine. Cells were detached for splitting and/or experimental analysis following a PBS wash and incubation with Accutase detachment medium (Sigma). Cells were treated with 0.1 mM trichostatin A ("TSA," Sigma) and/or 1 ng/mL interferon gamma (IFNγ) for 24 hours and 1 mM 5-azacitidine-dC (5-aza-dC, Sigma), for 3 days qd (i.e., once a day) or 6 days q2d (i.e., every other day).

Tumor Samples

Archival tumor specimens from NSCLC patients were procured from IRB-approved vendor collections from The MT Group, Cureline, Inc, Cambridge BioSource, Tristar Technology Group LLC, or ClinPath Advisors.

DNA/RNA Analysis

Buffer RLT Plus (Qiagen) was used to lyse the cells for RNA and DNA extraction from the same lysate using the AllPrep DNA/RNA Mini Kit (Qiagen). RNA expression was analyzed by microarray on the GeneChip Human Genome U133 Plus 2.0 Array (Affymetrix) by Asuragen, Inc, and by qPCR using TaqMan Gene Expression Assays (Life Technologies). Data was analyzed using Genomics Suite (Partek), Spotfire (TIBCO), JMP (SAS), and IPA (Ingenuity). DNA was analyzed on the INFINIUM® HumanMethylation450 BeadChip (Illumina). DNA was bisulfite-modified using the Zymo DNA Gold Methylation kit (Zymo Research) and amplified with bisulfite specific sequencing primers targeting the CD274 promoter region. PCR products were TA-subcloned and sequenced using standard methods (ABI). ABI sequence files were analyzed using BIQ Analyzer software (C. Bock).

Protein Analysis

Protein lysates were generated using Cell Extraction Buffer (Life Technologies), supplemented with SigmaFAST Protease Inhibitor Tablets (Sigma) and Phosphatase Inhibitor Cocktail 1 and 2 (Sigma). Lysates centrifuged at 20,000×g for 10 minutes at 4° C., and the supernatants were then removed for analysis by Western Blot (WB). Samples were treated with NuPage Novex LDS and SRA Buffers (Life Technologies) and loaded onto a Bis-Tris Gel (Life Technologies) alongside SeeBlue Plus2 molecular weight standard (Life Technologies). Gels were transferred to nitrocellulose membranes using the iBlot system (Life Technologies) and then blocked with Odyssey Blocking Buffer (LI-COR) for 1 hour at room temperature. Gels were stained with antibodies against human PD-L1 (in-house), β-actin (Sigma); p/t STAT1, p-STAT3-Y705, p-STAT3-5727, and t-STAT3 (all Cell Signaling) diluted in Odyssey Blocking Buffer+0.01% Tween-20. Primary antibodies were detected secondary antibodies from LI-COR in Odyssey Blocking Buffer+0.01% Tween-20+0.001% SDS and analyzed on the Odyssey CLx system (LI-COR).

For FACS analysis, cells were detached then washed twice in FBS Staining Buffer (BD Biosciences). Cells were then stained with either PE-conjugated anti-human PD-L1 or isotype control (BD Biosciences) and then washed and analyzed on the FACSCanto II Analyzer (BD Biosciences).

Immunohistochemistry (IHC) analyses were performed as described in Herbst et al. (2014) *Nature* 515, 563-574.

Chromatin Immunoprecipitation (ChIP, Active Motif)

NSCLC cell lines were grown to the proper confluency, and treated cells were fixed with 1% formaldehyde for 15 min and quenched with 0.125 M glycine. Chromatin was isolated by the addition of lysis buffer and disruption with a Dounce homogenizer. Lysates were sonicated, and the DNA was sheared to an average length of 300-500 bp. Genomic DNA (Input) was prepared by treating aliquots of chromatin with RNase, proteinase K, and heat for de-crosslinking. Treatment was followed by ethanol precipitation. Pellets of genomic DNA were resuspended and the resulting DNA was quantified on a NanoDrop spectrophotometer. Extrapolation to the original chromatin volume allowed quantitation of the total chromatin yield.

An aliquot of chromatin (30 µg) was pre-cleared with protein A agarose beads (Invitrogen). Genomic DNA regions of interest were isolated using 4 µg antibody against STAT1 (Santa Cruz, cat #sc-345) and STAT3 (Santa Cruz, sc-482). Complexes were washed, eluted from the beads with SDS buffer, and subjected to RNase and proteinase K treatment. Crosslinks were reversed by incubation overnight at 65° C., and chromatin-immuniprecipitated (ChIP) DNA was purified by phenol-chloroform extraction and ethanol precipitation.

The quality of ChIP enrichment was assayed by qPCR using primers against candidate STAT1 and STAT3 control sites. qPCR reactions were carried out in triplicate using SYBR Green Supermix (Bio-Rad). The resulting signals were normalized for primer efficiency by carrying out qPCR for each primer pair using input DNA.

ChIP Sequencing (Illumina, Active Motif)

Illumina sequencing libraries were prepared from the ChIP and Input DNAs by the standard consecutive enzymatic steps of end-polishing, dA-addition, and adaptor ligation. After a final PCR amplification step, the resulting DNA libraries were quantified and sequenced on HiSeq 2500 or NexSeq 500. Sequences (50 nt reads, single end or 75 nt reads, single end) were aligned to the human genome (hg19) using the BWA algorithm. Aligned sequences were each extended in silico at their 3'-ends to a length of 200 bp, i.e., the average genomic fragment length in the size-selected library, and assigned to 32-nt bins along the genome. The resulting histograms (genomic "signal maps") were stored in bigWig files. Peak locations were determined using the MACS algorithm (v1.4.2.) with a cutoff of pvalue=$1\times10^{-7}$. Signal maps and peak locations were used as input data to Active Motifs proprietary analysis program, which creates Excel tables containing detailed information on sample comparison, peak metrics, peak locations and gene annotations.

Bisulfite Next Generation Sequencing (Bisulfite NGS, Active Motif)

NSCLC cell lines analyzed by ChIP-Seq were also analyzed via Bisulfite Next Generation Sequencing (NGS) for methylation status of the PD-L1 Promoter. PCR primers to the target regions (plus strand) were designed with the MethPrimer software (world-wide-web.urogene.org/cgi-bin/methprimer/methprimer.cgi). Primers were used to amplify the target regions from bisulfate converted genomic DNA. For each of the 6 samples, approximately equal amounts of the 9 PCR products were pooled, concatemerized, sonicated to an average fragment length of 150-300 base pairs, and processed into standard, barcoded Illumina sequencing libraries. The Illumina sequencing libraries were sequenced in NextSeq 500. Sequencing reads were analyzed using the bismark alignment program (v 0.7.7) (world-wide-web.bioinformatics.babraham.ac.uk/projects/bismark/). The human chr6 and chr9 (hg19 assembly) were used as reference sequences. Bismark alignment reports are compiled in the file "2674Genentech bismark reports.xlsx". Between 5.1 and 7.4 million reads were analyzed per sample.

Example 2: Analysis of PD-L1 Methylation and Expression

RNA and DNA were extracted from 91 NSCLC cell lines and tested for PD-L1 expression levels (RNA-seq, log 2-count) and promoter methylation (INFINIUM® Array). Two of the five CpG sites (i.e., CpG1-CpG5) showed differential methylation patterns that inversely correlated with PD-L1 RNA expression. See FIG. 1. The first CpG site, i.e., CpG1, shown in FIG. 1 as the CpG site furthest to the left, was found in the predicted PD-L1 promoter site upstream of the TSS. The second CpG site, i.e., CpG5, shown in FIG. 1 as the CpG site furthest to the right, was located within intron 1. A heat map of each of CpGs 1-5 average beta value was plotted with respect to their location in CD274 transcript NM_014143, with their accompanying expression heat map situated to the right of the PD-L1 promoter map at locus 9p24.1. FIG. 1 shows the PD-L1 promoter region expression and methylation heat maps for each cell line tested. The heat maps were sorted by PD-L1 RNA expression, high (red) to low (green). Cell lines with high PD-L1 expression were found low methylation (blue).

Figure 2A:
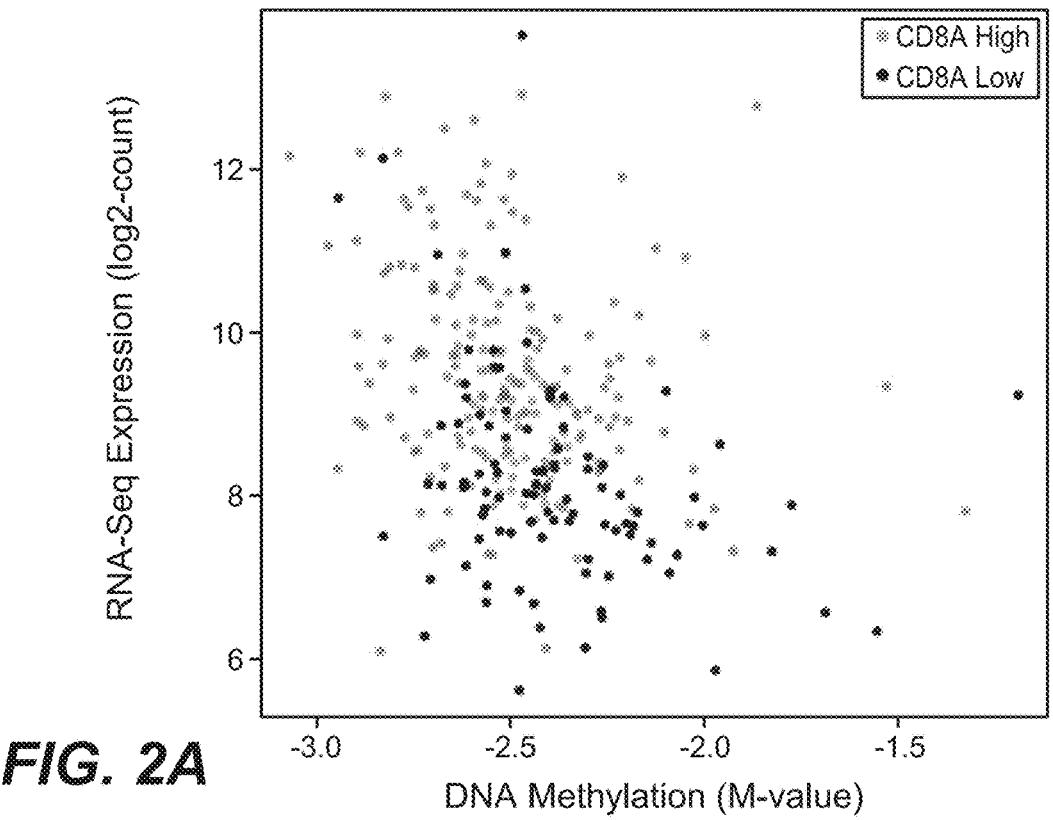
FIG. 2A shows the results of an analysis correlating PD-L1 RNA expression and PD-L1 promoter methylation in a collection of lung adenocarcinoma tumors from The Cancer Genome Atlas.
Figure 2B:
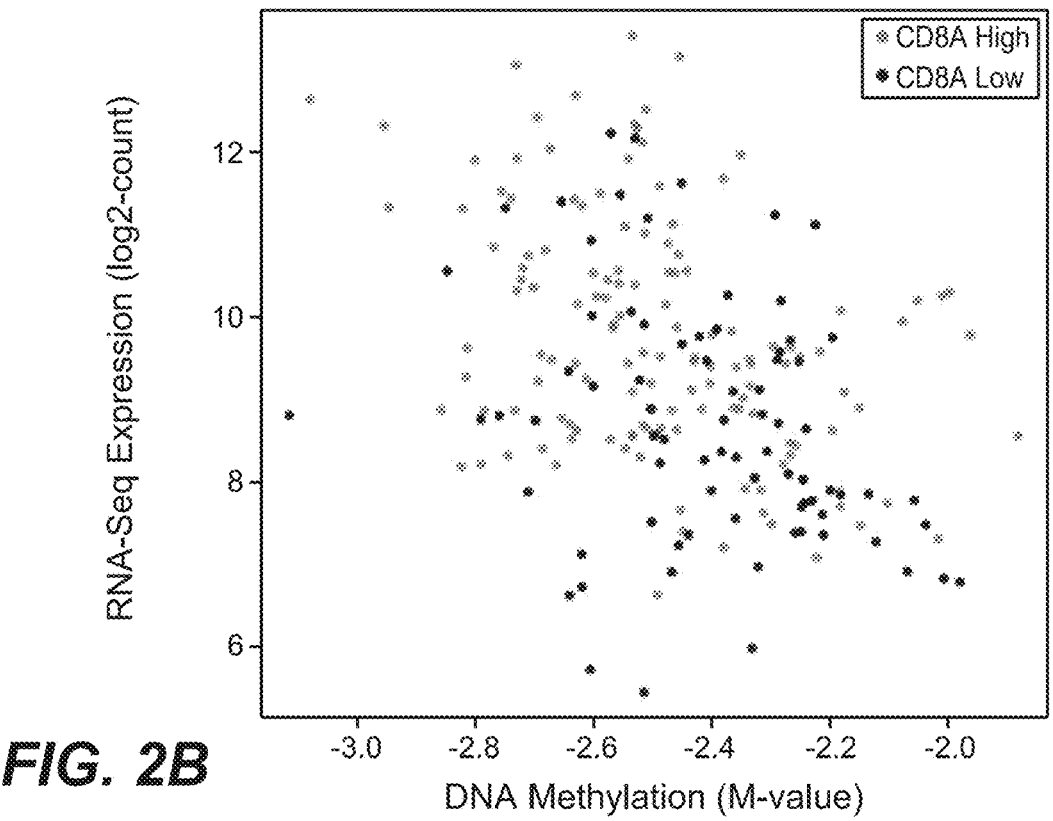
FIG. 2B shows the results of an analysis correlating PD-L1 RNA expression and PD-L1 promoter methylation in a collection of lung squamous cell carcinoma tumors from The Cancer Genome Atlas.
Figure 2C:
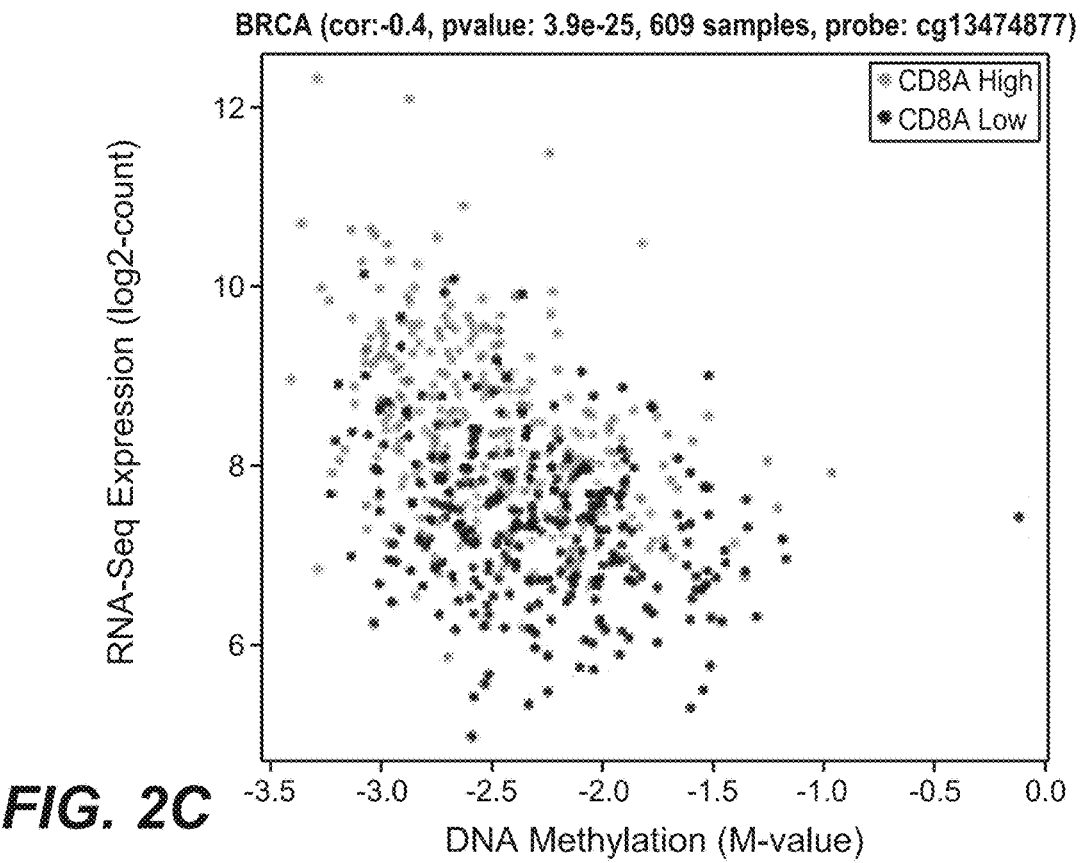
FIG. 2C shows the results of an analysis correlating PD-L1 RNA expression and PD-L1 promoter methylation in a collection of breast cancer tumors from The Cancer Genome Atlas.
Figure 2D:
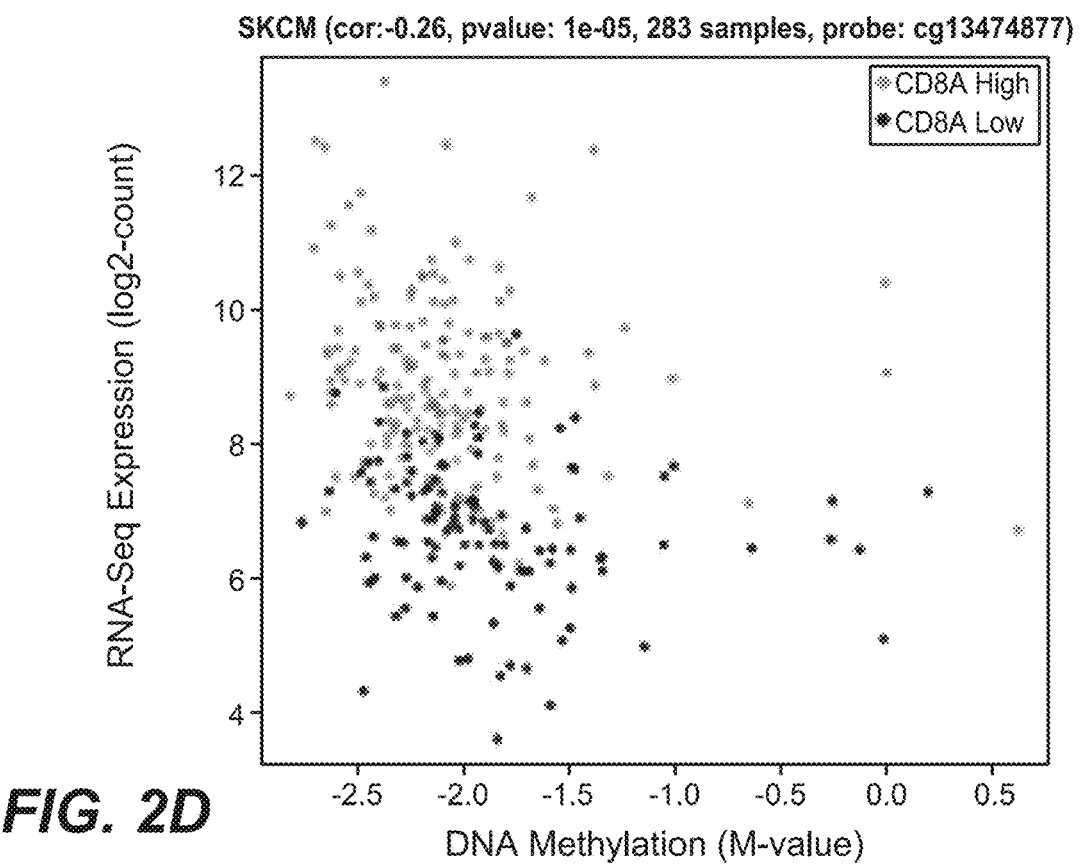
FIG. 2D shows the results of an analysis correlating PD-L1 RNA expression and PD-L1 promoter methylation in a collection of skin carcinoma tumors from The Cancer Genome Atlas.

Tumor data from The Cancer Genome Atlas (TCGA 3.0) was analyzed to further study at the association between PD-L1 expression (RNA-seq, log 2-count) versus DNA methylation (INFINIUM® Array, avg m-value CpG1 & CpG5). Tumors from four collections were included: lung adenocarcinoma (LUAD), lung squamous cell carcinoma (LUSC), breast cancer (BRCA) and skin carcinoma (SKCM). Inverse correlations between RNA expression and methylation were also seen in these patient tumor analyses: LUAD=−0.33, LUSC=−0.38, BRCA=−0.4, and SKCM=−0.25. The tumor samples were further sub-grouped and colored by CD8A expression (RNA-seq, median cutoff) in order to further parse PD-L1 expression by the amount of immune infiltrate in each tumor. Tumors with higher CD8A expression tended to also have higher PD-L1 expression and lower PD-L1 promoter methylation. See FIGS. 2A (lung adenocarcinoma), 2B (lung squamous cell carcinoma), 2C (breast cancer) and 2D (skin carcinoma).

A select number of NSCLC cell lines tested for PD-L1 expression levels and promoter methylation (see FIG. 1) were analyzed further to investigate the relationship between PD-L1 promoter methylation and PD-L1 expression in vitro. The cell lines chosen for further analysis were selected based on the average methylation levels at CpG1 and CpG5. Cell lines H661, LXFL529 and A427 were classified as having high average methylation levels at CpG1 and CpG5; cell lines H2073 and H322T were classified as having medium average methylation levels at CpG1 and CpG5; and cell line H1993 was classified as having low average methylation levels at CpG1 and CpG5.

Figure 3:
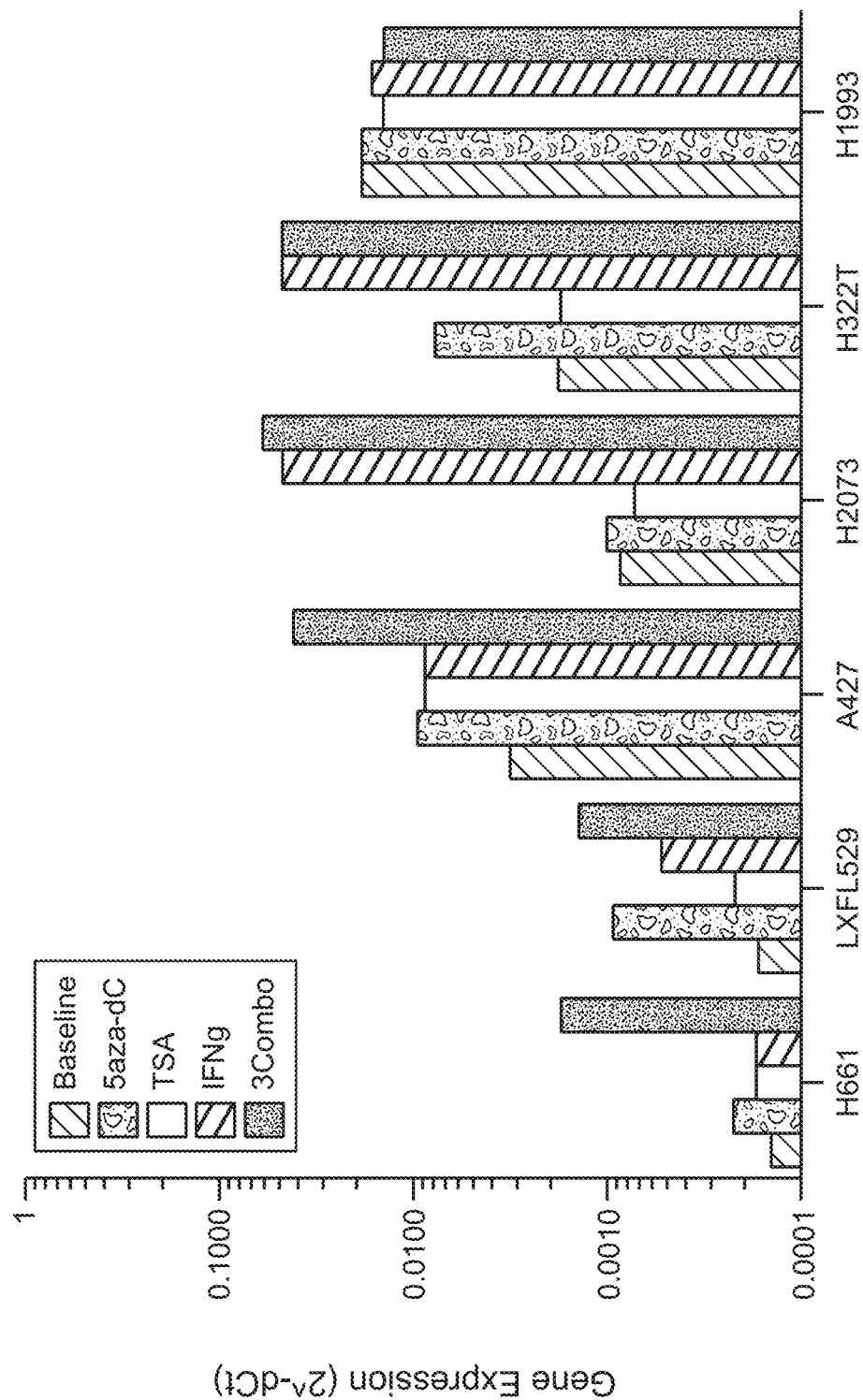
FIG. 3 shows the results of experiments performed to assess the effects of 5aza-dC, TSA, IFNg, or 5aza-dC+TSA+ IFNg treatment on the expression of PD-L1 RNA in 5 lung cancer cell lines (i.e., H661, LXFL529, A427, H2073, H322T, and H1993).

Cells from each of the cell lines were exposed to one of five conditions: (1) no treatment; (2) treatment with 1 mM 5-azacitidine-dC (5-aza-dC, a DNA demethylation agent); (3) treatment with 0.1 mM trichostatin A (TSA, a class I and class II mammalian histone deacetylase); (4) treatment with 1 ng/mL interferon gamma (IFNg); or (5) treatment with a combination of 5-aza-dC, TSA, and IFNg. PD-L1 RNA expression was then measured by qRT-PCR. As shown in FIG. 3, PD-L1 RNA expression increased in H661, LXFL529, A427, and H322T following 3 days of 5-aza-dC treatment. Only H322T demonstrated an increase in PD-L1 RNA expression following TSA treatment. Treatment with the combination of 5-aza-dC, TSA, and IFNg resulted in increased PD-L1 expression in all lines except, H1993 (i.e., the cell line having low average methylation levels at CpG1 and CpG5). H1933 already demonstrated a high level of baseline PD-L1 expression.

Figure 4A:
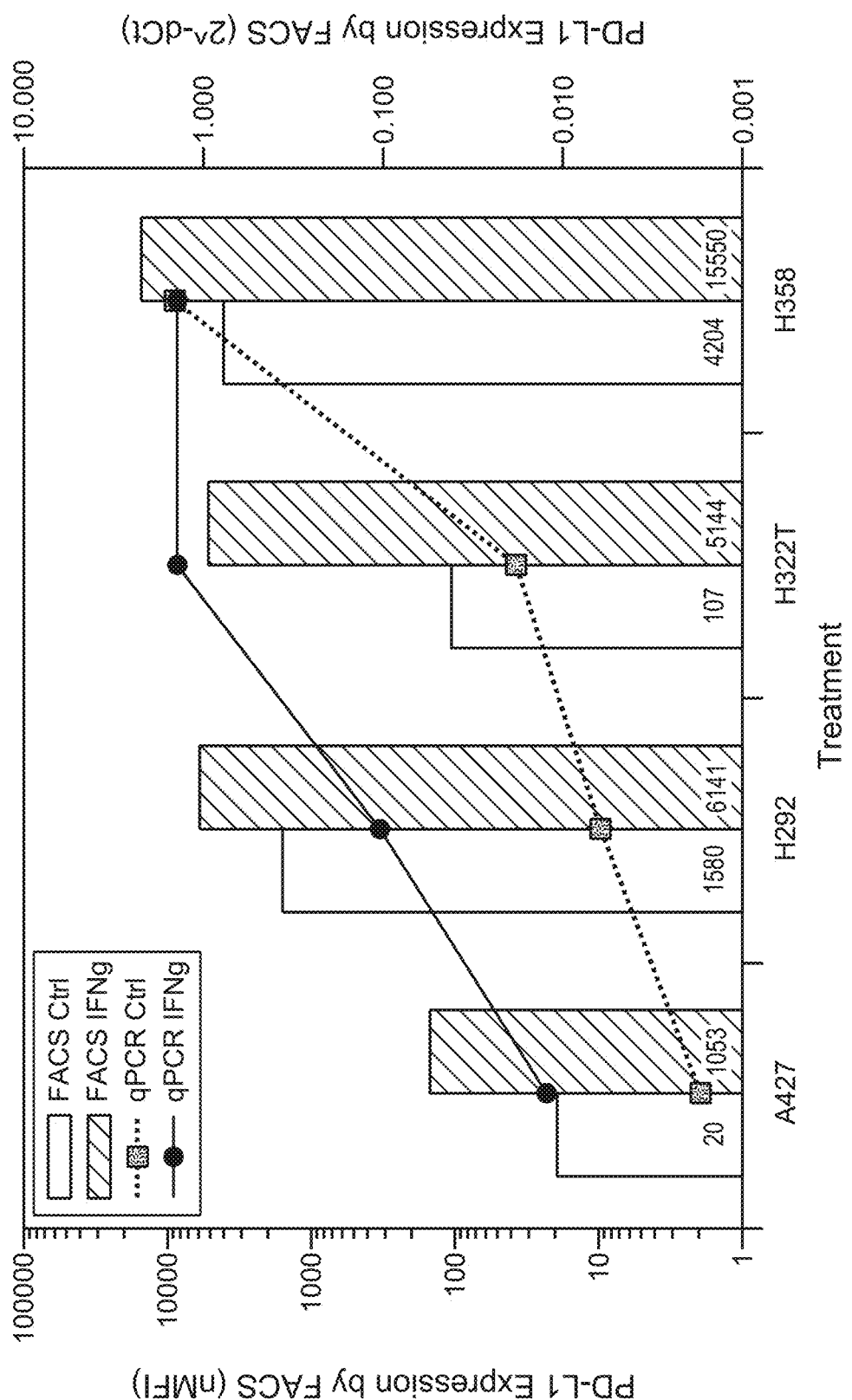
FIG. 4A shows the results of experiments performed to assess the effect of IFNg treatment on PD-L1 protein and RNA expression in four different lung cancer cell lines (A427, H292, H322T, and H358).

Four cell lines, i.e., A427 (in which CpG1 and CpG5 have a high level of methylation); H322T (in which CpG1 and CpG5 have a medium level of methylation, and in which PD-L1 expression is inducible by treatment with IFNg; H292 (in which CpG1 and CpG5 have a low level of methylation); and H358 (in which CpG1 and CpG5 have a low level of methylation) were selected to use in experiments to further investigate the relationship of PD-L1 RNA and protein expression in the presence and absence IFNg. When stimulated with IFNg, A427, H322T, H292, and H358 showed increases in PD-L1 RNA induction, irrespective of their original basal expression. See FIG. 4A. A427 and H292, which express PD-L1 RNA at low levels in the absence of IFNg, showed variable responses to IFNg stimulation with A427 remaining low (at $0.012$ $2^{-DCt}$), while H292 showing increased RNA levels (at $0.102$ $2^{-DCt}$). The greatest change in PD-L1 RNA expression was observed in H322T line, increased from $0.018$ to $1.356$ $2^{-DCt}$. The H358 cell line, which already showed high levels of baseline PD-L1 expression and low methylation level at CpG1 and CpG5, showed no significant changes to its RNA expression following stimulation.

PD-L1 protein expression loosely correlated with RNA expression in this subset of cell lines, both at baseline and following IFNg stimulation. A427 still showed almost no expression above background by FACS with a normalized Median Fluorescence Intensity (nMFI) of 20. H322T also showed low level of PD-L1 expression (nMFI of 107). See FIG. 4A. H292 showed significantly higher protein expression with an nMFI of 1580, and H358 demonstrated the highest baseline expression (nMFI of 4204). All four cell lines showed increased surface PD-L1 protein levels following IFNg treatment. In the A427 cell line, PD-L1 protein expression remained low. In the H292 and H358 cell lines, PD-L1 protein expression increased 3-4 fold, and in H322T, PD-L1 protein expression increased more than 48-fold as compared to baseline levels. Comparatively, PD-L1 protein levels in A427 following IFNg treatment increased to pre-treatment levels seen in H322T. IFNg treatment in H322T following showed that PD-L1 protein expression is highly inducible. As discussed above, baseline levels of PD-L1 protein in H322T were low. By contrast, PD-L1 protein levels in H322T following IFNg treatment were comparable to PD-L1 protein levels in H292 and H358 following IFNg treatment.

Figure 4B:
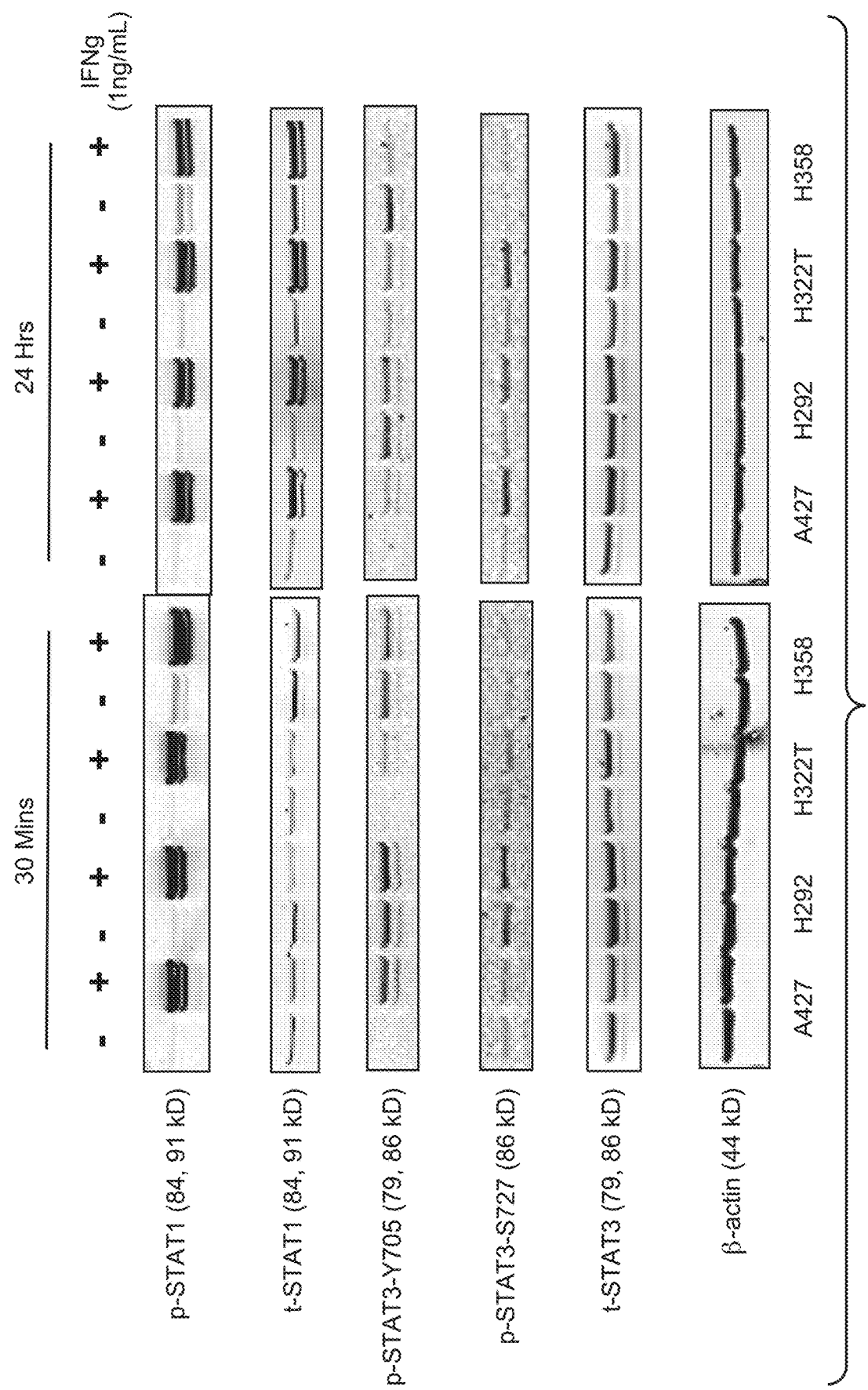
FIG. 4B shows the results of experiments performed to determine the effect of 30-minute IFNg treatment and 24-hour IFNg treatment on the IFNg/JAK/STAT signaling pathway in the A427, H292, H322T, and H358 cell lines.

Next, western blots were performed to determine whether the IFNg/JAK/STAT signaling pathway plays a role in the IFNg-mediated induction of PD-L1 transcript and protein levels in A427, H322T, H292, and H358. Briefly, cells from A427, H322T, H292, and H358 were either (a) untreated; (b) treated with IFNg for 30 minutes; or (c) treated with IFNg for 24 hours. The cells were then processed into protein lysates and run out on gels, blotted and probed with the following antibodies: (1) anti-phospho-STAT1; (2) anti-total-STAT1: (3) anti-phospho-STAT3-Y705; (4) anti-phospho-STAT3-S727; (5) anti-total-STAT3; and (6) β-actin (loading control). All four cell line showed robust p-STAT1 activation with following IFNg stimulation, with basal p-STAT1 only observed in H358. See FIG. 4B. p-STAT3-Y705, the initial activation site for STAT3, was constitutively activated in H292 (following 30 min IFNg treatment) and H358, but lost in H358 by 24 hrs following IFNg stimulation. STAT3 was further activated by the mTOR and MAPK pathways at S727. Activation of the JAK/STAT signaling pathway was observed in all cell lines by 24 hrs, except in H358 cells, which did not show p-STAT3-5727 activation before and after stimulation at both early and late timepoints. These results show that the JAK/STAT pathways (including the STAT1 pathway) are active in all four cell lines tested.

Next, the relationship between PD-L1 promoter methylation and the IFNg/JAK/STAT pathway was investigated in A427 and H358 using siRNA. As noted above, CpG1 and CpG5 had low levels of methylation in A427, and A427 showed low to no PD-L1 protein expression at baseline and following IFNg stimulation. By contrast, CpG1 and CpG5 had low levels of methylation in H358, and H358 showed high PD-L1 protein expression at baseline, which increased following IFNg stimulation. In order to determine which STAT was most crucial for PD-L1 expression in the context of methylation, cells from each cell line were dosed with (1) no siRNA; (2) Scrambled control; (3) siSTAT1; (4) siSTAT3; (5) IFNg, or (6) siSTAT1, siSTAT3, and IFNg.

Figure 4C:
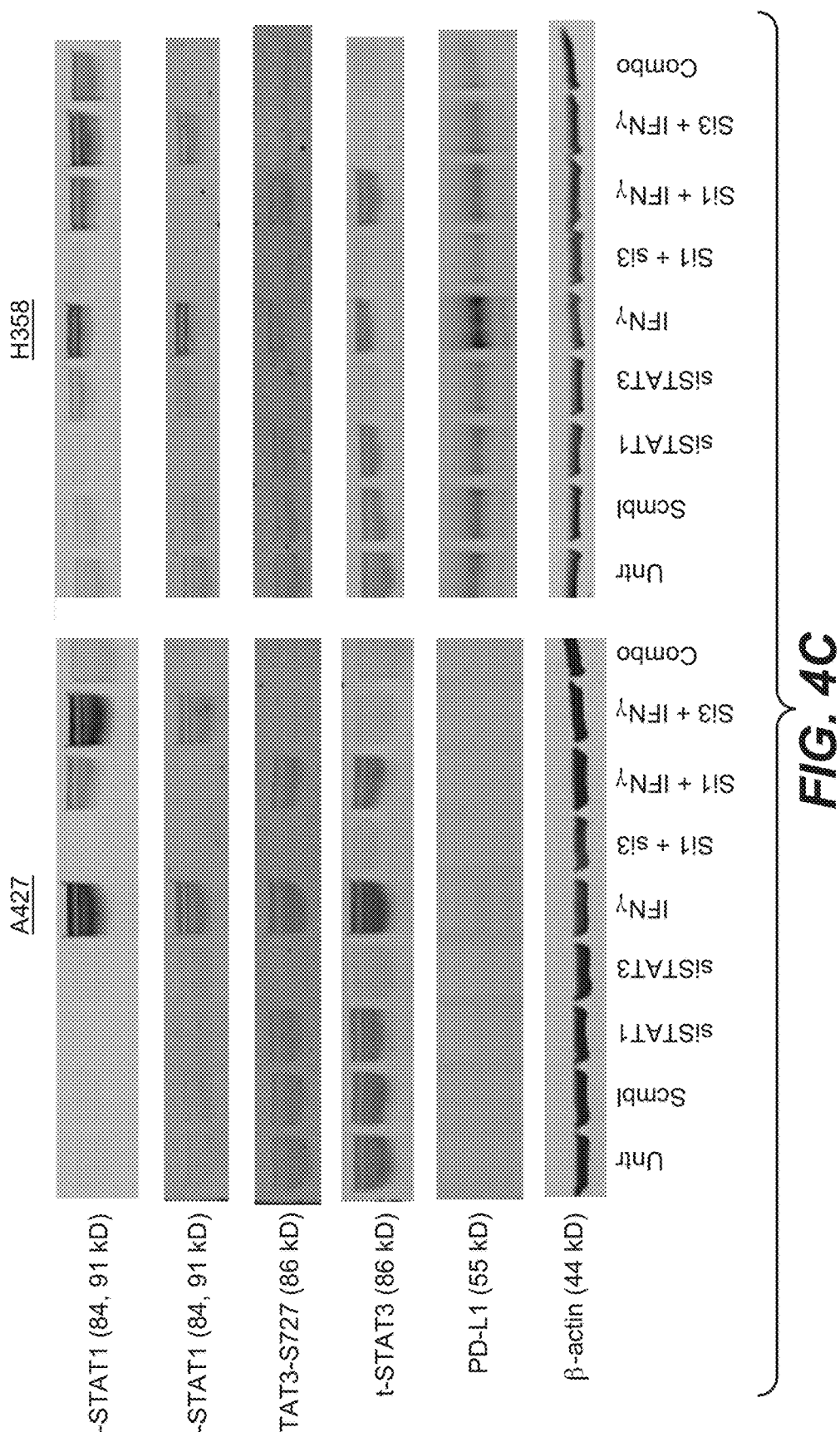
FIG. 4C shows the results of experiments performed to determine the effects of IFNg treatment and/or STAT1 and STAT3 knockdown on STAT1, STAT3 and PD-L1 expression in A427 and H358.

A427 showed no PD-L1 expression regardless of treatment, despite strong induction of activated STAT1 and STAT3 following stimulation with IFNg. See FIG. 4C. Unmethylated H358 cells showed basal constitutive PD-L1 expression that was further induced with IFNg stimulation. siSTAT3 further reduced PD-L1 basal expression. Both siSTAT1 and siSTAT3 knocked down PD-L1 expression close to baseline, whereas the combination of IFNg, and both siRNA showed the least amount of PD-L1 expression, despite the simultaneous stimulation with the siRNA interference. These results show that methylation of the PD-L1 promoter blocked PD-L1 expression despite IFNg/JAK/STAT1 or IFNg/JAK/STAT3 activation. These results also show that STAT1 and STAT3 are both needed for IFNg-stimulated PD-L1 expression and STAT3 also appears to be partially necessary for PD-L1 basal expression.

Figures 2, 5A:
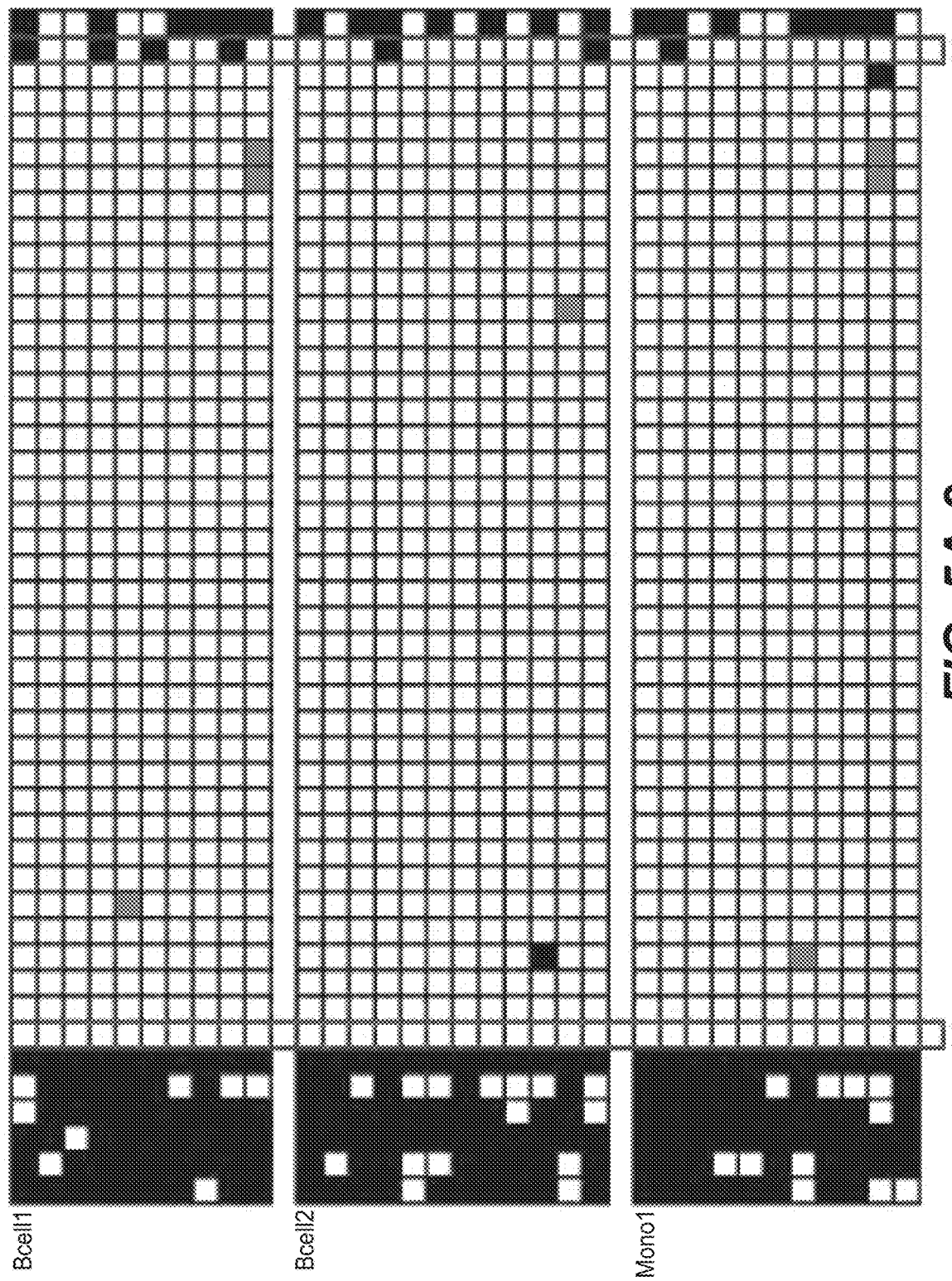
Figures 3, 5A:
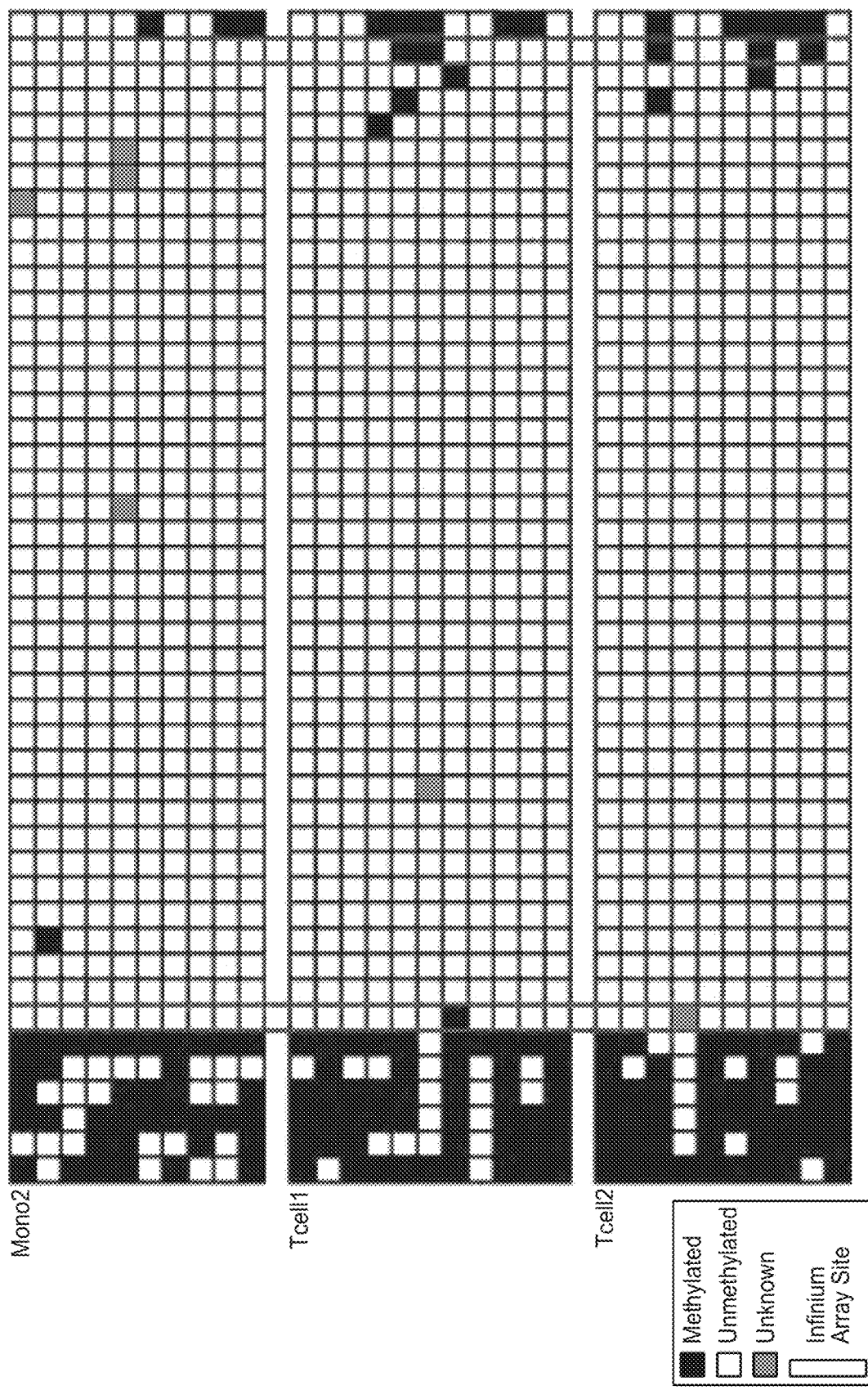
Figures 2, 5B:
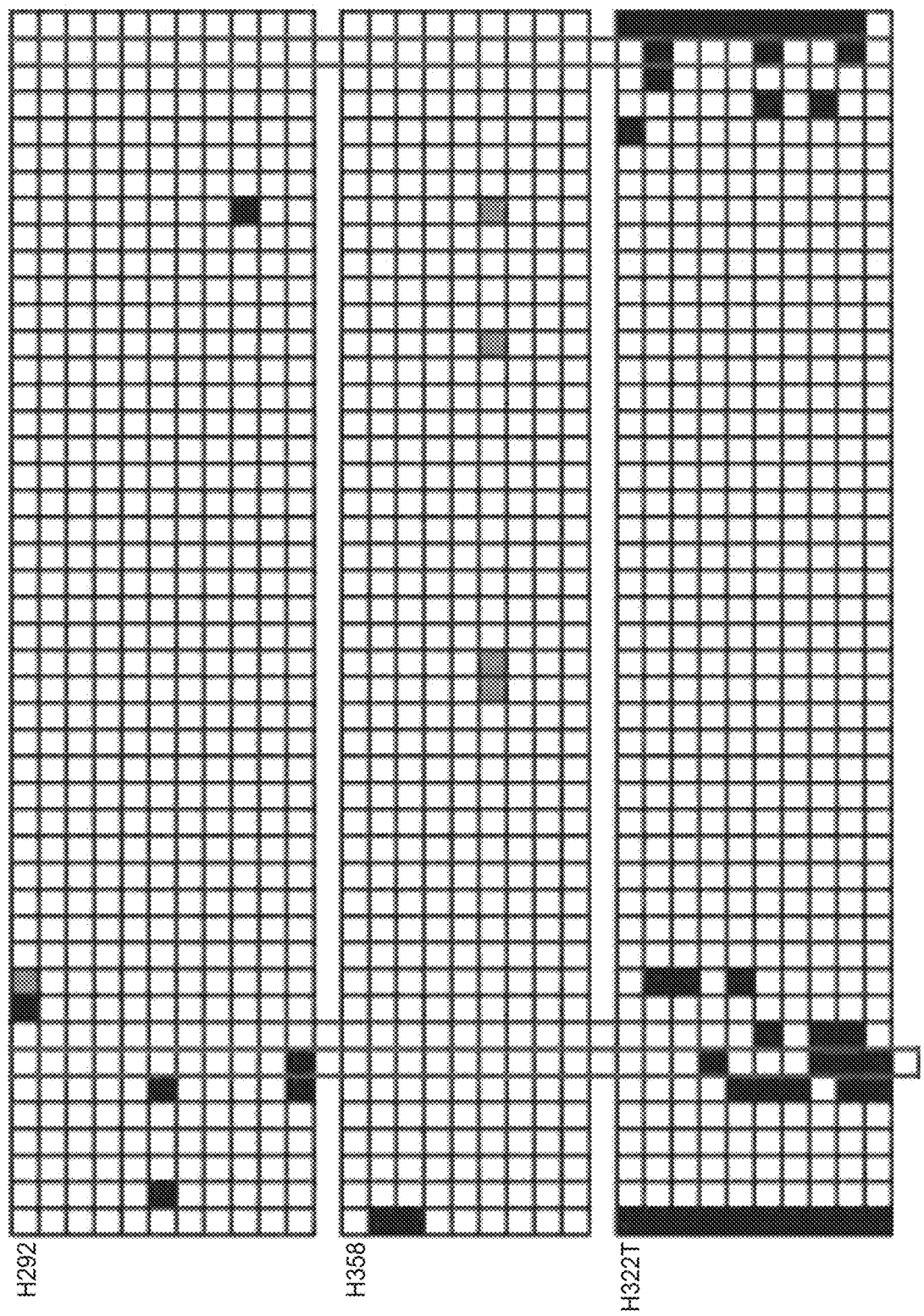
Figures 3, 5B:
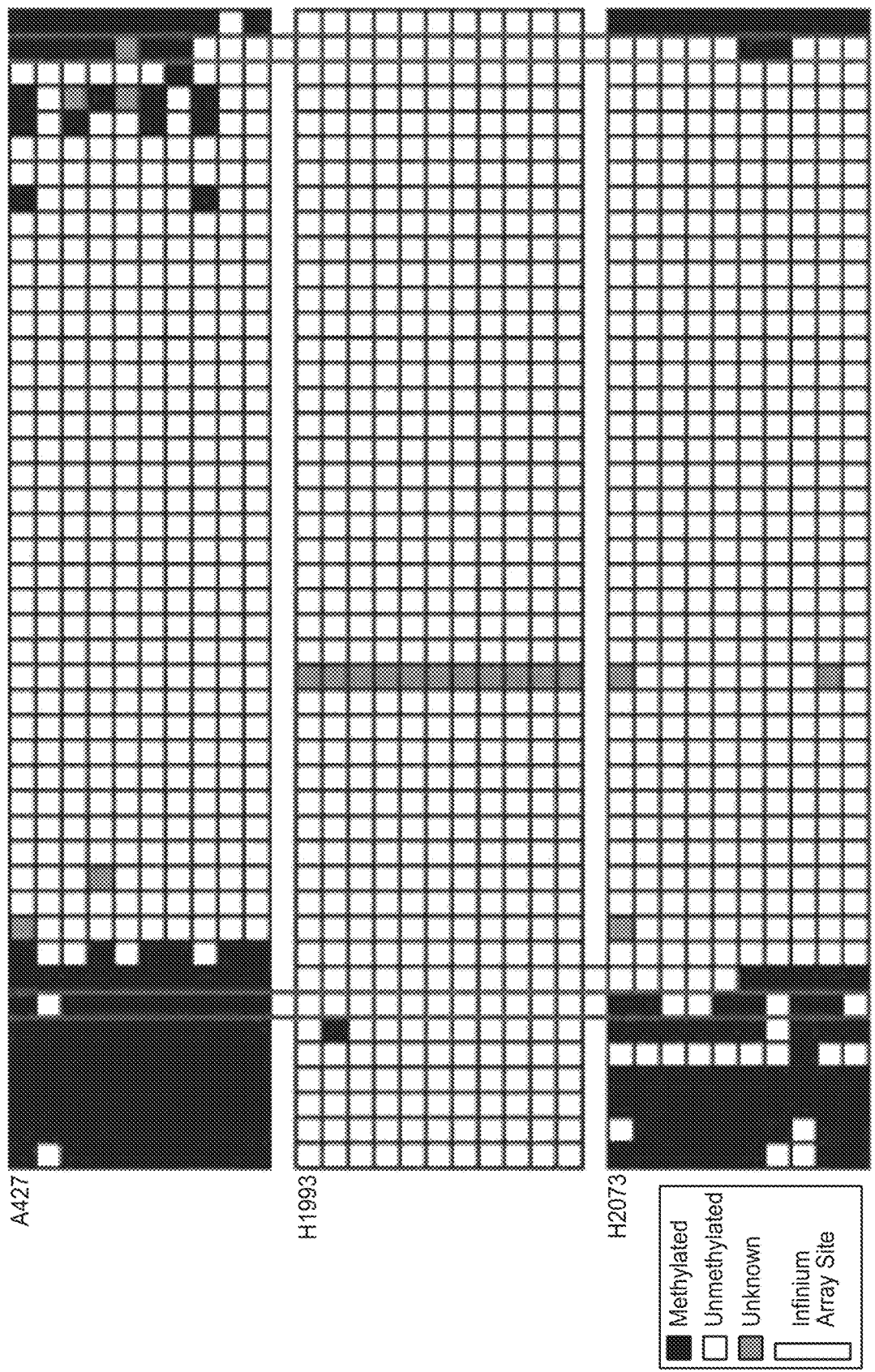

Next, bisulfite-sequencing data were superimposed onto maps of possible CpG methylation sites for peripheral blood mononuclear cell (PBMC) subsets, immortalized normal lung cell lines, and NSCLC lung lines representative of all three PD-L1 promoter methylation categories (i.e., high, medium, and low methylation levels). In FIGS. 5A and 5B, the Mut2/Cpg1 and Mut7/CpG5 are boxed in red. Little to no methylation was seen in the various PBMC subsets that could be found as immune infiltrate in patient tumors. See FIG. 5A. Normal lung cell lines also showed no methylation at these sites. See FIGS. 5A and 5B. Cell lines H358 and H1993, which expressed PD-L1 at high levels, showed no methylation at CpG1 and 5. See FIG. 5B. Cell lines H322T and H2073, which showed low, but inducible baseline PD-L1 expression, demonstrated partial methylation at both CpG sites. See FIG. 5B. A427, which was shown have low baseline PD-L1 expression, exhibited high levels of methylation at CpG1 and CpG5. As little to no methylation was seem at CpG1 and CpG5 in PBMC subsets and normal liver cell lines, methylation at the PD-L1 promoter region that is detected in a patient's whole tumor sample should therefore predominately arise from the tumor cells, and not from any other cellular subset in the sample.

Figure 6A:
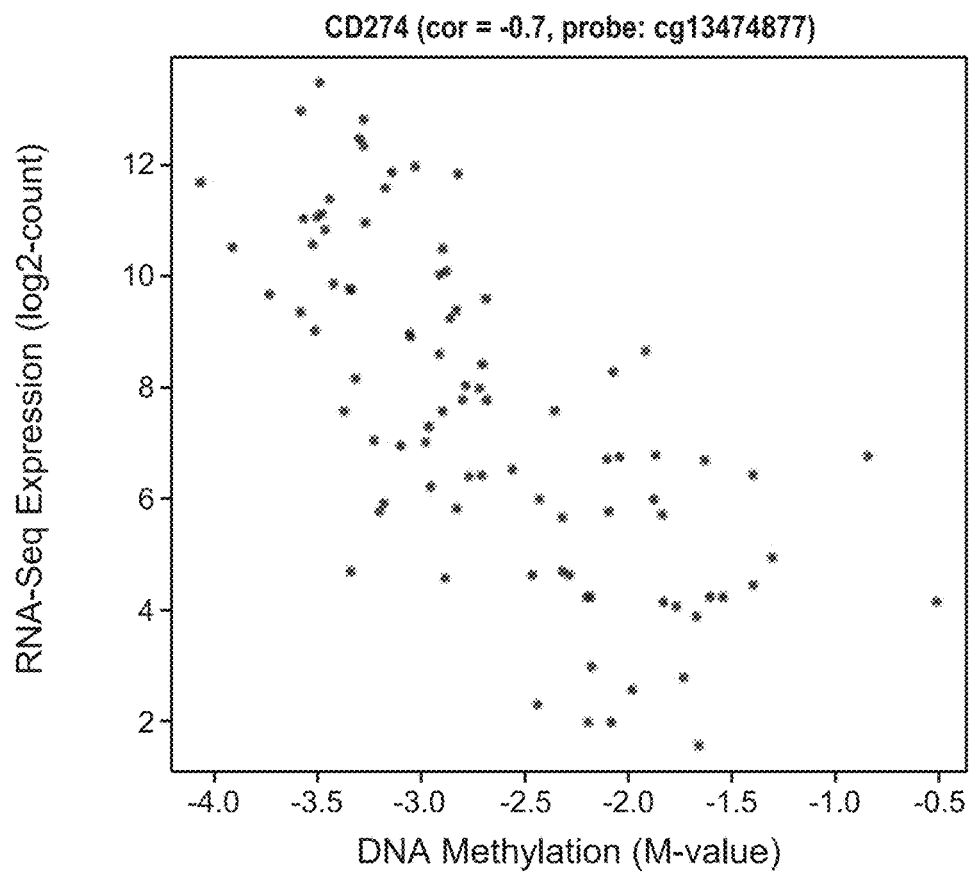
FIG. 6A shows a scatter plot that was created from Cancer Genome Project (CGP) of NSCLC cell lines directly comparing smoothened CpG1 and CpG5 methylation (M-value) on the X axis and PD-L1 expression (RNA-seq, Log 2-count) on the Y axis.
Figure 6B:
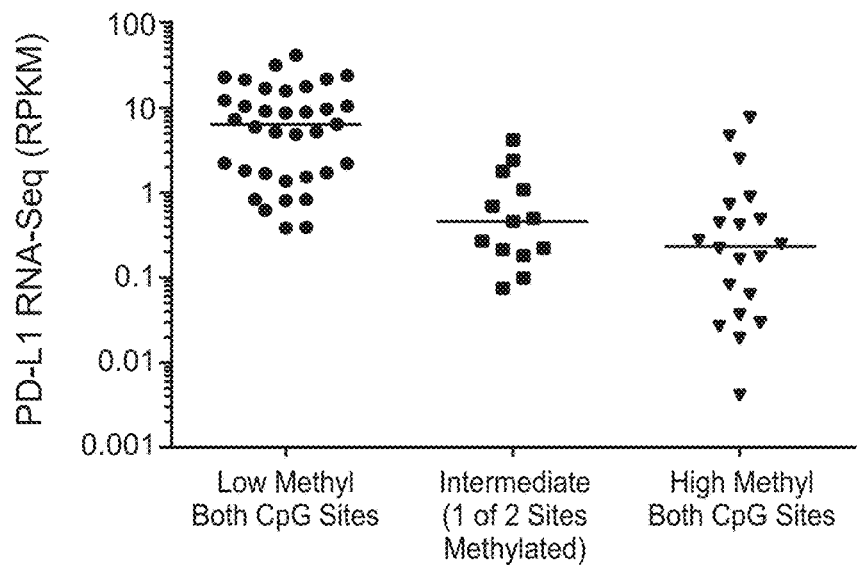
FIG. 6B shows the results of ANOVA analyses performed to determine the statistical relevance of the 3 methylation level groups (i.e., "low," "medium," and "high") into which the NSCLC cell lines from FIG. 6A were categorized.
Figure 6C:
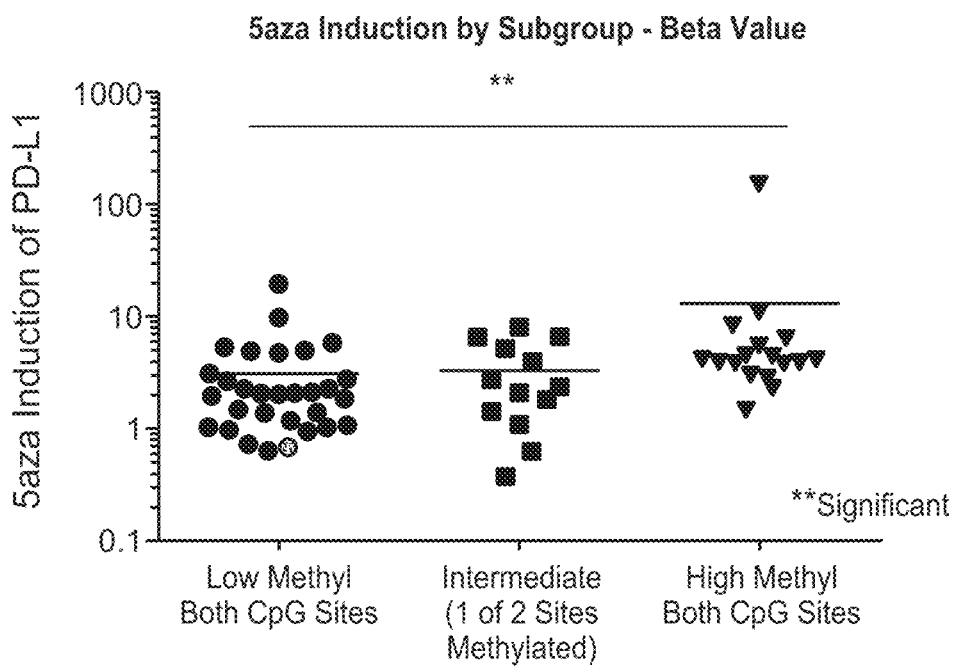
FIG. 6C shows the results of ANOVA analyses that were performed to determine the statistical relevance of the effect of 5aza-dC treatment on PD-L1 RNA expression in the NSCLC cell lines from FIG. 6A.
Figure 6D:
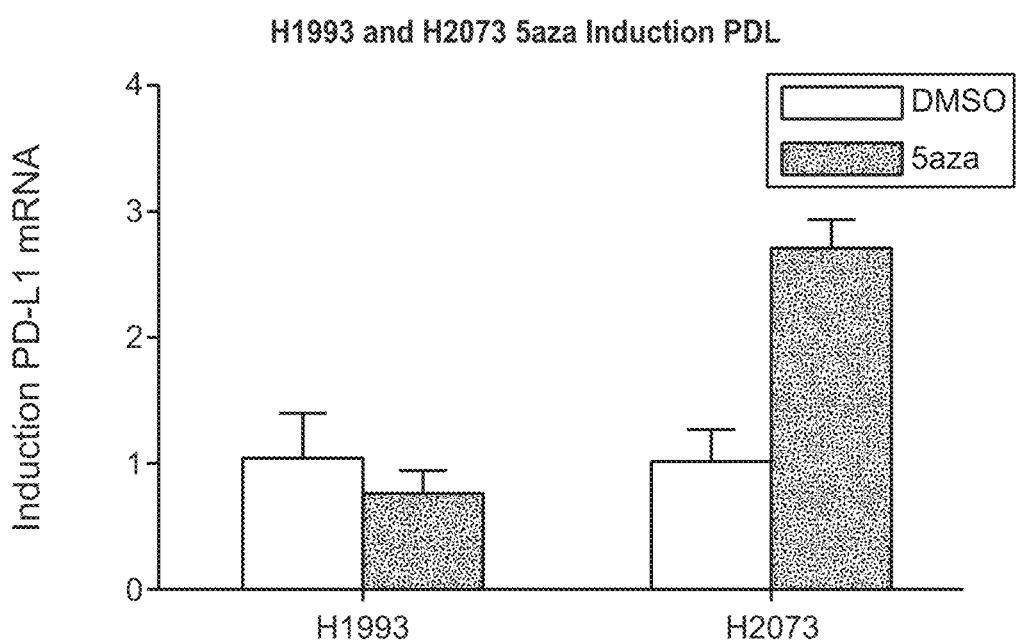
FIG. 6D shows the results of experiments that were performed to determine the effect of 5aza-dC treatment on PD-L1 RNA expression in the linked NSCLC cell lines H1993 and H2073.

NSCLC cell lines from the Cancer Genome Project (CGP) were used to create a scatter plot directly comparing smoothened CpG1 and CpG5 methylation (M-value) on the X axis and PD-L1 expression (RNA-seq, Log 2-count) on the Y axis. As shown in FIG. 6A, the data have a highly inversely correlated relationship, with a Pearson's correlation of −0.7. PD-L1 baseline expression in these cell lines is highly affected by the level of promoter methylation. The CGP cell lines analyzed in FIG. 6A were then categorized into three methylation groups: (1) low (i.e., low to no methylation at both CpG1 and CpG5), (2) intermediate (i.e., CpG1 or CpG5 site methylated), or (3) high (CpG1 and CpG5 both methylated). These groups were plotted on the X axis, with basal PD-L1 expression by RNA-seq plotted on the Y and median expression shown for each group. ANOVA analysis showed high statistical relevance for each group, upon PD-L1 expression. Group (1) (i.e., low) had the highest median PD-L1 expression, with Group (2) (i.e., intermediate) and Group (3) (i.e., high) methylation groups showing lower median PD-L1 expression. See FIG. 6B. These data show that basal PD-L1 expression is inversely regulated by the level of promoter methylation at a either CpG1 or Cpg5, but also by the number of CpG sites that are methylated.

The cell lines in the CPG NSCLC cell line panel were then treated with 5-aza-dC in order to the effect global demethylation would have on PD-L1 expression in a dataset with a larger number of cell lines. PD-L1 expression was significantly induced. Only Group (3) (i.e., high) cell lines showed significant induction of methylation-suppressed PD-L1 expression. See FIG. 6C. Additionally, two cell lines in this panel are known to have been raised from two separate samples from one patient, H1993 (low) and H2073 (intermediate). H1993 showed no significant changes in PD-L1 expression following 5-aza-dC treatment, whereas H2073 showed significant PD-L1 expression induction following demethylation of the PD-L1 promoter. See FIG. 6D. These results demonstrate that PD-L1 methylation could be a driving factor influencing PD-L1 expression, as different cell lines with dissimilar patterns of methylation at CpG1 and CpG5 have originated from the same patient.

Figure 7A:
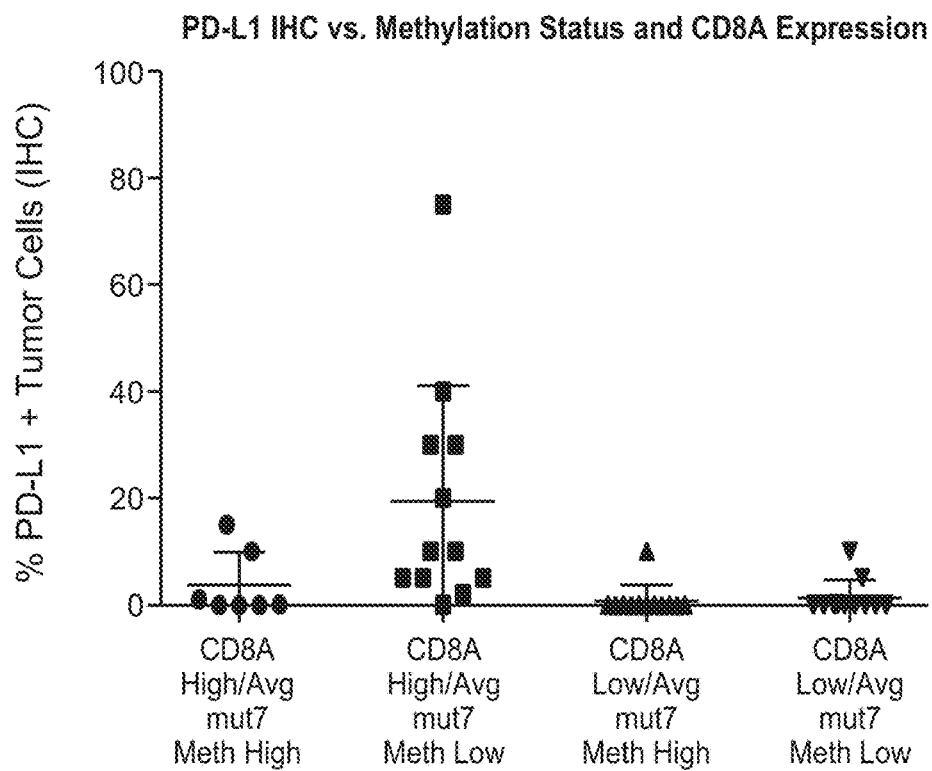
FIG. 7A shows the results of ANOVA analyses performed to determine the statistical relevance of the relationship between T-cell infiltration, methylation at CpG5 (mut7) and PD-L1 protein levels in NSCLC cell lines.
Figure 7B:
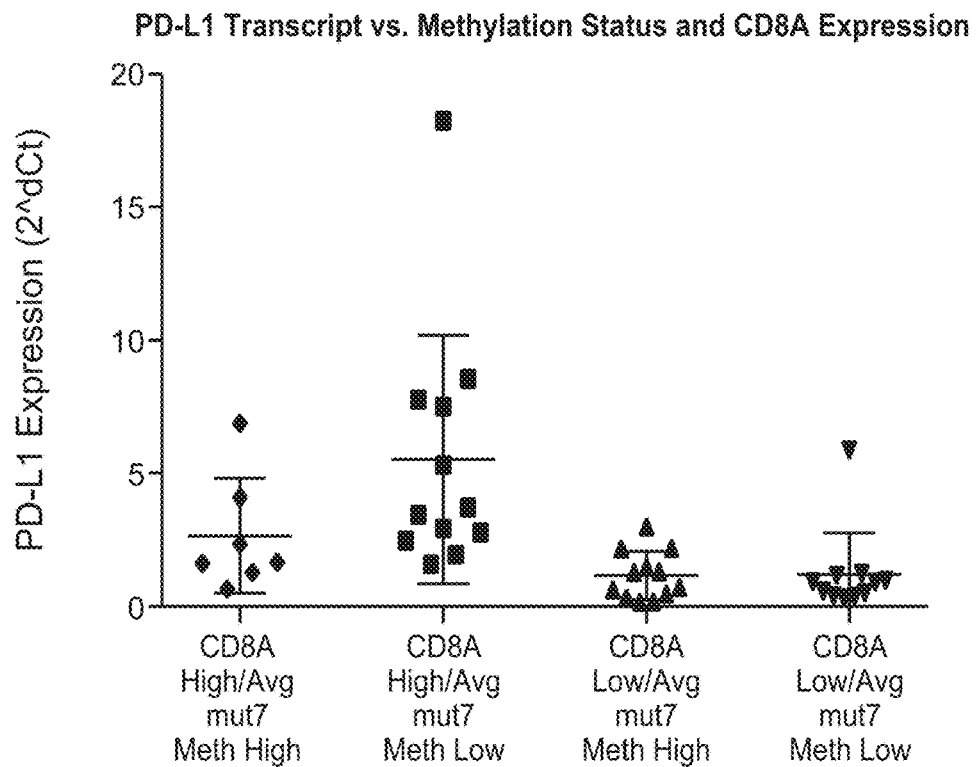
FIG. 7B shows the results of ANOVA analyses performed to determine the statistical relevance of the relationship between T-cell infiltration, methylation at CpG5 (mut7) and PD-L1 transcript levels in NSCLC cell lines.

Adaptive immunity is the process by which immune infiltrate can activate and upregulate immune checkpoint proteins, such as PD-L1, in a tumor by the release of IFNg and other factors from activated T cells. The results of the experiments described above suggest that this PD-L1 activation is blocked in cell lines having a high level of methylation at CpG1 and/or CpG5. A collection of human NSCLC tumor samples were analyzed to detect activated T cell infiltration (CD8A gene expression, Fluidigm) and tumor cell PD-L1 promoter methylation at CpG5 (also referred to as mut7). As shown in FIGS. 7A and 7B, only highly infiltrated tumor samples with low CpG5/mut7 methylation showed high PD-L1 tumor cell expression by both IHC (protein, see FIG. 7A) and by qRT-PCR (RNA, see FIG. 7B). Low or non-infiltrated tumors or tumors with high CpG5 methylation all showed low PD-L1 protein and RNA expression. Tumor cell PD-L1 upregulation by the infiltration of activated T cells is still blocked by promoter methylation at CpG5 in these NSCLC patient tumor samples.

Next, experiments were performed to determine whether CpG methylation at CpG1 and CpG5 can physically block binding of STAT1 and/or STAT3 to the PD-L1 promoter region (CpG1) and Intron 1 (CpG5). There are two known STAT Binding Motifs in close proximity to CpG1 in the PD-L1 promoter. The A427 (i.e., methylated) and H358 (i.e., unmethylated) cell lines described above were grown almost to confluence and then stimulated with either a control buffer or IFNγ, as described above. In the following morning, the cells were split into two aliquots, the first for use in bisulfate sequencing, and the second for use in ChIP-Seq to assess STAT1 and STAT3 binding. Bisulfite sequencing confirmed the methylation status for both cell lines and a differential binding pattern was observed between the two cell lines, as represented by the significant peaks analysis by MACS Peak Calling.

Figures 8, 8A:
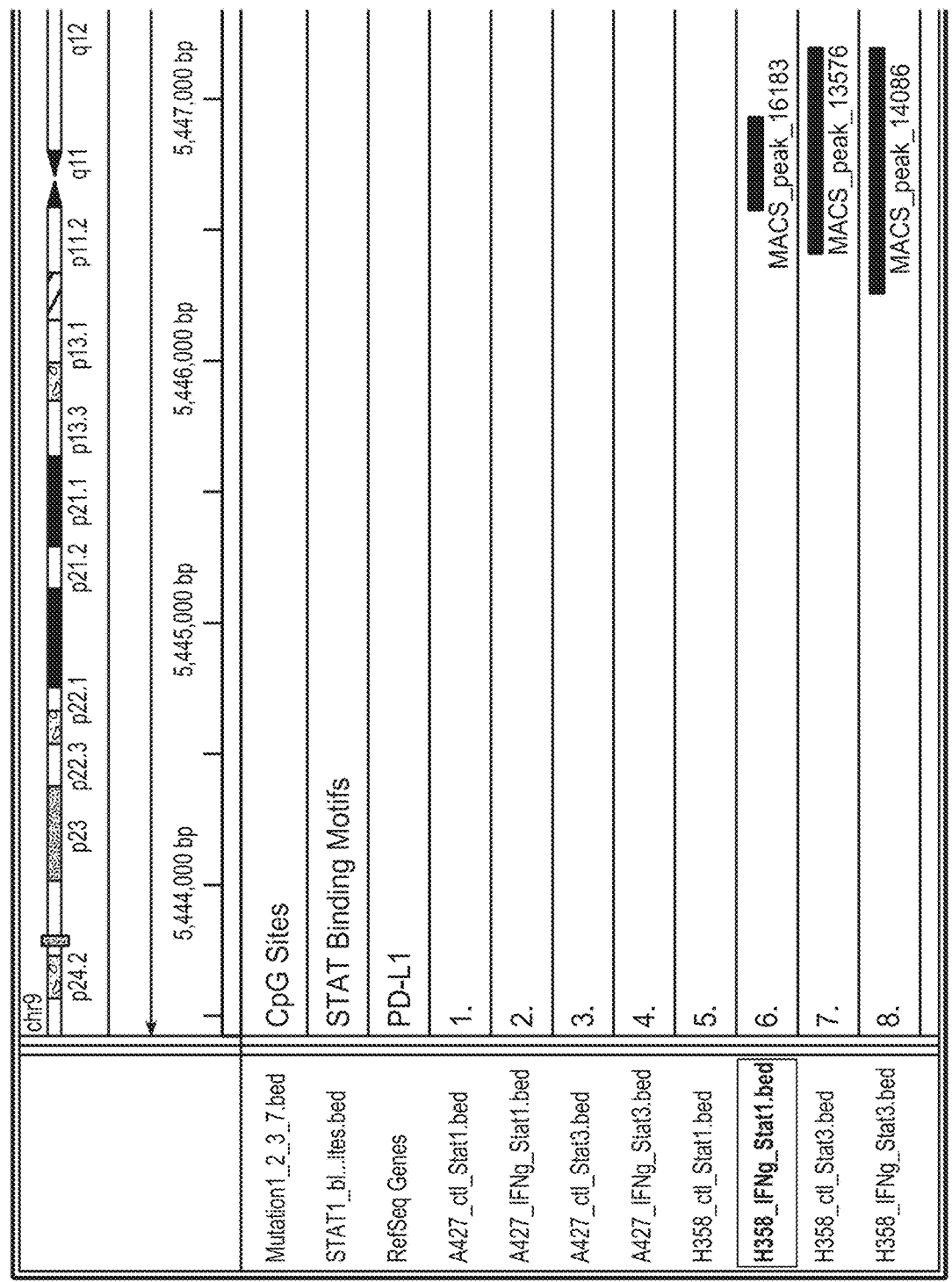
FIG. 8A-8B provides bed files displayed in the IgV Integrated Genomics Viewer (Broad Institute). The bed files provide the results of ChIP-Seq experiments performed to determine whether STAT1 and/or STAT3 bind the PD-L1 promoter region in A427 and H358 cell lines.
Figure 8B:
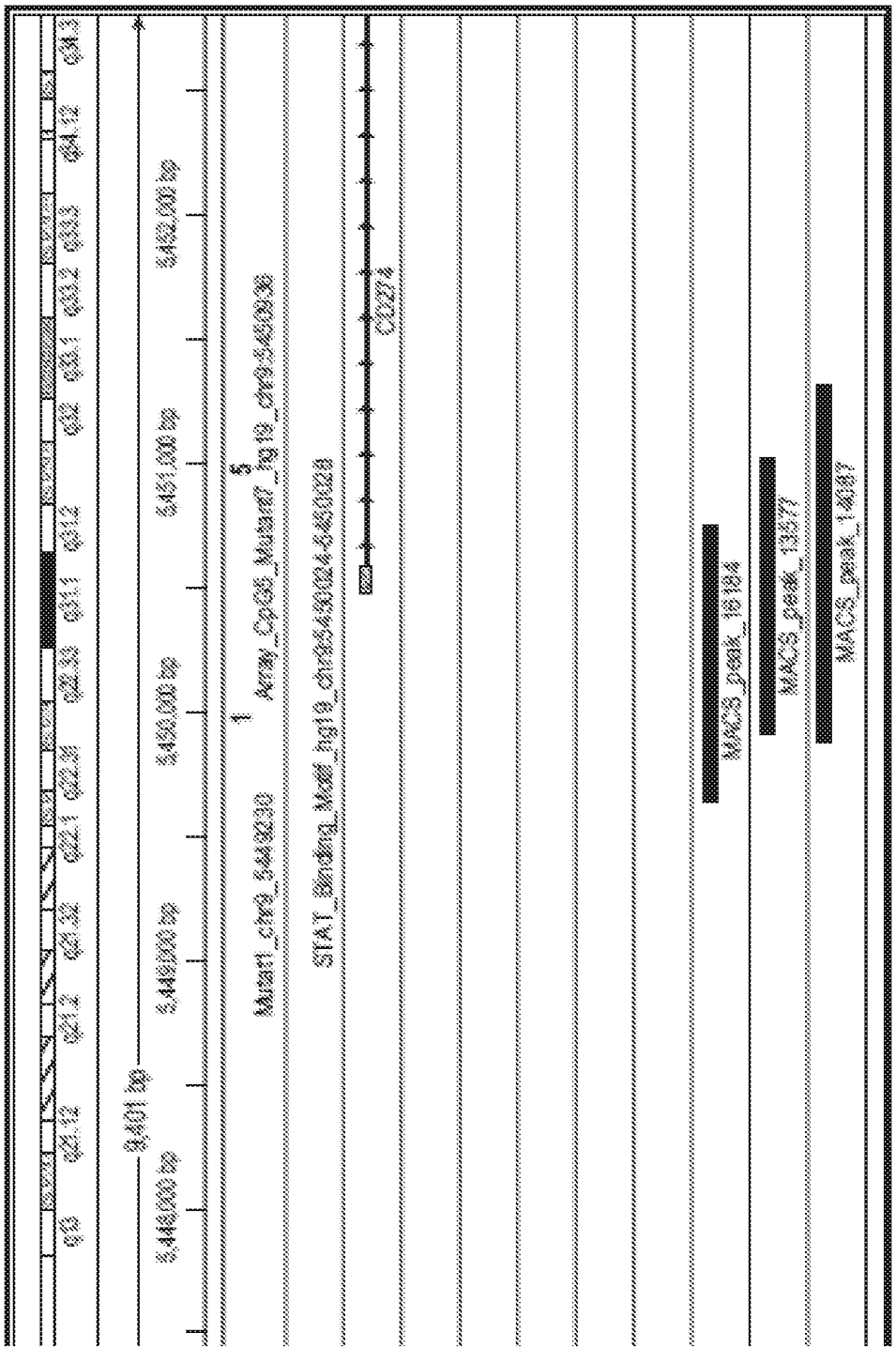

The results of the ChIP-Seq experiments are shown in FIG. 8 as bed files displayed in the IgV Integrated Genomics Viewer (Broad Institute). In FIG. 8, the top bed file contains the coordinates of the CpG's found in the PD-L1 promoter region and Intron1. CpG1 and CpG5 are labeled. The second bed file contains the coordinates of the known STAT Binding Motifs in the PD-L1 promoter region. The third bed file contains Hg19 sequence and gene structure for PD-L1/CD274. The $4^{th}$-11th bed files (numbered 1-8) are the MACS significant binding files, generated downstream from our ChIP-Seq experiment with STAT1 and STAT3 in the NSCLC cell lines A427 and H358.

Methylated A427 cell lines showed no binding of either STAT protein, with or without IFNγ stimulation. See Table 4. Such results indicate that methylation of CpG1, and possibly CpG5, in A427 completely blocks binding of STAT1 and STAT3 to the STAT Binding Motifs near CpG1 in the PD-L1 promoter. Unstimulated H358 showed no binding by STAT1, but STAT1 was shown to bind the PD-L1 promoter following IFNγ stimulation. See Table 4. H358 cell lines were bound by STAT3 regardless of stimulation. See Table 4. As shown earlier, H358 already have a very high basal level of PD-L1 RNA expression and these results suggest that the STAT3 transcription factor might be the driver of the high level of basal PD-L1 expression in this cell line.

TABLE 4

Binging of STAT1 and STAT3 near CpG1 in the PD-L1 promoter

| Sample # | Cell Line | Methylation at PD-L1 promoter | Stimulation | chIP | Binding |
|---|---|---|---|---|---|
| 1 | A427 | HIGH | Control | STAT1 | NO |
| 2 | A427 | HIGH | IFNγ | STAT1 | NO |
| 3 | A427 | HIGH | Control | STAT3 | NO |
| 4 | A427 | HIGH | IFNγ | STAT3 | NO |
| 5 | H358 | LOW | Control | STAT1 | NO |
| 6 | H358 | LOW | IFNγ | STAT1 | YES |
| 7 | H358 | LOW | Control | STAT3 | YES |
| 8 | H358 | LOW | IFNγ | STAT3 | YES |

The preceding Examples are offered for illustrative purposes only, and are not intended to limit the scope of the present invention in any way. Various modifications of the invention in addition to those shown and described herein will become apparent to those skilled in the art from the foregoing description and fall within the scope of the appended claims.

What is claimed is:

1. A method of treating cancer in a subject comprising administering to the subject an effective amount of an anti-PD-L1 antibody, wherein treatment is based upon the subject having medium or low level of methylation at genomic coordinate hg19 chr9:5449887-5449891 and/or at genomic coordinate hg19 chr9: 5450934-5451072 in a sample containing cancer cells from the subject,
   (i) wherein medium level of methylation is between about 20% to about 40% methylation and wherein low level of methylation is less than about 20% methylation, where the methylation level is determined by bisulfite sequencing,
   (ii) wherein the medium level of methylation is between about 5% to about 60% methylation and wherein low level of methylation is less than about 5% methylation, where the methylation level is determined by next-generation bisulfite sequencing, or
   (iii) wherein medium level of methylation is a beta value between about 0.2 to 0.3 and wherein low level of methylation is a beta value of less than about 0.2, where the methylation level is determined using a methylation chip array.

2. A method of treating cancer in a subject provided that the subject has been found to have medium or low level of methylation at genomic coordinate hg19 chr9:5449887-5449891 and/or at genomic coordinate hg19 chr9: 5450934-5451072 in a sample containing cancer cells from the subject, the treatment comprising administering an effective amount of an anti-PD-L1 antibody to the subject,
   (i) wherein medium level of methylation is between about 20% to about 40% methylation and wherein low level of methylation is less than about 20% methylation, where the methylation level is determined by bisulfite sequencing,
   (ii) wherein the medium level of methylation is between about 5% to about 60% methylation and wherein low level of methylation is less than about 5% methylation, where the methylation level is determined by next-generation bisulfite sequencing, or
   (iii) wherein medium level of methylation is a beta value between about 0.2 to 0.3 and wherein low level of methylation is a beta value of less than about 0.2, where the methylation level is determined using a methylation chip array.

3. A method of treating cancer, comprising:
   (a) selecting a subject having cancer, wherein said subject has medium or low level of methylation at genomic coordinate hg19 chr9:5449887-5449891 and/or at genomic coordinate hg19 chr9: 5450934-5451072 in a sample containing cancer cells from the subject; and
   (b) administering to the subject selected in step a) an effective amount of an anti-PD-L1 antibody,
      (i) wherein medium level of methylation is between about 20% to about 40% methylation and wherein low level of methylation is less than about 20% methylation, where the methylation level is determined by bisulfite sequencing,
      (ii) wherein the medium level of methylation is between about 5% to about 60% methylation and wherein low level of methylation is less than about 5% methylation, where the methylation level is determined by next-generation bisulfite sequencing, or
      (iii) wherein medium level of methylation is a beta value between about 0.2 to 0.3 and wherein low level of methylation is a beta value of less than about 0.2, where the methylation level is determined using a methylation chip array.

4. A method of treating cancer in a subject comprising:
   (a) measuring methylation level at genomic coordinate hg19 chr9:5449887-5449891 and/or at genomic coordinate hg19 chr9: 5450934-5451072 in a sample containing cancer cells from the subject; and, (b) administering an effective amount of an anti-PD-L1 antibody to the subject who has been determined to have a medium or low level of methylation at genomic coordinate hg19 chr9:5449887-5449891 and/or at genomic coordinate hg19 chr9: 5450934-5451072, thereby treating cancer in the subject,
  (i) wherein medium level of methylation is between about 20% to about 40% methylation and wherein low level of methylation is less than about 20% methylation, where the methylation level is determined by bisulfite sequencing,
  (ii) wherein the medium level of methylation is between about 5% to about 60% methylation and wherein low level of methylation is less than about 5% methylation, where the methylation level is determined by next-generation bisulfite sequencing, or
  (iii) wherein medium level of methylation is a beta value between about 0.2 to 0.3 and wherein low level of methylation is a beta value of less than about 0.2, where the methylation level is determined using a methylation chip array.

5. The method of claim 1, wherein the subject has medium or low level of methylation at genomic coordinate hg19 chr9:5449887-5449891 or at genomic coordinate hg19 chr9: 5450934-5451072.

6. The method of claim 1, wherein the subject has medium or low level of methylation at genomic coordinate hg19 chr9:5449887-5449891 and at genomic coordinate hg19 chr9: 5450934-5451072.

7. The method of claim 1, wherein the sample from the subject shows evidence of immune cell infiltration.

8. The method of claim 7, wherein evidence of immune cell infiltration is indicated by CD8$^+$ lymphocytes detected via western blot, ELISA, flow cytometry, qPCR, qRT-PCR, transcriptome profiling, microarray analysis, or next generation sequencing.

9. The method of claim 1, wherein the cancer is lung cancer, breast cancer, bladder cancer or melanoma.

10. The method of claim 9, wherein the cancer is lung cancer, and wherein the lung cancer is non-small cell lung cancer, lung squamous cell carcinoma, or lung adenocarcinoma.

11. The method of claim 1, wherein the anti-PD-L1 antibody inhibits the binding of PD-L1 to PD-1.

12. The method of claim 1, wherein the anti-PD-L1 antibody inhibits the binding of PD-L1 to B7-1.

13. The method of claim 1, wherein the anti-PD-L1 antibody inhibits the binding of PD-L1 to both PD-1 and B7-1.

14. The method of claim 1, wherein the anti-PD-L1 antibody is a monoclonal antibody.

15. The method of claim 1, wherein the anti-PD-L1 antibody is an antibody fragment selected from the group consisting of Fab, Fab'-SH, Fv, scFv, and (Fab')$_2$ fragments.

16. The method of claim 1, wherein the anti-PD-L1 antibody is a humanized antibody or a human antibody.

17. The method of claim 1, wherein the anti-PD-L1 antibody comprises a heavy chain comprising HVR-H1 sequence of SEQ ID NO:15, HVR-H2 sequence of SEQ ID NO:16, and HVR-H3 sequence of SEQ ID NO:3; and a light chain comprising HVR-L1 sequence of SEQ ID NO:17, HVR-L2 sequence of SEQ ID NO:18, and HVR-L3 sequence of SEQ ID NO:19.

18. The method of claim 1, wherein the anti-PD-L1 antibody comprises a heavy chain variable region comprising the amino acid sequence of SEQ ID NO:24 and a light chain variable region comprising the amino acid sequence of SEQ ID NO:21.

19. The method of claim 1, wherein the nucleic acid sequence of genomic coordinate hg19 chr9:5449887-5449891 is SEQ ID NO: 22.

20. The method of claim 1, wherein the nucleic acid sequence of hg19 chr9: 5450934-5451072 is SEQ ID NO: 23.

* * * * *